(12) United States Patent
Bereznak et al.

(10) Patent No.: US 9,730,447 B2
(45) Date of Patent: *Aug. 15, 2017

(54) FUNGICIDAL AMIDES

(71) Applicant: E I DU PONT DE NEMOURS AND COMPANY, Wilmington, DE (US)

(72) Inventors: James Francis Bereznak, Newtown Square, PA (US); Andrew Edmund Taggi, Newark, DE (US); Moumita Kar, Hyderabad (IN); Ravisekhara Pochimireddy Reddy, Secunderabad (IN); Matthew James Campbell, Rising Sun, MD (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/783,622

(22) PCT Filed: Apr. 11, 2014

(86) PCT No.: PCT/US2014/033752
§ 371 (c)(1),
(2) Date: Oct. 9, 2015

(87) PCT Pub. No.: WO2014/172190
PCT Pub. Date: Oct. 23, 2014

(65) Prior Publication Data
US 2016/0081337 A1    Mar. 24, 2016

Related U.S. Application Data

(60) Provisional application No. 61/811,907, filed on Apr. 15, 2013.

(51) Int. Cl.
*A01N 43/60* (2006.01)
*C07D 215/20* (2006.01)
(Continued)

(52) U.S. Cl.
CPC ............ *A01N 43/60* (2013.01); *A01N 43/56* (2013.01); *A01N 43/58* (2013.01); *C07D 215/20* (2013.01);
(Continued)

(58) Field of Classification Search
CPC .. C07D 215/20; C07D 231/14; C07D 401/04; C07D 401/14; C07D 403/04; C07D 405/04; C07D 405/06; C07D 417/14; C07D 419/10; A01N 43/56; A01N 43/58; A01N 43/60
See application file for complete search history.

(56) References Cited

FOREIGN PATENT DOCUMENTS

WO    2004/041210 A2    5/2004
WO    2008/148570 A1    12/2008
(Continued)

*Primary Examiner* — Sarah Pihonak
(74) *Attorney, Agent, or Firm* — Reed A Coats

(57) ABSTRACT

Disclosed are compounds of Formula 1, including all stereoisomers, N-oxides, and salts thereof,

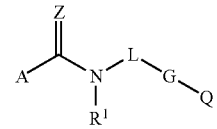

wherein
A is a radical selected from the group consisting of A-1 through A-11,
L is —C($R^{12a}$)$R^{12b}$—C($R^{13a}$)$R^{13b}$—; or 1,2-phenylene
G is a radical selected from the group consisting of

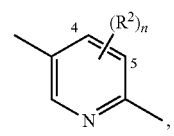

G-1

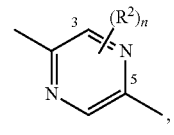

G-2

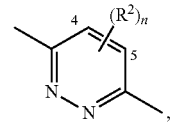

G-3

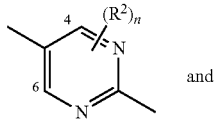

G-4 and

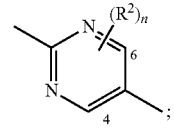

G-5 and $R^1$, $R^2$, $R^{12a}$, $R^{12b}$, $R^{13a}$, $R^{13b}$ and Q are as defined in the disclosure. Also disclosed are compositions containing the compounds of Formula 1 and methods for controlling plant disease caused by a fungal pathogen comprising applying an effective amount of a compound or a composition of the invention.

14 Claims, No Drawings

(51) Int. Cl.
*C07D 231/14* (2006.01)
*C07D 401/04* (2006.01)
*C07D 403/04* (2006.01)
*C07D 405/04* (2006.01)
*C07D 405/06* (2006.01)
*C07D 417/14* (2006.01)
*C07D 419/10* (2006.01)
*A01N 43/56* (2006.01)
*A01N 43/58* (2006.01)
*C07D 401/14* (2006.01)

(52) U.S. Cl.
CPC ......... *C07D 231/14* (2013.01); *C07D 401/04* (2013.01); *C07D 401/14* (2013.01); *C07D 403/04* (2013.01); *C07D 405/04* (2013.01); *C07D 405/06* (2013.01); *C07D 417/14* (2013.01); *C07D 419/10* (2013.01)

(56) References Cited

FOREIGN PATENT DOCUMENTS

| | | |
|---|---|---|
| WO | 2014/004064 A1 | 1/2014 |
| WO | 2014/172191 A1 | 10/2014 |

FUNGICIDAL AMIDES

FIELD OF THE INVENTION

This invention relates to certain amides, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

SUMMARY OF THE INVENTION

This invention is directed to compounds of Formula 1 (including all stereoisomers), N-oxides, and salts thereof, agricultural compositions containing them and their use as fungicides:

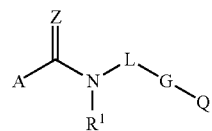

1 wherein
A is a radical selected from the group consisting of

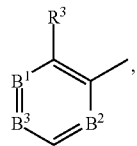

A-1

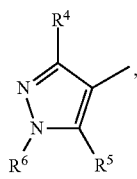

A-2

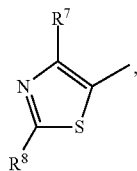

A-3

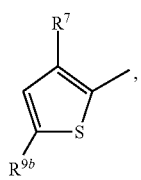

A-4

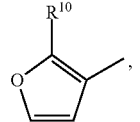

A-5

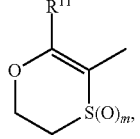

A-6

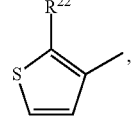

A-7

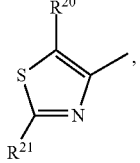

A-8

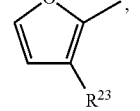

A-9

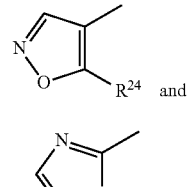

A-10 and

A-11

Z is O or S;
$R^1$ is H, cyclopropyl or $C_1$-$C_2$ alkoxy;
L is —$C(R^{12a})R^{12b}$—$C(R^{13a})R^{13b}$—, wherein the carbon atom bonded to $R^{12a}$ and $R^{12b}$ is also bonded to the carboxamide nitrogen atom in Formula 1; or 1,2-phenylene optionally substituted with up to 4 substituents independently selected from halogen and $C_1$-$C_2$ alkyl;
G is a radical selected from the group consisting of

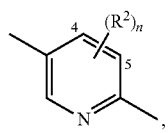

G-1

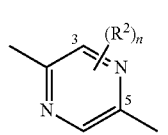

G-2

-continued

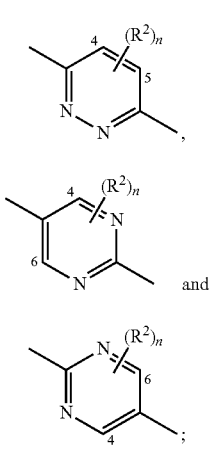

each $R^2$ is independently halogen, nitro, cyano, $C_1$-$C_5$ alkyl, $C_1$-$C_5$ haloalkyl, $C_1$-$C_5$ alkoxy, $C_1$-$C_5$ haloalkoxy or $C_3$-$C_5$ cycloalkyl;
$B^1$ is CH or N;
$B^2$ is CH or N;
$B^3$ is CH or N;
provided when $B^1$ and $B^2$ are both N, then $B^3$ is CH;
$R^3$ is halogen, $C_1$-$C_3$ alkyl or $C_1$-$C_3$ haloalkyl;
$R^4$ is halogen, $C_1$-$C_3$ alkyl or $C_1$-$C_3$ haloalkyl;
$R^5$ is H, halogen, $C_1$-$C_3$ alkyl or $C_1$-$C_3$ haloalkyl;
$R^6$ is $C_1$-$C_2$ alkyl;
$R^7$ is halogen, $C_1$-$C_3$ alkyl or $C_1$-$C_3$ haloalkyl;
$R^8$ is H, $C_1$-$C_2$ alkyl or $C_1$-$C_2$ haloalkyl;
$R^{9a}$ is H, halogen, $C_1$-$C_3$ alkyl, $C_1$-$C_3$ haloalkyl or $C_1$-$C_3$ alkylthio;
$R^{9b}$ is H, halogen, $C_1$-$C_3$ alkyl or $C_1$-$C_3$ haloalkyl;
$R^{10}$ is halogen, $C_1$-$C_3$ alkyl or $C_1$-$C_3$ haloalkyl;
$R^{11}$ is halogen, $C_1$-$C_3$ alkyl or $C_1$-$C_3$ haloalkyl;
$R^{20}$ is halogen, $C_1$-$C_3$ alkyl or $C_1$-$C_3$ haloalkyl;
$R^{21}$ is H, $C_1$-$C_2$ alkyl or $C_1$-$C_2$ haloalkyl;
$R^{22}$ is H, halogen, $C_1$-$C_3$ alkyl, $C_1$-$C_3$ haloalkyl or $C_1$-$C_3$ alkylthio;
$R^{23}$ is H, halogen, $C_1$-$C_3$ alkyl or $C_1$-$C_3$ haloalkyl;
$R^{24}$ is H, halogen, $C_1$-$C_3$ alkyl or $C_1$-$C_3$ haloalkyl;
$R^{25}$ is H, $C_1$-$C_3$ alkyl or $C_1$-$C_3$ haloalkyl;
m is 0, 1 or 2;
n is 0, 1, 2 or 3;
$R^{12a}$ and $R^{12b}$ are each independently H, $C_1$-$C_2$ alkyl or $C_1$-$C_2$ haloalkyl; or
$R^{12a}$ and $R^{12b}$ are taken together as $C_2$-$C_5$ alkanediyl;
$R^{13a}$ is H, halogen, $C_1$-$C_2$ alkyl, $C_1$-$C_2$ haloalkyl, $C_1$-$C_2$ alkoxy, $C_1$-$C_2$ haloalkoxy, $C_1$-$C_2$ alkylthio or $C_1$-$C_2$ alkoxyamino;
$R^{13b}$ is H, halogen, $C_1$-$C_2$ alkyl or $C_1$-$C_2$ haloalkyl; or
$R^{13a}$ and $R^{13b}$ are taken together as $C_2$-$C_5$ alkanediyl;
Q is a 5-membered unsaturated or partially unsaturated heterocyclic ring containing ring members selected from carbon atoms and up to 4 heteroatoms independently selected from up to 1 O, up to 1 S and up to 4 N atoms, wherein up to 2 carbon atom ring members are independently selected from C(=O), the heterocyclic ring optionally substituted with one substituent on a ring member distal relative to the ring member connecting the heteroaromatic ring to the remainder of Formula 1, said optional substituent selected from $R^{14c}$ on carbon atom ring members and from $R^{14n}$ on nitrogen atom ring members, the heterocyclic ring further optionally substituted with substituents selected from $R^{15c}$ on carbon atom ring members and $R^{15n}$ on nitrogen atom ring members;
each $R^{14c}$ is independently halogen, cyano, $C_1$-$C_3$ alkyl, $C_1$-$C_3$ haloalkyl, $C_1$-$C_3$ alkoxy, $C_1$-$C_3$ haloalkoxy, $C_2$-$C_3$ alkoxycarbonyl or $C_2$-$C_3$ alkylcarbonyl; or a phenyl ring optionally substituted with up to 5 substituents independently selected from $R^{16}$; or a heteroaromatic ring optionally substituted with up to 4 substituents independently selected from $R^{17c}$ on carbon atom ring members and from $R^{17n}$ on nitrogen atom ring members; or
two $R^{14c}$ bonded to adjacent carbon atoms are taken together with carbon atom ring members to form a 5- or 6-membered carbocyclic or partially aromatic ring, the ring optionally substituted with halogen or $C_1$-$C_4$ alkyl;
each $R^{14n}$ is independently $C_1$-$C_3$ alkyl, $C_1$-$C_3$ haloalkyl or $C_1$-$C_3$ alkoxy; or a phenyl ring optionally substituted with up to 5 substituents independently selected from $R^{18}$; or a heteroaromatic ring optionally substituted with up to 4 substituents independently selected from $R^{19c}$ on carbon atom ring members and from $R^{19n}$ on nitrogen atom ring members;
each $R^{15c}$ is independently halogen, $C_1$-$C_3$ alkyl, $C_1$-$C_3$ haloalkyl or $C_1$-$C_3$ alkoxy;
each $R^{15n}$ is independently $C_1$-$C_3$ alkyl, $C_1$-$C_3$ haloalkyl or $C_1$-$C_3$ alkoxy;
each $R^{16}$, $R^{17c}$, $R^{18}$ and $R^{19c}$ is independently halogen, cyano, $C_1$-$C_2$ alkyl, $C_1$-$C_2$ haloalkyl, $C_1$-$C_2$ alkoxy or $C_1$-$C_2$ haloalkoxy; and
each $R^{17n}$ and $R^{19n}$ is independently $C_1$-$C_2$ alkyl, $C_1$-$C_2$ haloalkyl or $C_1$-$C_2$ alkoxy.

More particularly, this invention pertains to a compound of Formula 1 (including all stereoisomers), an N-oxide or a salt thereof.

This invention also relates to a fungicidal composition comprising (a) a compound of the invention (i.e. in a fungicidally effective amount); and (b) at least one additional component selected from the group consisting of surfactants, solid diluents and liquid diluents.

This invention also relates to a fungicidal composition comprising (a) a compound of the invention; and (b) at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds. As referred to herein, the term "seedling", used either alone or in a combination of words means a young plant developing from the embryo of a seed.

As referred to in this disclosure, the terms "fungal pathogen" and "fungal plant pathogen" include pathogens in the Ascomycota, Basidiomycota and Zygomycota phyla, and the fungal-like Oomycota class that are the causal agents of a broad spectrum of plant diseases of economic importance, affecting ornamental, turf, vegetable, field, cereal and fruit crops. In the context of this disclosure, "protecting a plant from disease" or "control of a plant disease" includes preventative action (interruption of the fungal cycle of infection, colonization, symptom development and spore production) and/or curative action (inhibition of colonization of plant host tissues).

As referred to in this disclosure, the term mode of action (MOA) is as defined broadly by the Fungicide Resistance Action Committee (FRAC), and is used to distinguish fungicide groups according to their biochemical mode of action in the biosynthetic pathways of plant pathogens. These FRAC-defined MOAs are (A) nucleic acid synthesis, (B) mitosis and cell division, (C) respiration, (D) amino acid and protein synthesis, (E) signal transduction, (F) lipid synthesis and membrane integrity, (G) sterol biosynthesis in membranes, (H) cell wall biosynthesis in membranes, (I) melanin synthesis in cell wall, (P) host plant defense induction, multi-site contact activity and unknown mode of action. Each MOA class consists of one or more groups based either on individual validated target sites of action, or in cases where the precise target site is unknown, based on cross resistance profiles within a group or in relation to other groups. Each of these groupings within a FRAC-defined MOA, whether the target site is known or unknown, is designated by a FRAC code. Additional information on target sites and FRAC codes can be obtained from publicly available databases maintained, for example, by FRAC.

As referred to in this disclosure, the term "cross resistance" refers to a phenomenon wherein a pathogen evolves resistance to one fungicide and in addition acquires resistance to others. These additional fungicides are typically, but not always, in the same chemical class or have the same target site of action, or can be detoxified by the same mechanism.

In the above recitations, the term "alkyl", used either alone or in compound words such as "alkylthio" or "haloalkyl" includes straight-chain or branched alkyl such as methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" also includes moieties comprised of multiple triple bonds such as 2,5-hexadiynyl. "Alkanediyl", also known as "alkylene", denotes a straight-chain or branched alkane divalent radicals. Examples of "alkylene" or "alkanediyl" include $CH_2$, $CH_2CH_2$, $CH(CH_3)$, $CH_2CH_2CH_2$, $CH_2CH(CH_3)$, and the different butylene isomers. The alkanediyl, in the context of $R^{12a}$ and $R^{12b}$ taken together, is bonded through the same carbon atom to the remainder of the molecule. Likewise, in the context of $R^{13a}$ and $R^{13b}$ taken together, the alkanediyl is bonded through the same carbon atom to the remainder of the molecule. "Alkenylene" denotes a straight-chain or branched alkenediyl containing one olefinic bond. Examples of "alkenylene" include $CH=CH$, $CH_2CH=CH$, $CH=C(CH_3)$ and the different butenylene isomers. "Alkynylene" denotes a straight-chain or branched alkynediyl containing one triple bond. Examples of "alkynylene" include $—C≡C—$, $—CH_2C≡C—$, $—C≡CCH_2—$, and the different butynylene isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC≡CCH_2O$, $CH_3C≡CCH_2O$ and $CH_3C≡CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group.

Examples of "alkylsulfinyl" include $CH_3S(O)—$, $CH_3CH_2(O)—$, $CH_3CH_2CH_2S(O)—$, $(CH_3)_2CHS(O)—$ and the different butylsulfinyl, pentylsulfinyl and hexylsulfinyl isomers. Examples of "alkylsulfonyl" include $CH_3S(O)_2—$, $CH_3CH_2S(O)_2—$, $CH_3CH_2CH_2S(O)_2—$, $(CH_3)_2CHS(O)_2—$, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylthioalkoxy" denotes alkylthio substitution on alkoxy. "Alkyldithio" denotes branched or straight-chain alkyldithio moieties. Examples of "alkyldithio" include $CH_3SS—$, $CH_3CH_2SS—$, $CH_3CH_2CH_2SS—$, $(CH_3)_2CHSS—$ and the different butyldithio and pentyldithio isomers. "Alkylamino", "dialkylamino", "alkenylthio", "alkenylsulfinyl", "alkenylsulfonyl", "alkynylthio", "alkynylsulfinyl", "alkynylsulfonyl", and the like, are defined analogously to the above examples.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. "Cycloalkylalkoxy" denotes cycloalkylalkyl linked through an oxygen atom attached to the alkyl chain. Examples of "cycloalkylalkoxy" include cyclopropylmethoxy, cyclopentylethoxy, and other cycloalkyl moieties bonded to straight-chain or branched alkoxy groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen", said alkyl may be partially or fully substituted with halogen atoms which may be the same or different. Examples of "haloalkyl" or "alkyl substituted with halogen" include $F_3C—$, $ClCH_2—$, $CF_3CH_2—$ and $CF_3CCl_2—$. The terms "halocycloalkyl", "haloalkoxy", "haloalkylthio", "haloalkenyl", "haloalkynyl", and the like, are defined analogously to the term "haloalkyl". Examples of "haloalkoxy" include $CF_3O—$, $CCl_3CH_2O—$, $HCF_2CH_2CH_2O—$ and $CF_3CH_2O—$. Examples of "haloalkylthio" include $CCl_3S—$, $CF_3S—$, $CCl_3CH_2S—$ and $ClCH_2CH_2CH_2S—$. Examples of "haloalkylsulfinyl" include $CF_3S(O)—$, $CCl_3S(O)—$, $CF_3CH_2S(O)—$ and $CF_3CF_2S(O)—$. Examples of "haloalkylsulfonyl" include $CF_3S(O)_2—$, $CCl_3S(O)_2—$, $CF_3CH_2S(O)_2—$ and $CF_3CF_2S(O)_2—$. Examples of "haloalkenyl" include $(Cl)_2C=CHCH_2—$ and $CF_3CH_2CH=CHCH_2—$. Examples of "haloalkynyl" include $HC≡CCHCl—$, $CF_3C≡C—$, $CCl_3C≡C—$ and $FCH_2C≡CCH_2—$. Examples of "haloalkoxyalkoxy" include $CF_3OCH_2O—$, $ClCH_2CH_2OCH_2CH_2O—$, $Cl_3CCH_2OCH_2O—$ as well as branched alkyl derivatives.

"Alkylcarbonyl" denotes a straight-chain or branched alkyl moieties bonded to a $C(=O)$ moiety. Examples of "alkylcarbonyl" include $CH_3C(=O)—$, $CH_3CH_2CH_2C(=O)—$ and $(CH_3)_2CHC(=O)—$. Examples of "alkoxycarbonyl" include $CH_3OC(=O)—$, $CH_3CH_2OC(=O)—$, $CH_3CH_2CH_2OC(=O)—$, $(CH_3)_2CHOC(=O)—$ and the different butoxy- or pentoxycarbonyl isomers.

The total number of carbon atoms in a substituent group is indicated by the "$C_i$-$C_j$" prefix where i and j are numbers from 1 to 5. For example, $C_1$-$C_3$ alkoxy designates $CH_3O—$, $CH_3CH_2O—$, $CH_3CH_2CH_2O—$ and $(CH_3)_2CHO—$; $C_1$-$C_4$ alkylsulfonyl designates methylsulfonyl through butylsulfonyl; $C_2$ alkoxyalkyl designates $CH_3OCH_2—$; $C_3$ alkoxyalkyl designates, for example, $CH_3CH(OCH_3)—$, $CH_3OCH_2CH_2—$ or $CH_3CH_2OCH_2—$; and $C_4$ alkoxyalkyl designates the various isomers of an alkyl group substituted with an alkoxy group containing a total of four carbon atoms, examples including $CH_3CH_2CH_2OCH_2—$ and $CH_3CH_2OCH_2CH_2—$.

When a compound is substituted with a substituent bearing a subscript that indicates the number of said substituents can exceed 1, said substituents (when they exceed 1) are independently selected from the group of defined substituents, e.g., $(R^2)_n$, n is 0, 1, 2 or 3. When a group contains a substituent which can be hydrogen, for example $R^5$, then when this substituent is taken as hydrogen, it is recognized that this is equivalent to said group being unsubstituted. When a variable group is shown to be optionally attached to a position, for example $(R^2)_n$, wherein n may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" or "ring system" as a component of Formula 1 (e.g., Q group) is carbocyclic or heterocyclic. The terms "carbocyclic ring", "carbocycle" or "carbocyclic ring system" denote a ring or ring system wherein the atoms forming the ring backbone are selected only from carbon. The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a carbocyclic ring or heterocyclic ring can be a saturated or unsaturated ring. "Saturated" refers to a ring having a backbone consisting of atoms linked to one another by single bonds; unless otherwise specified, the remaining carbon valences are occupied by hydrogen atoms. Unless otherwise stated, an "unsaturated ring" may be partially unsaturated or fully unsaturated. The expression "fully unsaturated ring" means a ring of atoms in which the bonds between atoms in the ring are single or double bonds according to valence bond theory and furthermore the bonds between atoms in the ring include as many double bonds as possible without double bonds being cumulative (i.e. no $C=C=C$ or $C=C=N$). The term "partially unsaturated ring" denotes a ring comprising at least one ring member bonded to an adjacent ring member through a double bond and which conceptually potentially accommodates a number of non-cumulated double bonds between adjacent ring members (i.e. in its fully unsaturated counterpart form) greater than the number of double bonds present (i.e. in its partially unsaturated form).

Unless otherwise indicated, heterocyclic rings and ring systems can be attached through any available carbon or nitrogen by replacement of a hydrogen atom on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring system" denotes a carbocyclic or heterocyclic ring system in which at least one ring of the ring system is aromatic. When a fully unsaturated carbocyclic ring satisfies Hückel's rule, then said ring is also called an "aromatic ring" or "aromatic carbocyclic ring".

The term "aromatic carbocyclic ring system" denotes a carbocyclic ring system in which at least one ring of the ring system is aromatic. When a fully unsaturated heterocyclic ring satisfies Hückel's rule, then said ring is also called a "heteroaromatic ring" or "aromatic heterocyclic ring". The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" denotes a carbocyclic ring in which no ring in the ring system is aromatic. The term "nonaromatic heterocyclic ring system" denotes a heterocyclic ring system in which no ring in the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other. When a compound is substituted with a substituent bearing a subscript that indicates the number of said substituents can exceed 1, said substituents (when they exceed 1) are independently selected from the group of defined substituents, e.g., $(R^2)_n$ n is 0, 1, 2 or 3. When a group contains a substituent which can be hydrogen, for example, $R^1$, then when this substituent is taken as hydrogen, it is recognized that this is equivalent to said group being unsubstituted. When a variable group is shown to be optionally attached to a position, for example $(R^2)_n$, wherein n may be 0, then hydrogen may be at the position even if not recited in the variable group definition. When one or more positions on a group are said to be "not substituted" or "unsubstituted", then hydrogen atoms are attached to take up any free valency.

As referred to by the present disclosure and claims, an "unsaturated or partially unsaturated heterocyclic ring" is a heterocyclic ring wherein at least two ring member atoms are linked together by a double bond. Unless otherwise stated, an "unsaturated or partially heterocyclic ring" (e.g., substituent Q) may be partially unsaturated or fully unsaturated. The expression "fully unsaturated heterocyclic ring" means a heterocyclic ring of atoms in which the bonds between carbon and/or nitrogen atoms in the ring are single or double bonds according to valence bond theory and furthermore the bonds between carbon and/or nitrogen atoms in the ring include as many double bonds as possible without double bonds being cumulative (i.e. no C=C=C, N=C=C, etc.). The term "partially unsaturated heterocyclic ring" denotes a heterocyclic ring comprising at least one ring member bonded to an adjacent ring member through a double bond and which conceptually potentially accommodates a number of non-cumulated double bonds between adjacent ring members (i.e. in its fully unsaturated counterpart form) greater than the number of double bonds present (i.e. in its partially unsaturated form). When a fully unsaturated heterocyclic ring satisfies Hückel's rule, then said ring is also called a "heteroaromatic ring" or "aromatic heterocyclic ring".

As shown in the Summary of the Invention, G is a radical selected from the group consisting of G-1, G-2, G-3, G-4 and G-5. As depicted in the Summary of the Invention, the bond of the G ring projecting to the left is attached to the remainder of Formula 1 through L. The bond projecting to the lower right side of the G ring represents the attachment point of the Q ring. Note the Q ring resides in a fixed position on the G ring and does not "float" in relation to the attachment point of the G ring to L. Note, however, that the $(R^2)_n$ variable as depicted on the G ring in the Summary of the Invention may "float" around the G ring and may therefore be bonded to any available carbon atoms on the each respective G ring.

In the Summary of the Invention the "unsaturated or partially unsaturated" heterocyclic ring of Q is specified to be 5-membered, with ring members selected from carbon atoms and up to 4 heteroatoms independently selected from up to 1 O, up to 1 S and up to 4 N atoms, wherein up to 2 carbon atoms are independently selected from C(=O). The heterocyclic ring is optionally substituted with one substituent selected from $R^{14c}$ or $R^{14n}$ on one ring member distal relative to the ring member connecting the heteroaromatic ring to the remainder of Formula 1. As depicted in Exhibit 1, in the five-membered heterocyclic ring of Q, a ring member distal relative to the ring member connecting the ring to the remainder of Formula 1 is linked through two ring bonds to the connecting ring member. The heterocyclic ring of Q is further optionally substituted with substituents selected from $R^{15c}$ on carbon atom ring members and $R^{15n}$ on nitrogen atom ring members.

Exhibit 1

Optional $R^{14c}$ or $R^{14n}$ substitution on the Q ring of Formula 1

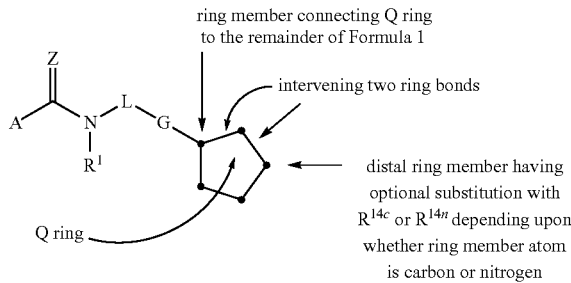

Certain heterocycles forming Q may have two distal ring members available for substitution. In this situation, only one of the distal ring members may be substituted with $R^{14c}$ or $R^{14n}$; the other distal ring member may be substituted with $R^{15c}$ or $R^{15n}$. If neither of the distal ring members of a heterocycle forming Q are available for substitution, then any additional substituents on the heterocycle are selected from $R^{15c}$ or $R^{15n}$. If a distal ring member can have two substituents, one substituent may be selected from $R^{14c}$ or $R^{14n}$ and the other substituent may be selected from $R^{15c}$ or $R^{15n}$. In other words, the Q ring is limited to one $R^{14c}$ or $R^{14n}$ substituent and this substituent must be bonded to a distal ring member; the Q ring can otherwise be further substituted with $R^{15c}$ or $R^{15n}$ on any available ring member.

If an attachment point on a group (e.g., ring) is depicted as floating (e.g., as illustrated by the 5-membered unsaturated or partially unsaturated heterocyclic rings Q-1 through Q-21 in Exhibit 4) the group can be attached to the remainder of Formula 1 through any available carbon or nitrogen of the group by replacement of a hydrogen atom. If the attachment point of a substituent on a group (e.g., ring) is depicted as floating (e.g., as illustrated for $R^{14}$ and $R^{15}$ on the 5-membered unsaturated heterocyclic rings Q-1 through Q-21 in Exhibit 4), the substituent can be attached to any available carbon or nitrogen atom by replacing a hydrogen atom.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

As specified in the Summary of the Invention and elsewhere in the present disclosure, linking group L in Formula 1 can be —C($R^{12a}$)$R^{12b}$—C($R^{13a}$)$R^{13b}$—, wherein the carbon atom bonded to $R^{12a}$ and $R^{12b}$ is also bonded to the carboxamide nitrogen atom in Formula 1. In this context, the carboxamide is an ordinary carboxamide when Z is O or a thiocarboxamide when Z is S.

Also as specified in the Summary of the Invention and elsewhere in the present disclosure, linking group L in Formula 1 can be 1,2-phenylene optionally substituted with up to 4 substituents independently selected from halogen and $C_1$-$C_2$ alkyl. As shown in Exhibit 2, "1,2-phenylene" is understood to refer to a benzene ring that is connected to the remainder of the molecule (e.g., Formula 1) at ortho positions (hence "1,2-") and optionally substituted with halogen and $C_1$-$C_2$ alkyl at the four remaining positions on the ring.

Exhibit 2

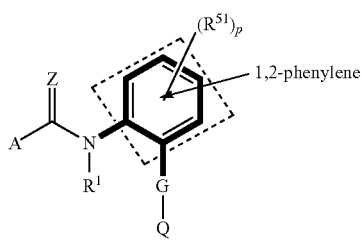

wherein each $R^{51}$ is independently halogen or $C_1$-$C_2$ alkyl, and p is 0, 1, 2, 3 or 4. Linking group L being optionally substituted 1,2-phenylene is further illustrated by the molecular structure depictions associated with Tables 1-1221 and Index Table A.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. For example, when $R^{12b}$ and $R^{13b}$ are both H, and $R^{12a}$ and $R^{13a}$ are other than H, then Formula 1 possesses chiral centers at the carbon atoms to which $R^{12b}$ and $R^{13b}$ are bonded, allowing for two racemic diastereomers, designated as anti and syn. Each racemic diastereomer is comprised of a pair of enantiomers, i.e. the anti diastereomer is comprised of enantiomers 1' and 1", and the syn diastereomer is comprised of enantiomers 2' and 2" as shown below in Exhibit 2, with the chiral centers identified with an asterisk (*).

Exhibit 3

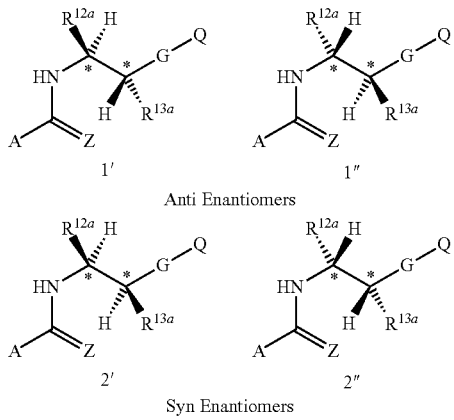

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This invention comprises racemic mixtures, for example, equal amounts of the enantiomers of Formulae 1' and 1". In addition, this invention includes compounds that are enriched compared to the racemic mixture in an enantiomer of Formula 1. Also included are the essentially pure enantiomers of compounds of Formula 1, for example, Formula 1' or Formula 1".

When enantiomerically enriched, one enantiomer is present in greater amounts than the other, and the extent of enrichment can be defined by an expression of enantiomeric excess ("ee"), which is defined as $(2x-1)\cdot 100\%$, where x is the mole fraction of the dominant enantiomer in the mixture (e.g., an ee of 20% corresponds to a 60:40 ratio of enantiomers).

Preferably the compositions of this invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as $R^2$ may themselves contain chiral centers. This invention comprises racemic mixtures as well as enriched and essentially pure stereoconfigurations at these additional chiral centers.

Compounds of this invention can exist as one or more conformational isomers due to restricted rotation about the amide bond (e.g., C(O)—N) in Formula 1. This invention comprises mixtures of conformational isomers. In addition, this invention includes compounds that are enriched in one conformer relative to others.

This invention comprises all stereoisomers, conformational isomers and mixtures thereof in all proportions as well as isotopic forms such as deuterated compounds.

One skilled in the art will appreciate that not all nitrogen containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Compounds selected from Formula 1, stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

Embodiments of the present invention as described in the Summary of the Invention include (where Formula 1 as used in the following Embodiments includes N-oxides and salts thereof):

Embodiment 1

A compound of Formula 1 wherein A is selected from the group consisting of A-1, A-2, A-4 and A-8.

Embodiment 2

A compound of Formula 1 or Embodiment 1 wherein A is selected from the group consisting of A-1, A-2 and A-8.

Embodiment 2a

A compound of Formula 1 or Embodiment 1 wherein A is selected from the group consisting of A-1, A-2 and A-4.

Embodiment 3

A compound of Formula 1 or any one of Embodiments 1 through 2a wherein A is selected from the group consisting of A-1 and A-2.

Embodiment 3a

A compound of Formula 1 or any one of Embodiments 1 through 3 wherein A is A-1.

Embodiment 4

A compound of Formula 1 or any one of Embodiments 1 through 3 wherein A is A-2.

Embodiment 5

A compound of Formula 1 wherein A is A-3.

Embodiment 6

A compound of Formula 1 or Embodiment 1 or 2a wherein A is A-4.

Embodiment 7

A compound of Formula 1 wherein A is A-5.

Embodiment 8

A compound of Formula 1 wherein A is A-6.

Embodiment 8a

A compound of Formula 1 or any one of Embodiments 1 through 2 wherein A is A-8.

Embodiment 8b

A compound of Formula 1 wherein A is A-7.

Embodiment 8c

A compound of Formula 1 wherein A is A-9.

Embodiment 8d

A compound of Formula 1 wherein A is A-10.

Embodiment 8e

A compound of Formula 1 wherein A is A-11.

Embodiment 9

A compound of Formula 1 or any one of Embodiments 1 through 8e wherein Z is O.

Embodiment 10

A compound of Formula 1 or any one of Embodiments 1 through 9 wherein G is selected from the group consisting of G-1, G-2, G-3 and G-4.

Embodiment 11

A compound of Formula 1 or any one of Embodiments 1 through 9 wherein G is selected from the group consisting of G-2, G-4 and G-5.

Embodiment 12

A compound of Formula 1 or any one of Embodiments 1 through 10 wherein G is selected from the group consisting of G-1 and G-4.

Embodiment 13

A compound of Formula 1 or any one of Embodiments 1 through 10 wherein G is selected from the group consisting of G-1, G-2 and G-3.

Embodiment 14

A compound of any one of Embodiments 1 through 10 or 12 through 13 wherein G is G-1.

Embodiment 15

A compound of Formula 1 or any one of Embodiments 1 through 3a or 9 through 14 wherein $B^1$ is CH.

Embodiment 16

A compound of Formula 1 or any one of Embodiments 1 through 3a or 9 through 14 wherein $B^1$ is N.

Embodiment 17

A compound of Formula 1 or any one of Embodiments 1 through 3a or 9 through 16 wherein $B^2$ is CH.

Embodiment 18

A compound of Formula 1 or any one of Embodiments 1 through 3a or 9 through 16 wherein $B^2$ is N.

Embodiment 18a

A compound of Formula 1 or any one of Embodiments 1 through 3a or 9 through 18 wherein $B^3$ is N, provided at least one of $B^1$ and $B^2$ is CH;

Embodiment 18b

A compound of Formula 1 or any one of Embodiments 1 through 3a or 9 through 18 wherein $B^3$ is CH;

Embodiment 19

A compound of Formula 1 or any one of Embodiments 1 through 3a or 9 through 18b wherein $R^3$ is halogen, $C_1$-$C_2$ alkyl or $C_1$-$C_2$ haloalkyl.

Embodiment 20

A compound of Embodiment 19 wherein $R^3$ is halogen, $CH_3$ or $C_1$ haloalkyl.

Embodiment 20a

A compound of Embodiment 20 wherein $R^3$ is halogen.

Embodiment 21

A compound of Embodiment 20 wherein $R^3$ is F, Cl, Br, $CH_3$, $CHF_2$ or $CF_3$.

Embodiment 21a

A compound of Embodiment 20 wherein $R^3$ is F, Cl, or Br.

Embodiment 22

A compound of Embodiment 21 wherein $R^3$ is $CF_3$.

Embodiment 23

A compound of Formula 1 or any one of Embodiments 1 through 3, 4 or 9 through 14 wherein $R^4$ is halogen, $C_1$-$C_2$ alkyl or $C_1$-$C_2$ haloalkyl.

Embodiment 24

A compound of Embodiment 23 wherein $R^4$ is halogen, $CH_3$ or $C_1$ haloalkyl.

Embodiment 25

A compound of Embodiment 24 wherein $R^4$ is F, Cl, Br, $CH_3$, $CHF_2$ or $CF_3$.

Embodiment 26

A compound of Embodiment 25 wherein $R^4$ is $CHF_2$.

Embodiment 27

A compound of Formula 1 or any one of Embodiments 1 through 3, 4, 9 through 14 or 23 through 26 wherein $R^5$ is H, halogen, $C_1$-$C_2$ alkyl or $C_1$-$C_2$ haloalkyl.

Embodiment 28

A compound of Embodiment 27 wherein $R^5$ is H, halogen, $CH_3$ or $C_1$ haloalkyl.

Embodiment 29

A compound of Embodiment 28 wherein $R^5$ is H, F, Cl, Br, $CH_3$, $CHF_2$ or $CF_3$.

Embodiment 30

A compound of Embodiment 29 wherein $R^5$ is H.

Embodiment 31

A compound of Formula 1 or any one of Embodiments 1 through 3, 4, 9 through 14 or 23 through 30 wherein $R^6$ is $CH_3$.

Embodiment 32

A compound of Formula 1 or any one of Embodiments 5 or 9 through 14 wherein $R^7$ is halogen, $C_1$-$C_2$ alkyl or $C_1$-$C_2$ haloalkyl.

Embodiment 33

A compound of Embodiment 32 wherein $R^7$ is halogen, $CH_3$ or $C_1$ haloalkyl.

Embodiment 34

A compound of Embodiment 33 wherein $R^7$ is F, Cl, Br, $CH_3$, $CHF_2$ or $CF_3$.

Embodiment 35

A compound of Formula 1 or any one of Embodiments 5, 9 through 14 or 32 through 34 wherein $R^8$ is H or $CH_3$.

Embodiment 36

A compound of Formula 1 or any one of Embodiments 1, 6 or 9 through 14 wherein $R^{9a}$ is halogen, $C_1$-$C_2$ alkyl, $C_1$-$C_2$ haloalkyl or $C_1$-$C_2$ alkylthio.

Embodiment 36a

A compound of Embodiment 36 wherein $R^{9a}$ is halogen, $C_1$-$C_2$ alkyl or $C_1$-$C_2$ haloalkyl.

Embodiment 37

A compound of Embodiment 36a wherein $R^{9a}$ is halogen, $CH_3$ or $C_1$ haloalkyl.

Embodiment 38

A compound of Embodiment 37 wherein $R^{9a}$ is F, Cl, Br, $CHF_2$ or $CF_3$.

Embodiment 38a

A compound of Formula 1 or any one of Embodiments 1, 2a, 6, 9 through 14 or 36 through 38 wherein $R^{9b}$ is H, halogen, $C_1$-$C_2$ alkyl or $C_1$-$C_2$ haloalkyl.

Embodiment 38b

A compound of Embodiment 38a wherein $R^{9b}$ is H, halogen, $C_1$-$C_2$ alkyl.

Embodiment 38c

A compound of Embodiment 38b wherein $R^{9b}$ is H or methyl.

Embodiment 38d

A compound of Embodiment 38b wherein $R^{9b}$ is H.

Embodiment 39

A compound of Formula 1 or any one of Embodiments 7 or 9 through 14 wherein $R^{10}$ is halogen, $C_1$-$C_2$ alkyl or $C_1$-$C_2$ haloalkyl.

Embodiment 40

A compound of Embodiment 39 wherein $R^{10}$ is halogen, $CH_3$ or $C_1$ haloalkyl.

Embodiment 41

A compound of Embodiment 40 wherein $R^{10}$ is F, Cl, Br, $CH_3$, $CHF_2$ or $CF_3$.

Embodiment 42

A compound of Formula 1 or any one of Embodiments 8 or 9 through 14 wherein $R^{11}$ is halogen, $C_1$-$C_2$ alkyl or $C_1$-$C_2$ haloalkyl.

Embodiment 43

A compound of Embodiment 42 wherein $R^{11}$ is halogen, $CH_3$ or $C_1$ haloalkyl.

Embodiment 44

A compound of Embodiment 43 wherein $R^{11}$ is F, Cl, Br, $CH_3$, $CHF_2$ or $CF_3$.

Embodiment 44a

A compound of Formula 1 or any one of Embodiments 1, 2, 8a or 9 through 14 wherein $R^{20}$ is Cl, $CH_3$ or $CF_3$.

Embodiment 44b

A compound of Embodiment 44a wherein $R^{20}$ is $CH_3$ or $CF_3$.

Embodiment 44c

A compound of Formula 1 or any one of Embodiments 1, 2, 8a, 9 through 14, 44a or 44b wherein $R^{21}$ is H or $CH_3$.

Embodiment 44d

A compound of Embodiment 44c wherein $R^{21}$ is H.

Embodiment 44e

A compound of Formula 1 or any one of Embodiments 8b or 9 through 14 wherein $R^{22}$ is F, Cl, $CH_3$ or $CF_3$.

Embodiment 44f

A compound of Embodiment 44e wherein $R^{22}$ is F, Cl or $CF_3$.

Embodiment 44g

A compound of Formula 1 or any one of Embodiments 8c or 9 through 14 wherein $R^{23}$ is H, halogen, $C_1$-$C_2$ alkyl or $C_1$-$C_2$ haloalkyl.

Embodiment 44h

A compound of Embodiment 44g wherein $R^{23}$ is halogen.

Embodiment 44i

A compound of Embodiment 44h wherein $R^{23}$ is Br.

Embodiment 44j

A compound of Embodiment 44g wherein $R^{23}$ is $C_1$-$C_2$ alkyl.

Embodiment 44k

A compound of Embodiment 44g wherein $R^{23}$ is methyl.

Embodiment 44l

A compound of Formula 1 or any one of Embodiments 8d or 9 through 14 wherein $R^{24}$ is H or $C_1$-$C_2$ alkyl,

Embodiment 44m

A compound of Embodiment 44l wherein $R^{24}$ is H.

Embodiment 44n

A compound of Embodiment 44l wherein $R^{24}$ is methyl.

Embodiment 44o

A compound of Formula 1 or any one of Embodiments 8e or 9 through 14 wherein $R^{25}$ is $C_1$-$C_2$ alkyl or cyclopropyl,

Embodiment 44p

A compound of Embodiment 44o wherein $R^{25}$ is methyl.

Embodiment 45

A compound of Formula 1 or any one of Embodiments 1 through 44p wherein $R^1$ is H or cyclopropyl.

Embodiment 46

A compound of Embodiment 45 wherein $R^1$ is H.

Embodiment 47

A compound of Formula 1 or any one of Embodiments 1 through 46 wherein L is —$C(R^{12a})R^{12b}$—$C(R^{13a})R^{13b}$—; or 1,2-phenylene optionally substituted with up to 2 substituents independently selected from F, Cl, Br and $CH_3$.

Embodiment 48

A compound of any one of Embodiments 1 through 47 wherein L is —$C(R^{12a})R^{12b}$—$C(R^{13a})R^{13b}$—.

Embodiment 49

A compound of Formula 1 or any one of Embodiments 1 through 48 wherein $R^{12a}$ is H or $CH_3$.

Embodiment 50

A compound of Embodiment 49 wherein $R^{12a}$ is H.

Embodiment 51

A compound of Formula 1 or any one of Embodiments 1 through 50 wherein $R^{12b}$ is H or $CH_3$.

Embodiment 52

A compound of Embodiment 51 wherein $R^{12b}$ is H.

Embodiment 53

A compound of Formula 1 or any one of Embodiments 1 through 48 wherein when $R^{12a}$ and $R^{12b}$ are taken together, they are taken together as $C_2$ or $C_3$ alkanediyl.

Embodiment 54

A compound of Embodiment 53 wherein $R^{12a}$ and $R^{12b}$ are taken together as $C_2$ alkanediyl (i.e. $R^{12a}$ and $R^{12b}$ are taken together along with the carbon to which they are attached to form a cyclopropyl ring).

Embodiment 55

A compound of Formula 1 or any one of Embodiments 1 through 54 wherein $R^{13a}$ is H, $CH_3$ or $OCH_3$.

Embodiment 56

A compound of Embodiment 55 wherein $R^{13a}$ is H or $CH_3$.

Embodiment 57

A compound of Embodiment 56 wherein $R^{13a}$ is H.

Embodiment 58

A compound of Formula 1 or any one of Embodiments 1 through 57 wherein $R^{13b}$ is H or $CH_3$.

Embodiment 59

A compound of Embodiment 58 wherein $R^{13b}$ is H.

Embodiment 60

A compound of Formula 1 or any one of Embodiments 1 through 54 wherein when $R^{13a}$ and $R^{13b}$ are taken together, they are taken together as $C_2$ or $C_3$ alkanediyl.

Embodiment 61

A compound of Embodiment 60 wherein $R^{13a}$ and $R^{13b}$ are taken together as $C_2$ alkanediyl (i.e. $R^{13a}$ and $R^{13b}$ are taken together along with the carbon to which they are attached to form a cyclopropyl ring).

Embodiment 62

A compound of Formula 1 or any one of Embodiments 1 through 47 wherein when L comprises 1,2-phenylene, said 1,2-phenylene is optionally substituted with up to 2 substituents independently selected from F, Cl, Br and $CH_3$.

Embodiment 63

A compound of Embodiment 62 wherein when L comprises 1,2-phenylene, said 1,2-phenylene is optionally substituted with up to 2 substituents independently selected from F and $CH_3$.

Embodiment 64

A compound of Embodiment 63 wherein when L comprises 1,2-phenylene, said 1,2-phenylene is unsubstituted (except for the bonds to the remainder of Formula 1).

Embodiment 65

A compound of Formula 1 or any one of Embodiments 1 through 47 or 62 through 64 wherein L comprises 1,2-phenylene.

Embodiment 66

A compound of Formula 1 or any one of Embodiments 1 through 65 wherein each $R^2$ is independently halogen or $C_1$-$C_5$ alkyl.

Embodiment 67

A compound of Embodiment 66 wherein each $R^2$ is independently F, Cl, Br or $CH_3$.

Embodiment 68

A compound of Embodiment 67 wherein each $R^2$ is independently F or Cl.

Embodiment 69

A compound of Embodiment 68 wherein each $R^2$ is independently F.

Embodiment 70

A compound of Embodiment 68 wherein each $R^2$ is independently Cl.

Embodiment 71

A compound of Formula 1 or any one of Embodiments 1 through 70 wherein n is 0, 1 or 2.

Embodiment 72

A compound of Embodiment 71 wherein n is 0 or 1.

Embodiment 73

A compound of Formula 1 or any one of Embodiments 1 through 61 wherein when L is —C($R^{12a}$)$R^{12b}$—C($R^{13a}$)$R^{13b}$— and G is selected from G-1 and G-4, then n is 1 and the G ring is substituted with $R^2$ ortho to the bond to L.

Embodiment 74

A compound of Embodiment 73 wherein $R^2$ is Cl.

Embodiment 75

A compound of Formula 1 or any one of Embodiments 1 through 47 or 62 through 71 wherein when L is 1,2-phenylene, G is selected from G-1 and G-4 then n is 1 and the G ring is substituted with one $R^2$ is ortho to the bond to Q.

Embodiment 76

A compound of Embodiment 75 wherein when L is 1,2-phenylene, G is substituted with F ortho to the bond to Q.

Embodiment 77

A compound of Formula 1 or any one of Embodiments 1 through 76 wherein the heterocyclic ring Q contains at least one nitrogen atom ring member.

Embodiment 78

A compound of Embodiment 77 wherein the heterocyclic ring Q contains two nitrogen atom ring members.

Embodiment 79

A compound of Formula 1 or any one of Embodiments 1 through 78 wherein the heterocyclic ring Q is fully unsaturated (i.e. is heteroaromatic).

Embodiment 80

A compound of Formula 1 or any one of Embodiments 1 through 79 wherein the heterocyclic ring Q is selected from furan, thiophene, pyrrole, oxazole, thiazole, imidazole, isoxazole, isothiazole, pyrazole, 1,2,4-oxadiazole, 1,2,5-oxadiazole, 1,3,4-oxadiazole, 1,2,4-thiadiazole, 1,2,5-thiadiazole, 1,3,4-thiadiazole, 1,2,3-triazole, 1,2,4-triazole, tetrazole, 4,5-dihydroisoxazole and 4,5-dihydropyrazole.

Embodiment 81

A compound of Embodiment 80 wherein the heterocyclic ring Q is selected from pyrazole.

Embodiment 82

A compound of Embodiment 80 wherein Q is selected from Q-1 through Q-21 depicted in Exhibit 4

Exhibit 4

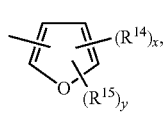  Q-1

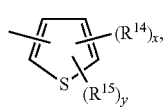  Q-2

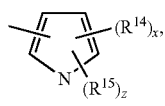  Q-3

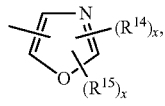  Q-4

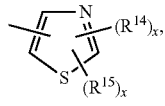  Q-5

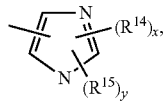  Q-6

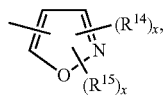  Q-7

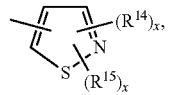  Q-8

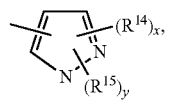  Q-9

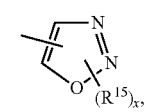  Q-10

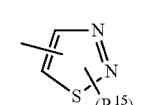  Q-11

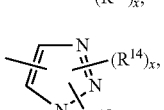  Q-12

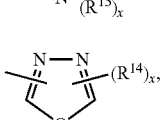  Q-13

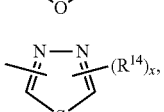  Q-14

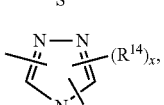  Q-15

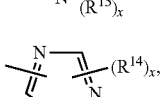  Q-16

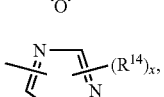  Q-17

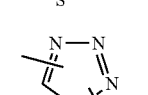  Q-18

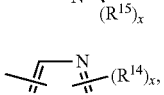  Q-19

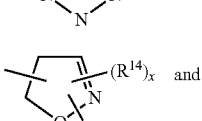  Q-20

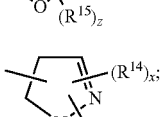  Q-21 wherein $R^{14}$ is bonded to a ring member distal relative to the ring member connecting the Q ring to the remainder of Formula 1, and independently selected from $R^{14c}$ on carbon atom ring members and $R^{14n}$ on nitrogen atom ring members;

each $R^{15}$ is independently selected from $R^{15c}$ on carbon atom ring members and $R^{15n}$ on nitrogen atom ring members;

each x is independently 0 or 1;
each y is independently 0, 1 or 2; and
each z is independently 0, 1, 2 or 3.

Embodiment 83

A compound of Embodiment 82 wherein Q is selected from Q-1 through Q-19.

Embodiment 84

A compound of Embodiment 82 wherein Q is selected from

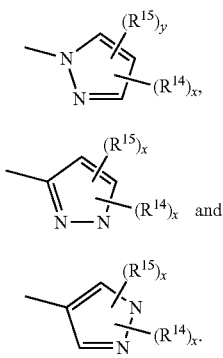

Embodiment 85

A compound of Embodiment 84 wherein Q is selected from Q-9A and Q-9B.

Embodiment 86

A compound of Embodiment 85 wherein Q is Q-9A.

Embodiment 87

A compound of any one of Embodiments 82 through 86 wherein y is 0 or 1.

Embodiment 88

A compound of Formula 1 or any one of Embodiments 1 through 87 wherein each $R^{14c}$ is independently halogen, cyano, $C_1$-$C_2$ alkyl, $C_1$-$C_2$ haloalkyl, $C_1$-$C_2$ alkoxy or $C_1$-$C_2$ haloalkoxy.

Embodiment 89

A compound of Embodiment 88 wherein each $R^{14c}$ is independently halogen, $CH_3$ or $C_1$ haloalkyl.

Embodiment 90

A compound of Embodiment 89 wherein each $R^{14c}$ is independently F, Cl, Br, $CH_3$, $CHF_2$ or $CF_3$.

Embodiment 91

A compound of Embodiment 90 wherein each $R^{14c}$ is independently $CF_3$.

Embodiment 92

A compound of Formula 1 or any one of Embodiments 1 through 91 wherein each $R^{14n}$ is independently $C_1$-$C_2$ alkyl or $C_1$-$C_2$ haloalkyl.

Embodiment 93

A compound of Embodiment 92 wherein each $R^{14n}$ is $C_1$-$C_2$ alkyl.

Embodiment 94

A compound of Embodiment 93 wherein each $R^{14n}$ is $CH_3$.

Embodiment 95

A compound of Formula 1 or any one of Embodiments 1 through 94 wherein each $R^{15c}$ is independently halogen, $C_1$-$C_2$ alkyl, $C_1$-$C_2$ haloalkyl or $C_1$-$C_2$ alkoxy.

Embodiment 96

A compound of Embodiment 95 wherein each $R^{15c}$ is independently halogen, $CH_3$ or $C_1$ haloalkyl.

Embodiment 97

A compound of Embodiment 96 wherein each $R^{15c}$ is independently F, Cl, Br, $CH_3$, $CHF_2$ or $CF_3$.

Embodiment 98

A compound of Formula 1 or any one of Embodiments 1 through 97 wherein each $R^{15n}$ is independently $C_1$-$C_2$ alkyl or $C_1$-$C_2$ haloalkyl.

Embodiment 99

A compound of Embodiment 98 wherein each $R^{15n}$ is $C_1$-$C_2$ alkyl.

Embodiment 100

A compound of Embodiment 99 wherein each $R^{15n}$ is $CH_3$.

Embodiment 101

A compound of Formula 1 or any one of Embodiments 1 through 100 wherein each $R^{16}$, $R^{17c}$, $R^{18}$ and $R^{19c}$ is independently halogen, $C_1$-$C_2$ alkyl, $C_1$-$C_2$ haloalkyl or $C_1$-$C_2$ alkoxy.

Embodiment 102

A compound of Embodiment 101 wherein each $R^{16}$, $R^{17c}$, $R^{18}$ and $R^{19c}$ is independently halogen, $CH_3$ or $C_1$ haloalkyl.

Embodiment 103

A compound of Embodiment 102 wherein each $R^{16}$, $R^{17c}$, $R^{18}$ and $R^{19c}$ is independently F, Cl, Br, $CH_3$, $CHF_2$ or $CF_3$.

Embodiment 104

A compound of Formula 1 or any one of Embodiments 1 through 103, wherein each $R^{17n}$ and $R^{19n}$ is independently $C_1$-$C_2$ alkyl or $C_1$-$C_2$ haloalkyl.

Embodiment 105

A compound of Embodiment 104 wherein each $R^{17n}$ and $R^{19n}$ is independently $C_1$-$C_2$ alkyl.

Embodiment 106

A compound of Embodiment 105 wherein each $R^{17n}$ and $R^{19n}$ is $CH_3$.

Embodiments of this invention, including Embodiments 1-106 above as well as any other embodiments described herein, can be combined in any manner, and the descriptions of variables in the embodiments pertain not only to the compounds of Formula 1, but also to the starting compounds and intermediate compounds useful for preparing the compounds of Formula 1. In addition, embodiments of this invention, including Embodiments 1-106 above as well as any other embodiments described herein, and any combination thereof, pertain to the compositions and methods of the present invention.

Combinations of Embodiments 1-106 are illustrated by:

Embodiment A

A compound of Formula 1 wherein
Z is O;
L is —$C(R^{12a})R^{12b}$—$C(R^{13a})R^{13b}$—; or 1,2-phenylene optionally substituted with up to 2 substituents independently selected from F, Cl, Br and $CH_3$;
G is selected from the group consisting of G-1, G-2, G-3 and G-4;
each $R^2$ is independently halogen or $C_1$-$C_5$ alkyl;
n is 0, 1 or 2;
$R^3$ is halogen, $C_1$-$C_2$ alkyl or $C_1$-$C_2$ haloalkyl;
$R^4$ is halogen, $C_1$-$C_2$ alkyl or $C_1$-$C_2$ haloalkyl;
$R^5$ is H, halogen, $C_1$-$C_2$ alkyl or $C_1$-$C_2$ haloalkyl;
$R^6$ is $CH_3$;
$R^7$ is halogen, $C_1$-$C_2$ alkyl or $C_1$-$C_2$ haloalkyl;
$R^8$ is H or $CH_3$;
$R^{9a}$ is halogen, $C_1$-$C_2$ alkyl, $C_1$-$C_2$ haloalkyl or $C_1$-$C_2$ alkylthio;
$R^{9b}$ is H, halogen or $C_1$-$C_2$ alkyl;
$R^{10}$ is halogen, $C_1$-$C_2$ alkyl or $C_1$-$C_2$ haloalkyl;
$R^{11}$ is halogen, $C_1$-$C_2$ alkyl or $C_1$-$C_2$ haloalkyl;
$R^{22}$ is F, Cl, $CH_3$ or $CF_3$;
$R^{12a}$ is H or $CH_3$;
$R^{12b}$ is H or $CH_3$; or
$R^{12a}$ and $R^{12b}$ are taken as $C_2$ or $C_3$ alkanediyl;
$R^{13a}$ is H, $CH_3$, or $OCH_3$;
$R^{13b}$ is H or $CH_3$; or
$R^{13a}$ and $R^{13b}$ are taken together as $C_2$ or $C_3$ alkanediyl;
Q is Q-1 through Q-21 (as depicted in Embodiment 82);
each $R^{16}$, $R^{17c}$, $R^{18}$ and $R^{19c}$ is independently F, Cl, Br, $CH_3$, $CHF_2$ or $CF_3$; and
each $R^{17n}$ and $R^{19n}$ is $CH_3$.

Embodiment B

A compound of Embodiment A wherein
A is selected from the group consisting of A-1, A-2, A-4 and A-8;
L is —$C(R^{12a})R^{12b}$—$C(R^{13a})R^{13b}$—;
G is selected from the group consisting of G-1 and G-4;
$B^1$ is CH;
each $R^2$ is independently H, F, Cl, Br or $CH_3$;
n is 0 or 1;
$R^3$ is F, Cl, Br, $CH_3$, $CHF_2$ or $CF_3$;
$R^4$ is F, Cl, Br, $CH_3$, $CHF_2$ or $CF_3$;
$R^5$ is H, halogen, $CH_3$ or $C_1$ haloalkyl;
$R^6$ is $CH_3$;
$R^{9a}$ is halogen, F, Cl, Br, $CHF_2$ or $CF_3$;
$R^{9b}$ is H, halogen or $C_1$-$C_2$ alkyl;
$R^{20}$ is Cl, $CH_3$ or $CF_3$;
$R^{21}$ is H or $CH_3$;
$R^{14c}$ is independently F, Cl, Br, $CH_3$, $CHF_2$ or $CF_3$;
Q is selected from Q-9A, Q-9B and Q-9C (as depicted in Embodiment 84);
each $R^{14n}$ is $CH_3$;
each $R^{15c}$ is independently F, Cl, Br, $CH_3$, $CHF_2$ or $CF_3$; and
each $R^{15n}$ is $CH_3$.

Embodiment C

A compound of Embodiment B wherein
A is selected from the group consisting of A-1, A-2 and A-8;
$B^2$ is N;
$B^3$ is CH;
$R^1$ is H;
G is G-1 substituted with at least one $R^2$ ortho to the bond to Q;
each $R^2$ is independently F or Cl;
Q is selected from Q-9A and Q-9B;
$R^3$ is $CF_3$;
$R^4$ is $CHF_2$;
$R^5$ is H, F, Cl, Br, $CH_3$, $CHF_2$ or $CF_3$;
$R^{20}$ is $CH_3$ or $CF_3$;
$R^{21}$ is H;
$R^{12a}$ is H;
$R^{12b}$ is H;
$R^{13a}$ is H or $CH_3$; and
$R^{13b}$ is H.

Embodiment D

A compound of Embodiment A wherein
A is selected from the group consisting of A-1, A-2 and A-4;
L is 1,2-phenylene optionally substituted with up to 2 substituents independently selected from F, Cl, Br and $CH_3$;
G is selected from G-1, G-2 and G-3;
each $R^2$ is independently F, Cl, Br or $CH_3$;
n is 0 or 1;
$R^3$ is F, Cl, Br, $CH_3$, $CHF_2$ or CF;
$R^4$ is F, Cl, Br, $CH_3$, $CHF_2$ or $CF_3$;
$R^5$ is H, halogen, $CH_3$ or $C_1$ haloalkyl;
$R^6$ is $CH_3$;
$R^{9a}$ is halogen, F, Cl, Br, $CHF_2$ or $CF_3$;
$R^{9b}$ is H or methyl;
Q is selected from Q-9A, Q-9B and Q-9C (as depicted in Embodiment 84);

$R^{14c}$ is independently F, Cl, Br, CH$_3$, CHF$_2$ or CF$_3$;
each $R^{14n}$ is CH$_3$;
each $R^{15c}$ is independently F, Cl, Br, CH$_3$, CHF$_2$ or CF$_3$; and
each $R^{15n}$ is CH$_3$.

Embodiment E

A compound of Embodiment D wherein
A is selected from the group consisting of A-1 and A-2;
L is 1,2-phenylene optionally substituted with up to 2 substituents independently selected from F and CH$_3$;
B$^1$ is CH;
B$^3$ is CH;
G is G-1;
each R$^2$ is independently F or Cl;
R$^3$ is CF$_3$;
R$^4$ is CHF$_2$;
R$^5$ is H, F, Cl, Br, CH$_3$, CHF$_2$ or CF$_3$; and
Q is selected from Q-9A and Q-9B.

Embodiment F

A compound of Embodiment E wherein
A is A-1;
L is 1,2-phenylene;
B$^2$ is N;
G is substituted with at least one R$^2$ ortho to the bond in Formula 1 bonded to the bond with Q;
each R$^2$ is independently F or Cl; and
Q is Q-9A.

Specific embodiments include compounds of Formula 1 selected from the group consisting of:
3-(difluoromethyl)-N-[2-[5-fluoro-6-[3-(trifluoromethyl)-1H-pyrazol-1-yl]-3-pyridinyl]phenyl]-1-methyl-1H-pyrazole-4-carboxamide (Compound 68);
3-(difluoromethyl)-1-methyl-N-[2-[2-[3-(trifluoromethyl)-1H-pyrazol-1-yl]-5-pyrimidinyl]phenyl]-1H-pyrazole-4-carboxamide (Compound 58);
3-(difluoromethyl)-1-methyl-N-[2-[6-[3-(trifluoromethyl)-1H-pyrazol-1-yl]-3-pyridazinyl]phenyl]-1H-pyrazole-4-carboxamide (Compound 54);
3-(difluoromethyl)-1-methyl-N-[2-[5-[3-(trifluoromethyl)-1H-pyrazol-1-yl]-2-pyrazinyl]phenyl]-1H-pyrazole-4-carboxamide (Compound 2);
3-(difluoromethyl)-1-methyl-N-[1-methyl-2-[6-[3-(trifluoromethyl)-1H-pyrazol-1-yl]-3-pyridinyl]ethyl]-1H-pyrazole-4-carboxamide (Compound 83); and
N-[1-methyl-2-[6-[3-(trifluoromethyl)-1H-pyrazol-1-yl]-3-pyridinyl]ethyl]-3-(trifluoromethyl)-2-pyridinecarboxamide (Compound 84).

Specific embodiments also include compounds of Formula 1 selected from the group consisting of:
3-(difluoromethyl)-N-[2-[6-[3-(trifluoromethyl)-1H-pyrazol-1-yl]-3-pyridinyl]phenyl]-1-methyl-1H-pyrazole-4-carboxamide (Compound 51);
N-[2-[5-chloro-6-[3-(trifluoromethyl)-1H-pyrazol-1-yl]-3-pyridinyl]phenyl]-3-(trifluoromethyl)-2-pyridinecarboxamide (Compound 34);
N-[2-[5-fluoro-6-[3-(trifluoromethyl)-1H-pyrazol-1-yl]-3-pyridinyl]phenyl]-3-(trifluoromethyl)-2-pyridinecarboxamide (Compound 50);
N-[2-[5-chloro-6-[3-(trifluoromethyl)-1H-pyrazol-1-yl]-3-pyridinyl]phenyl]-3-iodo-2-thiophenecarboxamide (Compound 169);
N-[2-[5-fluoro-6-[3-(trifluoromethyl)-1H-pyrazol-1-yl]-3-pyridinyl]phenyl]-3-iodo-2-thiophenecarboxamide (Compound 159);
5-bromo-N-[2-[5-chloro-6-[3-(trifluoromethyl)-1H-pyrazol-1-yl]-3-pyridinyl]phenyl]-4-thiazolecarboxamide (Compound 171);
N-[2-[5-chloro-6-[3-(trifluoromethyl)-1H-pyrazol-1-yl]-3-pyridinyl]phenyl]-5-iodo-4-thiazolecarboxamide (Compound 103);
3-bromo-N-[2-[5-chloro-6-[3-(trifluoromethyl)-1H-pyrazol-1-yl]-3-pyridinyl]phenyl]-2-thiophenecarboxamide (Compound 175);
N-[2-[5-chloro-6-[3-(trifluoromethyl)-1H-pyrazol-1-yl]-3-pyridinyl]phenyl]-3-iodo-2-pyridinecarboxamide (Compound 124);
3-bromo-N-[2-[5-chloro-6-[3-(trifluoromethyl)-1H-pyrazol-1-yl]-3-pyridinyl]phenyl]-2-pyridinecarboxamide (Compound 125);
N-[2-[5-chloro-6-[4-chloro-1H-pyrazol-1-yl]-3-pyridinyl]phenyl]-3-(trifluoromethyl)-2-pyridinecarboxamide (Compound 61);
2-(trifluoromethyl)-N-[2-[5-[3-(trifluoromethyl)-1H-pyrazol-1-yl]-2-pyrazinyl]phenyl]benzamide (Compound 1);
3-(trifluoromethyl)-N-[2-[2-[3-(trifluoromethyl)-1H-pyrazol-1-yl]-5-pyrimidinyl]phenyl]-2-pyridinecarboxamide (Compound 56);
N-[2-[5-chloro-6-(1H-pyrazol-1-yl)-3-pyridinyl]phenyl]-3-(trifluoromethyl)-2-pyridinecarboxamide (Compound 186) and
N-[2-[5-bromo-6-[3-(trifluoromethyl)-1H-pyrazol-1-yl]-3-pyridinyl]phenyl]-3-(trifluoromethyl)-2-pyridinecarboxamide (Compound 187).

This invention also provides a fungicidal composition comprising a compound of Formula 1 (including all stereoisomers, N-oxides, and salts thereof), and at least one other fungicide. Of note as embodiments of such compositions are compositions comprising a compound corresponding to any of the compound embodiments described above.

This invention also provides a fungicidal composition comprising a compound of Formula 1 (including all stereoisomers, N-oxides, and salts thereof) (i.e. in a fungicidally effective amount), and at least one additional component selected from the group consisting of surfactants, solid diluents and liquid diluents. Of note as embodiments of such compositions are compositions comprising a compound corresponding to any of the compound embodiments described above.

This invention also provides a method for controlling plant diseases caused by fungal plant pathogens comprising applying to the plant or portion thereof, or to the plant seed, a fungicidally effective amount of a compound of Formula 1 (including all stereoisomers, N-oxides, and salts thereof). Of note as embodiments of such methods are methods comprising applying a fungicidally effective amount of a compound corresponding to any of the compound embodiments describe above. Of particular note are embodiments where the compounds are applied as compositions of this invention.

One or more of the following methods and variations as described in Schemes 1-21 can be used to prepare a compound of Formula 1. The definitions of A, Z, R$^1$, G and Q in the compounds of Formulae 1-27 below are as defined above in the Summary of the Invention unless otherwise noted. Compounds of Formulae 1A, 1B, 1C, 1D, 1E, 1F, 7A, 7B, 9A, 9B, 9C, 9D, 9E, 9F, 13A, 14A, 15A, 16A, 16B, 17A, 24A and 24B are various subsets of the compounds of Formula 1, 7, 9, 13, 14, 15, 16, 17 and 24 respectively and all substituents for Formulae 1A, 1B, 1C, 1D, 1E, 1F, 7A, 7B, 9A, 9B, 9C, 9D, 9E, 9F, 13A, 14A, 15A, 16A, 16B, 17A, 24A and 24B are as defined above for Formula 1.

A compound of Formula 1B (i.e. a subset of a compound of Formula 1 wherein Z is S) can be prepared as illustrated in Scheme 1. Treatment of a precursor of Formula 1A (i.e. a compound of Formula 1 wherein Z is O) with phosphorus pentasulfide or Lawesson's reagent [2,4-Bis-(4-methoxyphenyl)-1,3-dithia-2,4-diphosphetane 2,4-disulfide] in an inert solvent such as dioxane or toluene at temperatures ranging from 0° C. to the reflux temperature of the solvent for 0.1 to 72 h affords a thione of Formula 1B. This type of transformation is well-known in the literature, and is typified by examples in U.S. Pat. No. 3,755,582.

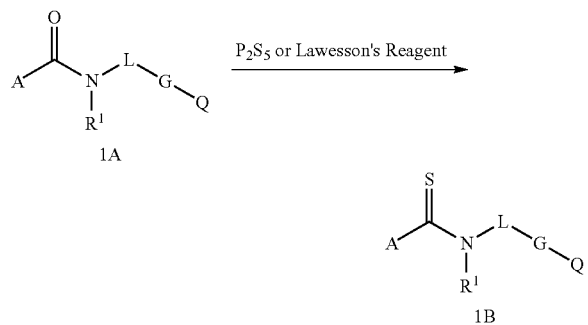

A compound of Formula 1C (i.e. a subset of a compound of Formula 1 wherein Z is O; and Q is an N-linked heterocycle, $Q^N$) and a compound of Formula 1D (i.e. a subset of a compound of Formula 1 wherein Z is O; and Q is a C-linked heterocycle, $Q^C$) can be prepared from the intermediates of a compound of Formula 2 as outlined in Scheme 2 below.

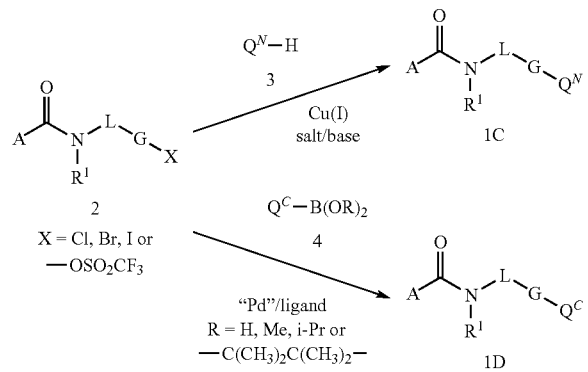

Preparation of a compound of Formula 1C can be achieved via Buchwald-Hartwig coupling of an intermediate of Formula 2 with 1 to 3 eq. of a heterocycle of Formula 3 (wherein H is bonded to a nitrogen atom of the heterocycle) in an inert solvent in the presence of 0.1 to 1.0 eq. of a suitable ligand, 0.1 to 1.0 eq. of a copper(I) salt, and 5 to 10 eq. of a carbonate base. Such transformations are well-documented in the literature (see, for example, *Tetrahedron Letters* 2010, 52(38), 5052 and *J. Med. Chem.* 2010, 53(10), 4248). Typical ligands for the reaction are phenanthroline 1,2-diaminocyclohexane or 1,2-dialkylaminocyclohexane, while CuI and CuBr may be employed as the copper(I) salts. Carbonate bases such as sodium or potassium carbonate can also be used as the base. Suitable solvents for the reaction are dioxane, 1,2-dimethoxyethane or toluene and the reaction is carried out at temperatures ranging from ambient to the reflux temperature of the solvent for times ranging from 1 to 48 h. An amine of Formula 3 is commercially available, or can be readily prepared by the skilled practitioner using well-established protocols. A Compound of Formula 1D in Scheme 2 can be prepared via Suzuki-Miyura coupling of an intermediate of Formula 2 with one or more equivalents of a boron intermediate such as a compound of Formula 4 in the presence of a catalytic amount of palladium(O) with a ligand, or a palladium(II) salt with a ligand as described analogously to commonly-practiced methods disclosed in *Angew. Chem. Int. Ed.* 2006, 45, 3484 and *Tetrahedron Letters* 2002, 58(14), 2885. The reaction can be conducted in solvents selected from diethyl ether, dioxane, tetrahydrofuran and acetonitrile. A base is also present in amounts ranging from 5 to 20 eq. Suitable bases for this transformation include sodium, potassium or cesium carbonate, while palladium(II) salts such as $Pd(OAc)_2$ or $PdCl_2$ are commonly employed in conjunction with ligands such as triphenylphosphine or 1,1'-bis(diphenylphosphino)ferrocene. The reaction is conducted at temperatures ranging from ambient to the reflux temperature of the solvent. A boron intermediate of Formula 4 is either commercially available, or can be prepared easily from the corresponding halides or triflates via known methods disclosed in, for example, WO2007/034278, U.S. Pat. No. 8,080,566, *Org. Lett.* 2011, 13(6), 1366, and *Org. Lett.* 2012, 14(2), 600.

Compounds of Formulae 1C and 1D can alternatively be prepared from boron intermediates of a compound of Formula 5 as shown in Scheme 3 below. Chan-Lam conversion of an intermediate of a compound of Formula 5 to a compound of Formula 1C can be accomplished as described in *Tetrahedron Letters* 1998, 38, 2941, or *Chemistry Letters* 2010, 39(7), 764. An intermediate of Formula 5 is reacted in an inert solvent with 1 to 2 eq. of a heterocyclic amine of Formula 3 (i.e. $Q^N$ is an heterocycle with a free NH available for bonding) and a base in the presence of 1 to 5 eq. of a Cu(II) salt at temperatures ranging from ambient to the reflux temperature of the solvent for 24 to 72 h. Suitable solvents include dichloromethane, chloroform, diethyl ether and tetrahydrofuran. Suitable bases include pyridine, quinoline and triethylamine which can be used in the amount of from 1 to 5 eq. Examples of Cu(II) salts that may be used include $Cu(OAc)_2$, $CuBr_2$ and $CuI_2$ which can be used in amounts ranging from 1 to 5 eq. An amine of Formula 3 is either commercially available, or is readily prepared as mentioned above. A compound of Formula 1D can be obtained by reacting a boron intermediate of Formula 5 with a heterocyclic intermediate of Formula 6, where X is bonded to a carbon atom of the heterocycle. Methods for conducting this Suzuki-Miyura coupling are analogous to those described above in Scheme 2 for the coupling of intermediates of a compound of Formula 2 with a boron intermediate of Formula 4 to provide a compound of Formula 1D. An intermediate of Formula 6 is commercially available, or can be easily prepared by one skilled in the art via known methodology.

Scheme 3

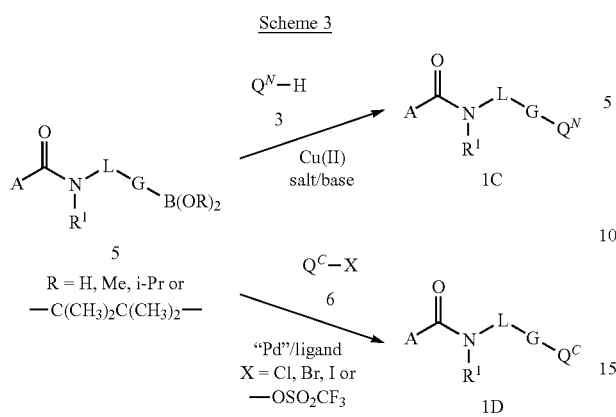

R = H, Me, i-Pr or
—C(CH$_3$)$_2$C(CH$_3$)$_2$—

A boron intermediate of Formula 5 can be prepared from an intermediate of Formula 2 in Scheme 2 using the same methods cited above for the preparation of a boron intermediate of Formula 4 in Scheme 2 from the corresponding halides or triflates as described in WO2007/034278, U.S. Pat. No. 8,080,566, *Org. Lett.* 2011, 13(6), 1366, and *Org. Lett.* 2012, 14(2), 600. A compound of Formula 2 in Scheme 2 above can be prepared by coupling an amine of Formula 7 with an acid intermediate of Formula 8 as shown in Scheme 4. Such couplings are common in organic synthesis and can be conducted under a wide variety of conditions (see March, *Advanced Organic Chemistry*, 3$^{rd}$ ed., John Wiley & Sons, New York, 1985, p. 1152).

Scheme 4

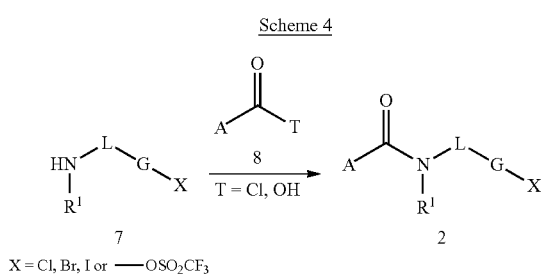

X = Cl, Br, I or —OSO$_2$CF$_3$

An intermediate of Formula 7A (i.e. a subset of a compound of Formula 7 wherein R$^1$ is cyclopropyl) can be synthesized from a primary amine of Formula 9 by the analogous methods discussed in *J. Med. Chem.* 2008, 51(11), 3238 and US2009/0176844 as shown in Scheme 5 below. A compound of Formula 9 is treated with from 1 to 4 eq. of 1-ethoxy-1-(trimethylsilyloxy)propane (10) in acetic acid/methanol solution for 1 to 24 h at temperatures ranging from ambient to the reflux temperature of the solvent. Molecular sieves can be present as well. A reducing agent such as sodium cyanoborohydride can then be added to the reaction mixture followed by further reaction for 1 to 24 h at temperatures ranging from 0° C. to the reflux temperature of the solvent. A compound of Formula 9 in Scheme 5 is known in the art and can be synthesized using established methods found in, for example, WO2011/047156, WO2006/117358, *Angewandte Chemie, Int. Ed.* 2012, 51(24), 5920, and *Tetrahedron Letters* 1993, 34(13), 2127.

Scheme 5

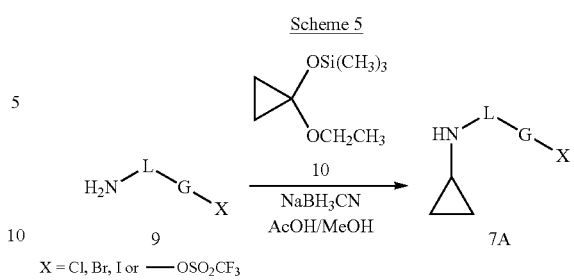

X = Cl, Br, I or —OSO$_2$CF$_3$

An intermediate of Formula 7B (i.e. another subset of a compound of Formula 7 wherein R$^1$ is C$_1$-C$_2$ alkoxy and L is —C(H)R$^{12b}$—C(R$^{13a}$)R$^{13b}$—) as shown in Scheme 6, is accessible from a carbonyl intermediate of Formula 11 via oximation and subsequent reduction with sodium cyanoborohydride as described in US2011/0230537, WO2011/147690 and WO2010/063700. An intermediate of Formula 11 is either commercially available or can be prepared by analogous methods described in WO2009/076747, WO2010/135650, WO2011/032277, WO2012/043791 and WO2011/152485.

Scheme 6

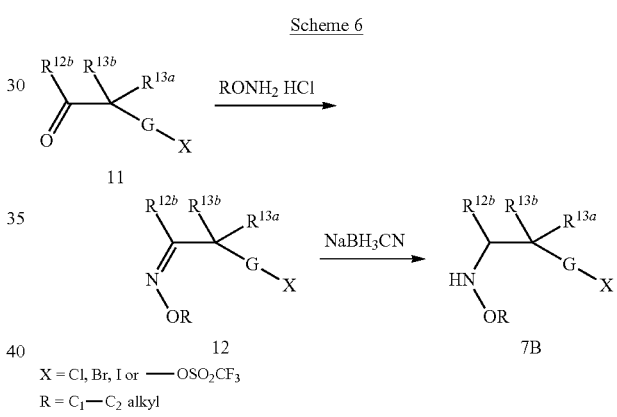

X = Cl, Br, I or —OSO$_2$CF$_3$
R = C$_1$—C$_2$ alkyl

A compound of Formula 1E (i.e. a subset of a compound of Formula 1 wherein Z is O; and R$^1$ is H) can be prepared by reacting an amine of Formula 9A with a compound of Formula 8 as shown in Scheme 7 below. This reaction can be accomplished using the methods described in the preparation of a compound of Formula 2 in Scheme 4 above.

Scheme 7

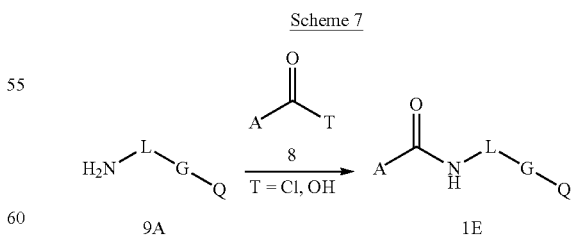

An amine precursor of Formula 13A can be synthesized from the previously described amine of Formula 9 via the reaction sequence illustrated in Scheme 8 below. An amine of a compound of Formula 9 can be protected with an appropriate protecting group "PG" (i.e. where PG is BOC—, PhCH$_2$OC(O)— or the like) to afford the N-protected intermediates such as a compound of Formula 13A. Transformation of an intermediate of Formula 13A to an intermediate of Formula 13 can be accomplished using methods analogous to those shown for the conversion of a compound of Formula 2 to compounds of Formulae 1C and 1D as shown in Scheme 2. An intermediate of Formula 13 can then be deprotected to provide the intermediate of Formula 9A. Many types of protecting groups are available for this sequence as outlined in Greene, T. W.; Wuts, P. G. M. *Protective Groups in Organic Synthesis*, 2nd ed.; Wiley: New York, 1991 and the practicing chemist will recognize which protecting groups are appropriate for the sequence.

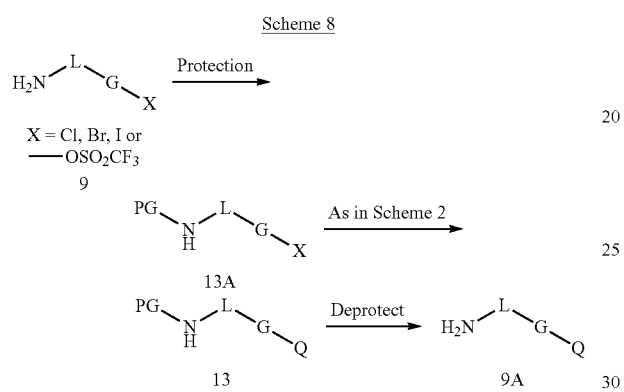

Scheme 8

An amine intermediate of Formula 9B (i.e. a subset of a compound of Formula 9 wherein L is —C(R$^{12a}$)H—C(H)R$^{13b}$— and R$^{13b}$ is H, C$_1$-C$_2$ alkyl, or C$_1$-C$_2$ haloalkyl) are accessible through reduction of a nitro intermediate of Formula 14 as shown in Scheme 9 below.

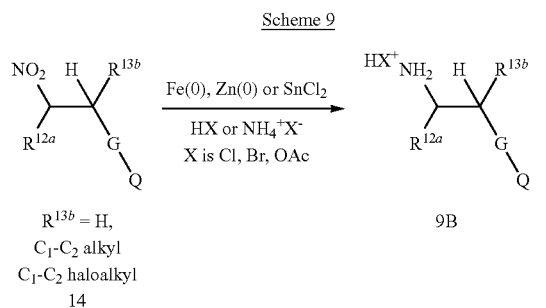

Scheme 9

The reaction can be carried out using Fe(0), Zn(0) or SnCl$_2$ in aqueous acidic media at temperatures ranging from ambient to the reflux temperature of the solvent. Alcoholic co-solvents such as methanol, ethanol, propanol and i-propanol may also be employed in the reaction. Proton sources such as aqueous hydrochloric, hydrobromic, acetic acids or aqueous NH$_4$Cl may be used in the reaction. The reaction is conducted for a time ranging from 0.25 h to 24 h to obtain a compound of Formula 9B which can be used as a crude intermediate without additional purification as the acid salt. Alternatively, the salt may be neutralized to the corresponding amine using procedures familiar to the practicing chemist. Typical examples for the subject reductions are given in *J. Labelled Compounds & Radiopharmaceuticals* 2011, 54(5), 239 and WO2011/138657.

An intermediate of Formula 14 can be prepared by sodium borohydride reduction of a nitroolefin intermediate of Formula 15 as shown in Scheme 10. Typical procedures for this type of reduction can be found, for example, in *Med. Chem. Lett.* 2012, 3(1), 5 and WO2011/124704

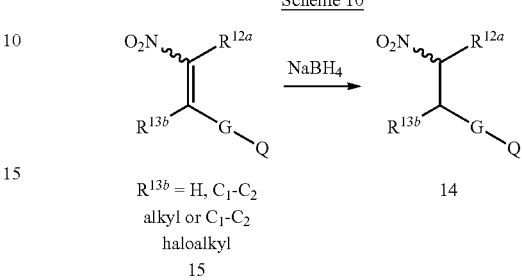

Scheme 10

A nitroolefin intermediate of Formula 15 can be synthesized by reacting an intermediate of Formula 16 with a nitro compound of Formula 17 as depicted in Scheme 11. The reaction is conveniently conducted in acetic acid in the presence of ammonium acetate as disclosed analogously in WO2007/141009.

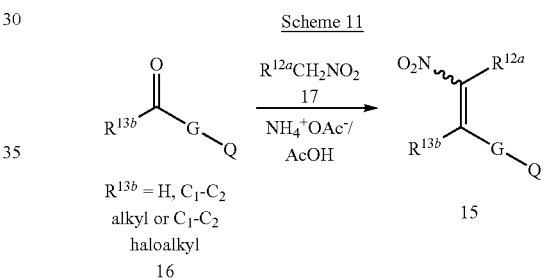

Scheme 11

An intermediate of Formula 16 can readily be prepared from a precursor of Formula 16A in Scheme 12 according to the methods previously outlined in Scheme 2 for the preparation of compounds of Formulae 1C and 1D from intermediates of a compound of Formula 2. Precursors of a compound of Formula 16A are readily available from commercial sources or can be prepared by known methods such as those disclosed in WO2012/044567, WO2012/110860, WO2012/103297 and WO2011/156698.

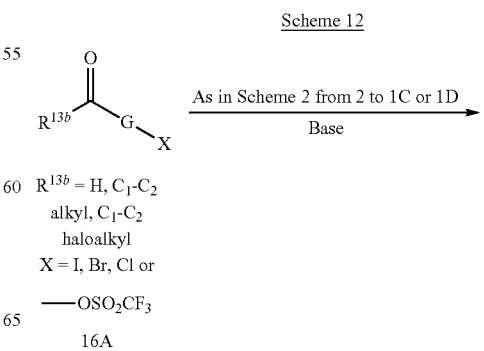

Scheme 12

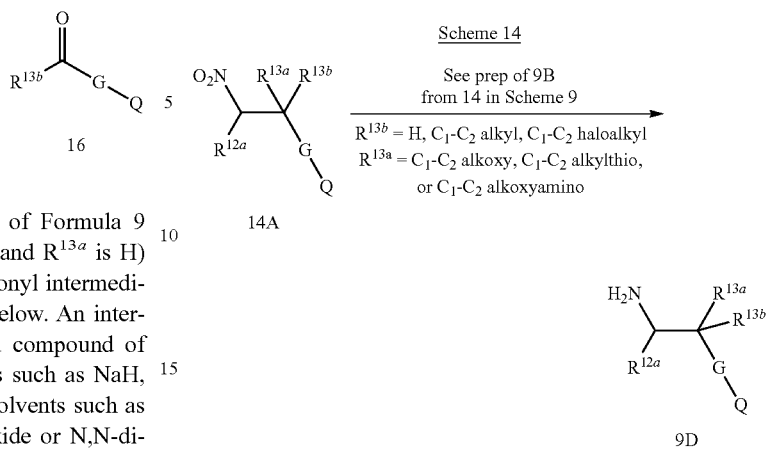

An amine of Formula 9C (i.e. a subset of Formula 9 wherein Q is an N-linked heterocycle, $Q^N$; and $R^{13a}$ is H) can be alternatively synthesized from a carbonyl intermediate Formula 16B as shown in Scheme 13 below. An intermediate of Formula 16A is reacted with a compound of Formula 3 in the presence of suitable bases such as NaH, $K_2CO_3$, $Na_2CO_3$ and $t\text{-BuO}^-K^+$ in aprotic solvents such as acetonitrile, tetrahydrofuran, dimethylsulfoxide or N,N-dimethylformamide at temperatures ranging from ambient to the reflux temperature of the solvent to afford a compound of 16B. Appropriate bases can be employed in amounts ranging from 1.0 to 3 eq., and the reaction times range from 0.5 to 24 h. An intermediate of Formula 16B may then be converted to an amine of Formula 9C using the same sequence described in previous Schemes 11, 10 and 9 for the analogous preparation of a compound of Formula 9B from a compound of Formula 16.

As shown in Scheme 15, an intermediate of Formula 14A can be accessed from the previously-described nitroolefins of Formula 15A (i.e. a compound of Formula 15 wherein $R^{13a}$ is $C_1$-$C_2$ alkoxy, $C_1$-$C_2$ alkylthio or $C_1$-$C_2$ alkoxyamino) using methods known in the art such as those disclosed in WO2008/148570.

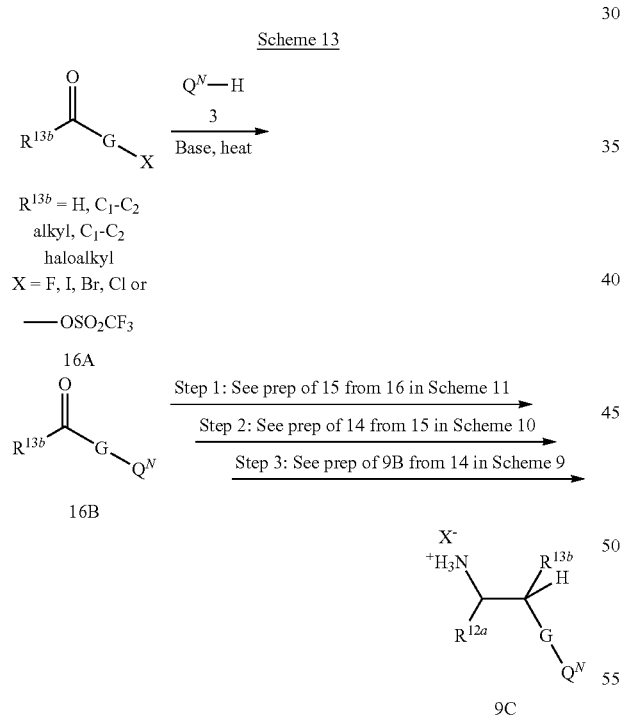

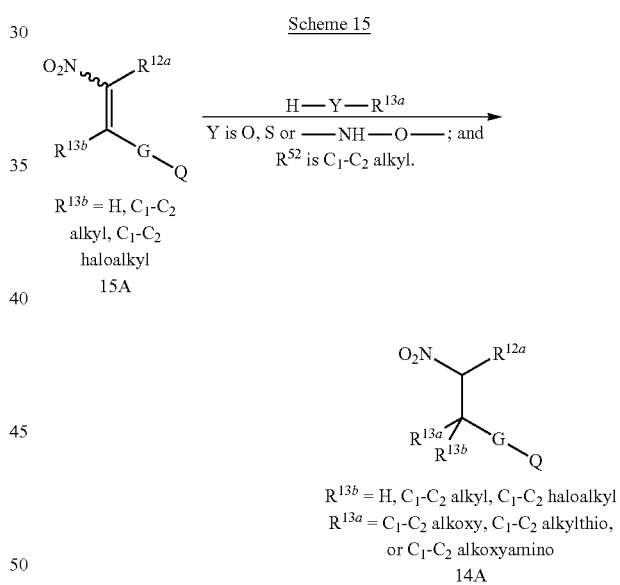

An amine intermediate of Formula 9D (i.e. a subset of Formula 9 wherein L is —C($R^{12a}$)H—C($R^{13a}$)$R^{13b}$—; $R^{13a}$ is $C_1$-$C_2$ alkoxy, $C_1$-$C_2$ alkylthio or $C_1$-$C_2$ alkoxyamino; and $R^{13b}$ is H, $C_1$-$C_2$ alkyl or $C_1$-$C_2$ haloalkyl), can be prepared from an intermediate of Formula 14A as shown in Scheme 14 below using the same procedures described above in Scheme 9 for the reduction of a nitro precursor of Formula 14 to the amines of Formula 9B.

An amine of Formula 9A (i.e. a compound of Formula 9 wherein L is —C(H)H—C($R^{13a}$)$R^{13b}$—; and $R^{13a}$ and $R^{13b}$ are H, $C_1$-$C_2$ alkyl, or $R^{13a}$ and $R^{13b}$ are taken together as $C_2$-$C_5$ alkanediyl) below can be accessed from an intermediate of Formula 17 as shown in Scheme 16 by analogy to the sequence cited in EP1500651. An intermediate of Formula 17A can be prepared from a precursor of Formula 17 according to the procedures outlined in Scheme 2 for the preparation of compounds of Formulae 1C and 1D from a compound of Formula 2. A precursor of Formula 17 is commercial, or can be synthesized in analogy to various known methods (see, for example WO2008/144222, WO2011/159760 and EP1500651).

Scheme 16

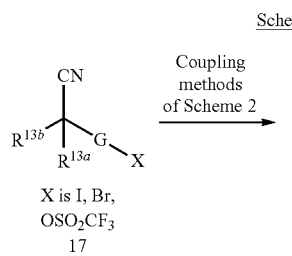

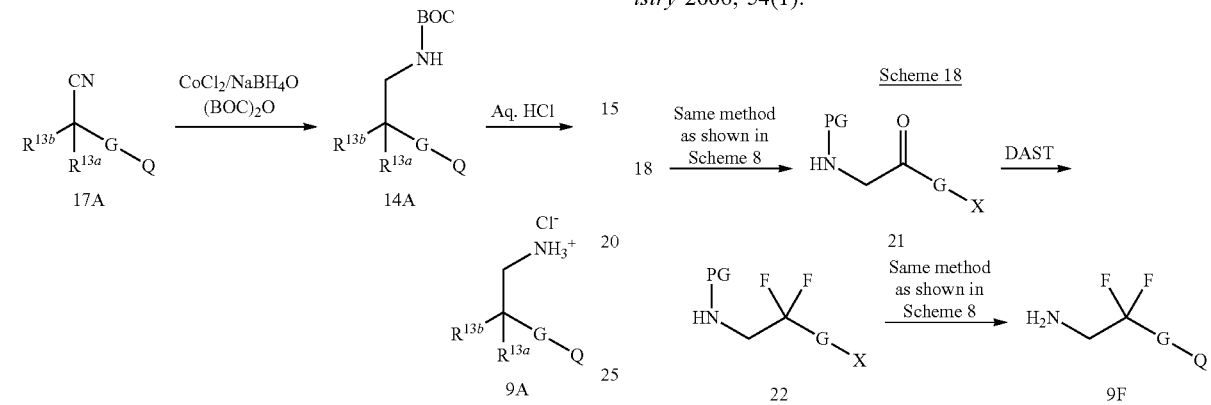

An amine of Formula 9E (i.e. a compound of Formula 9 wherein L is —CH₂CHF—) is preparable as shown in Scheme 17 below from a ketone intermediate of Formula 18. For the preparation of a compound of Formula 9E, reduction of a ketone of Formula 18 to an alcohol of Formula 19 can be achieved using reducing agents such as NaBH₄ as outlined in *J. Agricultural and Food Chemistry*, 2006, 54(1), 125. Subsequent reaction with a fluorinating agent such as diethylamino sulfur trifluoride (i.e. DAST) can provide an intermediate of Formula 20 by analogy to the methods cited in WO2006/015159. Conversion to an amine of Formula 9E can then be accomplished according to the previously-described sequence in Scheme 8 for the conversion of an amine of Formula 9 to an amine of Formula 9A.

Scheme 17

An amine of Formula 9F (i.e. a compound of Formula 9 wherein L is —CH₂CF₂—) is preparable as shown in Scheme 18 below from a ketone intermediate of Formula 18. A ketone of Formula 18 is first protected with an appropriate protecting group as to afford the protected aminoketone of Formula 21 as described previously in Scheme 8 for the protection of amines of Formula 9 to afford a protected amine of Formula 9A. Treatment of the protected amino ketone of Formula 21 with a fluorinating agent such as DAST can deliver a difluorinated intermediate of Formula 22, as described in WO2011/079102. The desired amine intermediate of Formula 9F may then be accessed by subjection of a compound of Formula 22 to the previously-described sequence in Scheme 8 for the conversion of an amine of Formula 13 to an amine of Formula 9A. An aminoketone of Formula 18 in Schemes 17 and 18 can be synthesized by analogous methods described in U.S. Pat. No. 5,106,986 and *Journal of Agricultural and Food Chemistry* 2006, 54(1).

Scheme 18

As shown in Scheme 19, a compound of Formula 1F (i.e. a compound of Formula 1 wherein Z is O; and L is 1,2-phenylene optionally substituted with up to 4-substitutents independently selected from halogen and $C_1$-$C_2$ alkyl) can be prepared by coupling of a boronate of Formula 23 with an intermediate of Formula 24 under the Suzuki conditions described in Scheme 2. Alternatively, a trialkyl tin compound of Formula 25 can be coupled with an intermediate of Formula 24 under Stille conditions to give a compound of Formula 1F. Stille couplings typically are conducted in the presence of Pd(0) or a Pd(II) salt, a ligand and a Cu(I) salt such as copper(I) iodide. The reaction is run in a solvent such as dioxane, 1,2-dimethoxyethane or toluene at a temperature ranging from ambient to the reflux temperature of the solvent. For conditions and reagents employed in Stille couplings see *Chemical Reviews* 2007, 107(1), 133. An intermediate of Formulae 23 and 25 can be prepared using commercially available starting materials or the methods outlined in Schemes 4 and 7.

Scheme 19

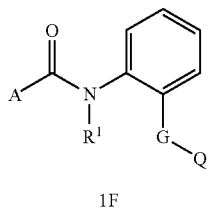

1F

An intermediate of Formula 24 is either commercially available or can be prepared as shown in Scheme 20 from an intermediate of Formula 26 by a variety of methods known to one skilled in the art. For example, when Q in a compound of Formula 24 is a nitrogen-linked heterocycle denoted by $Q^N$, and J in a compound of Formula 26 is halogen or trifluoromethanesulfonate, a compound of Formula 24 can either be prepared using the Buchwald-Hartwig conditions described for Scheme 2, or by reaction with heterocyclic amines $Q^N$-H (i.e. a compound of Formula 3) in the presence of a suitable base and solvent as illustrated in U.S. 20120202834, *J. Med. Chem.* 2012 55(21), 9089, WO2011016559 or WO2010139731. Alternatively, an intermediate of Formula 26 wherein J is a boronic acid or boronate ester, can be coupled with a heterocycle of Formula 3 using the Chan-Lam conditions as described for Scheme 3 to provide a compound of Formula 24 wherein Q is $Q^N$. A compound of Formula 24 wherein Q is a carbon-linked heterocycle denoted by $Q^C$ can be accessed by coupling a precursor of Formula 26 wherein J is Br, Cl, I or trifluoromethanesulfonate with boronate-substituted heterocycles $Q^C$-B(OR)$_2$ (i.e. a compound of Formula 4 in Scheme 2) using the Suzuki conditions of Scheme 2 or with trialkyltin-substituted heterocycles $Q^C$-Sn(R)$_3$ using the Stille conditions of Scheme 19. Alternatively, a compound of Formula 26 wherein J is a boronate or trialkyltin group may also be coupled with halogen-substituted heterocycles $Q^C$-X using the methods shown in Schemes 2 or 19, respectively, to afford a compound of Formula 24 wherein Q is $Q^C$. The skilled chemist will realize that prudent choice of groups $X^6$ and J in reactions involving a compound of Formula 26 is needed, and that isomeric products can occur in cases where groups $X^6$ and J are similar in reactivity. In cases where regioisomeric mixtures are produced, the desired product can be isolated using routine separation techniques known in the art.

Scheme 20

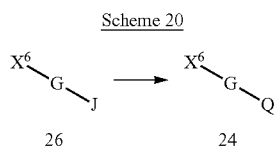

When J in a compound of Formula 26 is a functional group such as an alkene, alkyne, oxime, nitrile or ketone, the functional group an be converted to various heterocycles using methods described in Katritsky, *Advances in Heterocyclic Chemistry*, Elsevier, Vol. 1-104.

As shown in Scheme 21 a compound of Formula 1F can also be prepared by coupling an intermediate analogous to those depicted in Scheme 19 wherein functional groups in the starting reagents have been interchanged. Thus, coupling of an intermediate of Formula 27 with a boronate ester of Formula 24A and a trialkyltin intermediate of Formula 24B using methods described in Scheme 19 affords a compound of Formula 1F.

Scheme 21

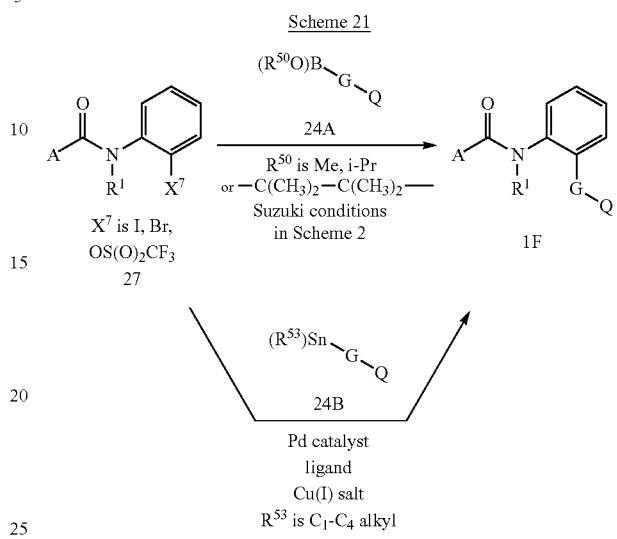

It is recognized that some reagents and reaction conditions described above for preparing a compound of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in CDCl$_3$ at 500 MHz unless otherwise indicated; "s" means singlet, "d" means doublet, "t" means triplet, "q" means quartet, "m" means multiplet, "dd" means doublet of doublets, "dt" means doublet of triplets, "br s" means broad singlet.

Example 1

Preparation of N-[1-methyl-2-[6-[3-(trifluoromethyl)-1H-pyrazol-1-yl]-3-pyridinyl]ethyl]-3-(trifluoromethyl)-2-pyridinecarboxamide (Compound 84)

Step A: Preparation of 6-[3-(trifluoromethyl)-1H-pyrazol-1-yl]-3-pyridinecarboxaldehyde A mixture of 6-fluoro-3-pyridine carboxaldehyde (1.5 g, 12 mmol), 3-(trifluoromethyl)pyrazole (1.6 g, 12 mmol) and potassium carbonate (1.8 g, 13 mmol) in 20 mL of N,N-dimethylformamide were heated to 100° C. for approximately 16 h. The reaction mixture was cooled to ambient temperature and poured into 100 mL ice water. After 20 min the precipitate was collected by filtration, dissolved in dichloromethane, dried over $MgSO_4$, and concentrated under reduced pressure to yield 1.2 g of the title compound.

$^1$H NMR δ 10.13 (s, 1H), 8.91 (d, 1H), 8.71 (d, 1H), 8.34 (m, 1H), 8.22 (d, 1H), 6.77 (d, 1H).

Step B: Preparation of 5-(2-nitro-1-propen-1-yl)-2-[3-(trifluoromethyl)-1H-pyrazol-1-yl]pyridine A mixture of 6-[3-(trifluoromethyl)-1H-pyrazol-1-yl]-3-pyridinecarboxaldehyde (i.e. the compound obtained in Step A above) (1.5 g, 6.2 mmol) and ammonium acetate (0.096 g, 1.2 mmol) were heated to reflux in 15 mL of nitroethane for approximately 16 h. The reaction mixture was concentrated, dissolved in toluene, reconcentrated and then purified by medium pressure liquid chromatography (0 to 50% ethyl acetate in hexanes as eluent) to yield 0.34 g of the title compound.

$^1$H NMR δ 8.65 (m, 1H), 8.52 (d, 1H), 8.15 (d, 1H), 8.07 (s, 1H), 7.93 (m, 1H), 6.75 (d, 1H), 2.51 (d, 3H).

Step C: Preparation of α-methyl-6-[3-(trifluoromethyl)-1H-pyrazol-1-yl]-3-pyridineethanamine 5-(2-Nitro-1-propen-1-yl)-2-[3-(trifluoromethyl)-1H-pyrazol-1-yl]pyridine (i.e. the compound obtained in Step B above) (0.31 g, 1 mmol) in 10 mL tetrahydrofuran was added drop-wise to a solution of lithium aluminum hydride in 10 mL of tetrahydrofuran at 0° C. After the addition was complete, the reaction was refluxed for approximately 16 h. The reaction mixture was cooled to ambient temperature and then treated sequentially with 0.13 mL water, 0.13 mL 15% NaOH and then 0.38 mL water. After 30 min of stirring, the reaction mixture was filtered through Celite® diatomaceous filter aid and concentrated under reduced pressure to yield 0.22 g of the title compound which was used in the next step without further purification or characterization.

Step D: Preparation of N-[1-methyl-2-[6-[3-(trifluoromethyl)-1H-pyrazol-1-yl]-3-pyridinyl]ethyl]-3-(trifluoromethyl)-2-pyridinecarboxamide 3-Trifluoromethylpyridine-2-carboxylic acid (0.086 g, 0.4 mmol) was heated to reflux in 10 mL thionyl chloride for 1 h. The mixture was concentrated under reduced pressure and the crude residue was dissolved in 10 mL of dichloromethane and added to a solution of α-methyl-6-[3-(trifluoromethyl)-1H-pyrazol-1-yl]-3-pyridineethanamine (i.e. the compound obtained in Step C above) (0.11 g, 0.4 mmol) and N,N-diisopropylethylamine (0.16 g, 1.2 mmol) in 5 mL of dichloromethane at 0° C. The reaction was allowed to warm to ambient temperature and stir for approximately 16 h. The reaction mixture was diluted with dichloromethane, washed with 1N aqueous hydrochloric acid, dried over $MgSO_4$, concentrated under reduced pressure and then purified by medium pressure liquid chromatography (0-100% ethyl acetate in hexanes as eluent) to yield 0.04 g of the title compound, a compound of the present invention.

$^1$H NMR δ 8.71 (m, 1H), 8.57 (m, 1H), 8.29 (d, 1H), 8.17 (m, 1H), 7.96 (d, 1H), 7.77 (m, 1H), 7.57 (m, 2H), 6.69 (d, 1H), 4.46 (m, 1H), 2.99 (m, 2H), 1.29 (d, 3H).

Example 2

Preparation of 3-(difluoromethyl)-N-[2-[5-fluoro-6-[3-(trifluoromethyl)-1H-pyrazol-1-yl]-3-pyridinyl]phenyl]-1-methyl-1H-pyrazole-4-carboxamide (Compound 68)

Step A: Preparation of 5-bromo-3-fluoro 2-[3-(trifluoromethyl)-1H-pyrazol-1-yl]pyridine 3-(Trifluoromethyl)pyrazole (0.65 g, 4.8 mmol), 5-bromo-2,3-difluoropyridine (0.93 g, 4.8 mmol) and potassium carbonate (0.73 g, 5.3 mmol) were stirred for approximately 16 h in 10 mL of acetonitrile. The reaction mixture was then concentrated under reduced pressure and purified by medium pressure liquid chromatography (0-100% ethyl acetate in hexanes as eluent) to yield 0.64 g of the title compound.

$^1$H NMR δ 8.42 (d, 1H), 8.33 (m, 1H), 7.86 (m, 1H), 6.77 (d, 1H).

Step B: Preparation of 3-(difluoromethyl)-N-[2-[5-fluoro-6-[3-(trifluoromethyl)-1H-pyrazol-1-yl]-3-pyridinyl]phenyl]-1-methyl-1H-pyrazole-4-carboxamide 3-(Difluoromethyl)-1-methyl-1H-pyrazole-4-carbonyl chloride (prepared from commercial 3-(difluoromethyl)-1-methyl-1H-pyrazole-4-carboxylic acid according to the procedure described in PCT Patent Application WO 2008/053043; 0.30 g, 1.5 mmol), 2-(4,4,5,5-tetramethyl-1,3,2-dioxaborolan-2-yl)-benzenamine (0.31 g, 1.4 mmol) and cesium carbonate (1.0 g, 3.1 mmol) were combined in 5 mL of 1,2-dimethoxyethane and stirred for approximately 16 h at ambient temperature. To this mixture was added 5-bromo-3-fluoro 2-[3-(trifluoromethyl)-1H-pyrazol-1-yl]pyridine (i.e. the compound obtained in Example 2, Step A above) (0.48 g, 1.6 mmol), bis(triphenylphosphine)palladium(II) dichloride (0.049 g, 0.071 mmol), saturated sodium carbonate solution in water (3 mL) and an additional 3 mL of 1,2-dimethoxyethane. The mixture was heated to 100° C. for 3 h, cooled to ambient temperature, diluted with ethyl acetate, washed 3 times with brine, dried over $MgSO_4$, filtered and concentrated under reduced pressure. The resulting residue was purified by medium pressure liquid chromatography (0-100% ethyl acetate in hexanes as eluent) to yield a crude residue which was subsequently purified by reverse phase medium pressure liquid chromatography (0-100% 1:1 acetonitrile to methanol in water as eluent) to yield 0.10 g of the title compound, a compound of the present invention.

$^1$H NMR δ 8.38 (s, 2H), 8.06 (d, 1H), 7.96 (s, 1H), 7.84 (bs, 1H), 7.73 (m, 1H), 7.51 (m, 1H), 7.33 (m, 2H), 6.78 (d, 1H), 6.64 (t, 1H), 3.91 (s, 3H).

Example 3

Preparation of 3-(trifluoromethyl)-N-[2-[5-[3-(trifluoromethyl)-1H-pyrazol-1-yl]-2-pyrazinyl]phenyl]-2-pyridinecarboxamide (Compound 3)

Step A: Preparation of 2-bromo-5-(2-nitrophenyl)pyrazine

A mixture of 2,5-dibromopyrazine (10 g, 42 mmol), 2-nitrophenylboronic acid (8.2 g, 49 mmol) and sodium carbonate (15.2 g, 143 mmol) in 300 mL 1,2-dimethoxyethane and 80 mL water was purged with nitrogen gas. Bis(triphenylphosphine)palladium(II) dichloride (4.0 g, 5.7 mmol) was added and the reaction was heated to 80° C. for 16 h. The reaction mixture was then cooled to ambient temperature, diluted with ethyl acetate, washed with water, dried over sodium sulfate, evaporated under reduced pressure and then purified using silica gel column chromatography (15% ethyl acetate in petroleum ether as eluent) to yield 4.5 g of the title compound.
$^1$H NMR (400 MHz, dmso-d$_6$) δ 8.92 (dd, 2H), 8.10 (d, 1H), 7.89 (d, 2H), 7.80 (dd, 1H).

Step B: Preparation of 2-(2-nitrophenyl)-5-[3-(trifluoromethyl)-1H-pyrazol-1-yl]pyrazine A mixture of 2-bromo-5-(2-nitrophenyl)pyrazine (i.e. the compound obtained in Example 3, Step A above) (4.0 g, 14 mmol), 3-(trifluoromethyl)pyrazole (2.2 g, 16 mmol) and potassium carbonate (5.9 g, 43 mmol) in 20 mL N,N-dimethylformamide was heated to 80° C. for 2 h. The reaction mixture was cooled to ambient temperature and diluted with ice water, which caused a precipitate to form. The solid was isolated by filtration and used without further purification.
$^1$H NMR (400 MHz, dmso-d$_6$) δ 9.26 (d, 1H), 9.02 (d, 1H), 8.93 (dd, 1H), 8.13 (dd, 1H), 7.92 (m, 2H), 7.81 (m, 1H), 7.20 (d, 1H).

Step C: Preparation of 2-[5-[3-(trifluoromethyl)-1H-pyrazol-1-yl]-2-pyrazinyl]benzenamine To a mixture of 2-(2-nitrophenyl)-5-[3-(trifluoromethyl)-1H-pyrazol-1-yl]pyrazine (3.9 g, 12 mmol) (i.e. the compound obtained in Example 3, Step B above) in 20 mL ethanol was added palladium on carbon (0.40 g, 0.4 mmol). The mixture was stirred for 2 h at ambient temperature under a hydrogen balloon, and then filtered through Celite® diatomaceous filter aid and concentrated under reduced pressure. The crude residue was purified using silica gel column chromatography (10% ethyl acetate in petroleum ether as eluent) to yield 2.1 g of the title compound.
$^1$H NMR (400 MHz, dmso-d$_6$) δ 9.22 (d, 1H), 9.05 (d, 1H), 8.86 (d, 1H), 7.74 (dd, 1H), 7.18 (m, 2H), 6.83 (d, 1H), 6.68 (m, 1H), 6.53 (s, 2H).

Step D: Preparation of 3-(trifluoromethyl)-N-[2-[5-[3-(trifluoromethyl)-1H-pyrazol-1-yl]-2-pyrazinyl]phenyl]-2-pyridinecarboxamide)

A mixture of 3-trifluoromethyl-2-pyridine carboxylic acid (0.33 g, 1.6 mmol), (dimethylamino)-N,N-dimethyl(3H-[1,2,3]triazolo[4,5-b]pyridin-3-yloxy)methaniminium hexafluorophosphate (i.e. HATU, 0.059 g, 1.6 mmol), and N,N-diisopropylethylamine (0.33 g, 2.6 mmol) were stirred in 10 mL dichloromethane. After 15 min, 2-[5-[3-(trifluoromethyl)-1H-pyrazol-1-yl]-2-pyrazinyl]benzenamine (i.e. the compound obtained in Example 3, Step C above) (0.4 g, 1.3 mmol) was added and the reaction was stirred at ambient temperature for approximately 16 h. The reaction mixture was then diluted with water and extracted with ethyl acetate. The combined organic extracts were washed with water, dried over Na$_2$SO$_4$, evaporated under reduced pressure and then purified using silica gel column chromatography (20% ethyl acetate in petroleum ether as eluent) to yield 0.36 g of the title compound, a compound of the present invention.
$^1$H NMR (400 MHz, dmso-d$_6$) δ 12.20 (s, 1H), 9.31 (s, 1H), 9.05 (m, 2H), 8.91 (bs, 1H), 8.36 (m, 2H), 7.97 (d, 1H), 7.85 (m, 1H), 7.61 (t, 1H), 7.41 (t, 1H), 7.18 (d, 1H).

Example 4

Preparation of 3-(trifluoromethyl)-N-[2-[6-[3-(trifluoromethyl)-1H-pyrazol-1-yl]-3-pyridazinyl]phenyl]-2-pyridinecarboxamide (Compound 59)

Step A: Preparation of 3-bromo-6-(2-nitrophenyl)pyridazine

A mixture of 3,6-dibromopyridazine (5 g, 21 mmol), 2-nitrophenylborononic acid (4.1 g, 25 mmol), and sodium carbonate (7.6 g, 72 mmol) in 150 mL 1,2-dimethoxyethane and 40 mL water was purged with nitrogen gas for 15 min. Bis(triphenylphosphine)palladium(II) dichloride (2.0 g, 2.9 mmol) was added and the reaction was heated to 80° C. for 16 h. The reaction mixture was cooled to ambient temperature, diluted with ethyl acetate, washed with water, dried over sodium sulfate, evaporated under reduced pressure and then purified using silica gel column chromatography (15% ethyl acetate in petroleum ether as eluent) to yield 2.5 g of the title compound.
$^1$H NMR (400 MHz, dmso-d$_6$) δ 8.23 (d, 1H), 8.15 (d, 1H), 8.07 (d, 1H), 7.91 (m, 1H), 7.82 (m, 2H)

Step B: Preparation of 3-(2-nitrophenyl)-6-[3-(trifluoromethyl)-1H-pyrazol-1-yl]pyridazine Prepared similarly as described in Example 3, Step B.

Step C: Preparation of 2-[6-[3-(trifluoromethyl)-1H-pyrazol-1-yl]-3-pyridazinyl]benzenamine Prepared similarly as described in Example 3, Step C.

Step D: Preparation of 3-(trifluoromethyl)-N-[2-[6-[3-(trifluoromethyl)-1H-pyrazol-1-yl]-3-pyridazinyl]phenyl]-2-pyridinecarboxamide Prepared similarly as described in Example 3, Step D, a compound of the present invention.
$^1$H NMR (400 MHz, dmso-d$_6$) δ 12.17 (s, 1H), 9.14 (d, 1H), 8.98 (d, 1H), 8.39 (m, 3H), 8.27 (d, 1H), 7.90 (dd, 1H), 7.84 (dd, 1H), 7.64 (m, 1H), 7.44 (m, 1H), 7.22 (d, 1H).

By the procedures described herein together with methods known in the art, the following compounds of Tables 1 to 1223 can be prepared. The following abbreviations are used in the Tables which follow: i means iso, c means cyclo, Me means methyl, Et means ethyl, Pr means propyl, c-Pr means cyclopropyl, i-Pr means isopropyl, Bu means butyl, c-Bu means cyclobutyl, c-pent means cyclopentyl, c-hex means cyclohexyl, Ph means phenyl, OMe means methoxy, OEt means ethoxy, —C(=O)OMe means methoxycarbonyl, —CN means cyano and —NO$_2$ means nitro. The following Exhibit A shows specific embodiments of variable A from the Summary of the Invention for a compound of Formula 1 where the bond projecting to the right is attached to the remainder of a compound of Formula 1 (i.e. A-C(=Z)N(R$^1$)—).

Exhibit A

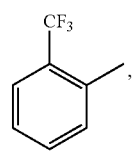
A-1a

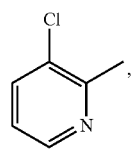
A-1b

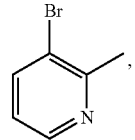
A-1c

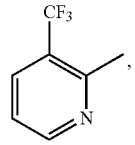
A-1d

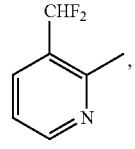
A-1e

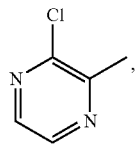
A-1f

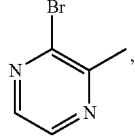
A-1g

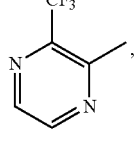
A-1h

-continued

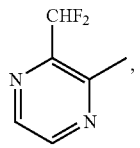
A-1i

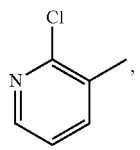
A-1j

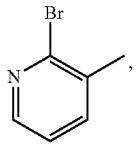
A-1k

A-1l

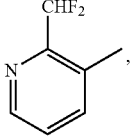
A-1m

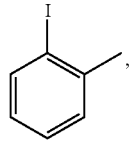
A-1n

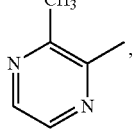
A-1o

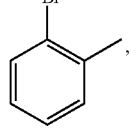
A-1p

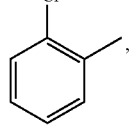
A-1q

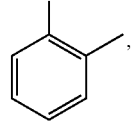
A-1r

-continued
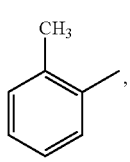 A-1s
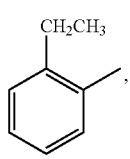 A-1t
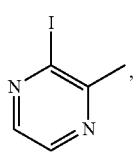 A-1u
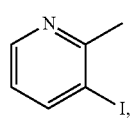 A-1v
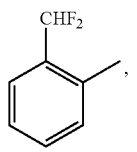 A-1w
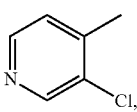 A-1x
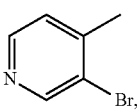 A-1y
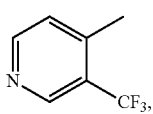 A-1z
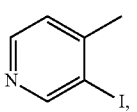 A-1aa
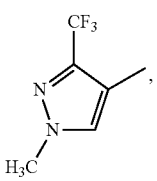 A-2a
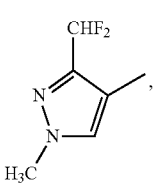 A-2b
-continued
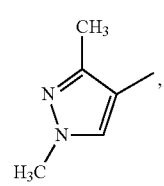 A-2c
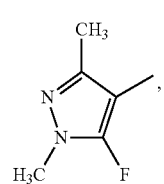 A-2d
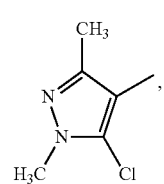 A-2e
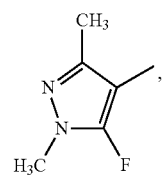 A-2f
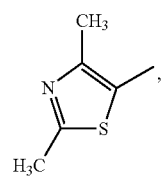 A-3a
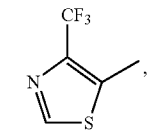 A-3b
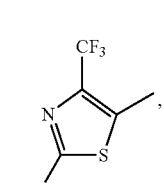 A-3c
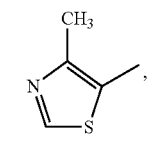 A-3d
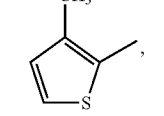 A-4a -continued
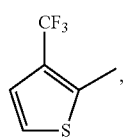 A-4b
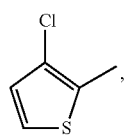 A-4c
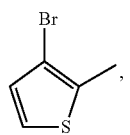 A-4d
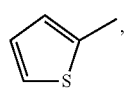 A-4e
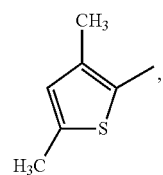 A-4f
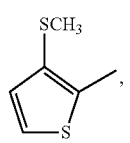 A-4g
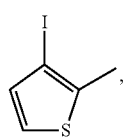 A-4h
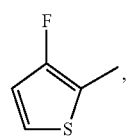 A-4i
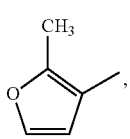 A-5a
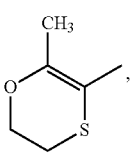 A-6a
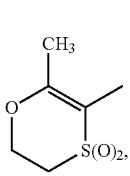 A-6b
-continued
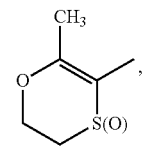 A-6c
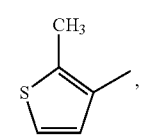 A-7a
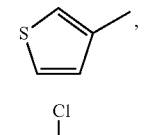 A-7b
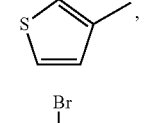 A-7c
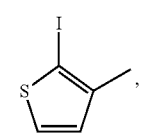 A-7d
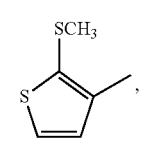 A-7e
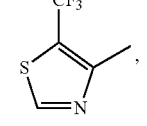 A-7f
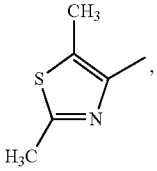 A-8a
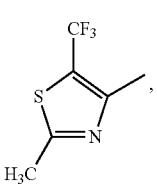 A-8c
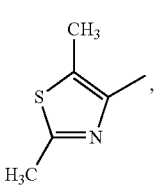 A-8b
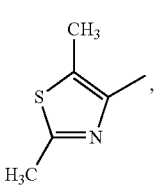 A-8c -continued

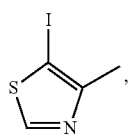  A-8d

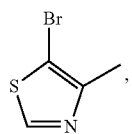  A-8e

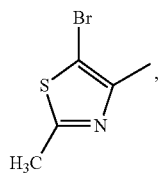  A-8f

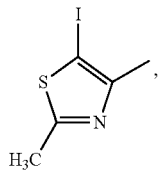  A-8g

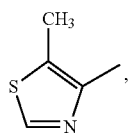  A-8h

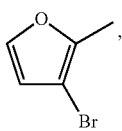  A-9a

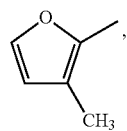  A-9b

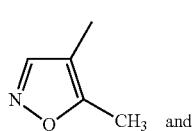 and  A-10a

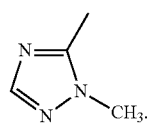.  A-11a

The below structure (i.e. a compound of Formula 1 wherein Z is O; $R^1$ is H; L is 1,2-phenylene; and G is G-1) is used to construct the following Tables. The value of n is understood to be assigned the appropriate number of $R^2$ values listed for each Table entry.

TABLE 1

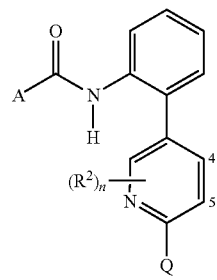

For Table 1, the value for A is A-1a; n is 0; and each Q is selected from the values for Q listed in Exhibit B:

| Exhibit B |
|---|
| 3-CF$_3$-1H-pyrazol-1-yl |
| 4-CF$_3$-1H-pyrazol-1-yl |
| 5-CF$_3$-1H-pyrazol-1-yl |
| 3-CHF$_2$-1H-pyrazol-1-yl |
| 4-CHF$_2$-1H-pyrazol-1-yl |
| 5-CHF$_2$-1H-pyrazol-1-yl |
| 3-OMe-1H-pyrazol-1-yl |
| 4-OMe-1H-pyrazol-1-yl |
| 5-OMe-1H-pyrazol-1-yl |
| 3-MeOC(=O)-1H-pyrazol-1-yl |
| 4-MeOC(=O)-1H-pyrazol-1-yl |
| 5-MeOC(=O)-1H-pyrazol-1-yl |
| 3-CF$_3$-5-Me-1H-pyrazol-1-yl |
| 3,4-di-Cl-1H-pyrazol-1-yl |
| 3-CHF$_2$-1H-[1,2,4]triazol-1-yl |
| 3,5-di-Me-1H-[1,2,4]triazol-1-yl |
| 3,5-di-Br-1H-[1,2,4]triazol-1-yl |
| 4-CF$_3$-2H-[1,2,3]triazol-2-yl |
| 4-Br-2H-[1,2,3]triazol-2-yl |
| 4,5-di-Cl-2H-[1,2,3]triazol-2-yl |
| 4-CF$_3$-1H-[1,2,3]triazol-1-yl |
| 4-Br-1H-[1,2,3]triazol-1-yl |
| 3-CF$_3$-1H-pyrrol-1-yl |
| 3,4-di-CF$_3$-1H-pyrrol-1-yl |
| 1H-pyrrol-1-yl |
| 1-i-Pr-1H-pyrazol-3-yl |
| 1-Me-4-CF$_3$-1H-pyrazol-3-yl |
| 1-i-Pr-1H-pyrazol-4-yl |
| 1-Me-3-CF$_3$-1H-pyrazol-4-yl |
| 1-Et-1H-[1,2,4]triazol-3-yl |
| 3-c-Pr-1H-pyrazol-1-yl |
| 3-c-pent-1H-pyrazol-1-yl |
| 3-Me-1H-pyrazol-1-yl |
| 4-Me-1H-pyrazol-1-yl |
| 5-Me-1H-pyrazol-1-yl |
| 3-Et-1H-pyrazol-1-yl |
| 3-Et-1H-pyrazol-1-yl |
| 3-Et-1H-pyrazol-1-yl |
| 3-CN-1H-pyrazol-1-yl |
| 4-CN-1H-pyrazol-1-yl |
| 5-CN-1H-pyrazol-1-yl |
| 3-Ph-1H-pyrazol-1-yl |
| 4-Ph-1H-pyrazol-1-yl |
| 5-Ph-1H-pyrazol-1-yl |
| 3,4-di-Me-1H-pyrazol-1-yl |
| 1H-pyrazol-1-yl |
| 3-F-1H-[1,2,4]triazol-1-yl |
| 3,5-di-CF$_3$-1H-[1,2,4]triazol-1-yl |
| 3-Ph-1H-[1,2,4]triazol-1-yl |
| 4-CHF$_2$-2H-[1,2,3]triazol-2-yl |
| 4-Ph-2H-[1,2,3]triazol-2-yl |
| 4,5-di-Br-2H-[1,2,3]triazol-2-yl |
| 4-CHF$_2$-1H-[1,2,3]triazol-1-yl |
| 4-Ph-1H-[1,2,3]triazol-1-yl |
| 3-CHF$_2$-1H-pyrrol-1-yl |
| 2,4-di-CF$_3$-1H-pyrrol-1-yl |
| 1-Me-1H-pyrazol-3-yl |
| 1-(2,2,2-tri-F-ethyl)-1H-pyrazol-3-yl |

Exhibit B

1-Me-1H-pyrazol-4-yl
1-(2,2,2-tri-F-ethyl)-1H-pyrazol-4-yl
3-Me-1-CF$_3$-1H-pyrazol-4-yl
1-i-Pr-1H-[1,2,4]triazol-3-yl
4-c-Pr-1H-pyrazol-1-yl
4-c-pent-1H-pyrazol-1-yl
5-Me-furan-2-yl
3-F-1H-pyrazol-1-yl
4-F-1H-pyrazol-1-yl
5-F-1H-pyrazol-1-yl
3-Cl-1H-pyrazol-1-yl
4-Cl-1H-pyrazol-1-yl
5-Cl-1H-pyrazol-1-yl
3-OCF$_3$-1H-pyrazol-1-yl
4-OCF$_3$-1H-pyrazol-1-yl
5-OCF$_3$-1H-pyrazol-1-yl
3,5-di-Me-1H-pyrazol-1-yl
3,5-di-CF$_3$-1H-pyrazol-1-yl
3,5-di-CHF$_2$-1H-pyrazol-1-yl
3,4-di-CF$_3$-1H-pyrazol-1-yl
3-Me-1H-[1,2,4]triazol-1-yl
3-Cl-1H-[1,2,4]triazol-1-yl
3,5-di-CHF$_2$-1H-[1,2,4]triazol-1-yl
1H-[1,2,4]triazol-1-yl
4-F-2H-[1,2,3]triazol-2-yl
4,5-di-Me-2H-[1,2,3]triazol-2-yl
1H-[1,2,3]triazol-2-yl
4-F-1H-[1,2,3]triazol-1-yl
1H-[1,2,3]triazol-1-yl
3,4-di-Me-1H-pyrrol-1-yl
3,4-di-Br-1H-pyrrol-1-yl
1-CF$_3$-1H-pyrazol-3-yl
1-Ph-1H-pyrazol-3-yl
1-CF$_3$-1H-pyrazol-4-yl
1-Ph-1H-pyrazol-4-yl
1-Me-1H-[1,2,4]triazol-3-yl
1-Ph-1H-[1,2,4]triazol-3-yl
3-c-Bu-1H-pyrazol-1-yl
3-c-hex-1H-pyrazol-1-yl
furan-2-yl
3-Br-1H-pyrazol-1-yl
4-Br-1H-pyrazol-1-yl
5-Br-1H-pyrazol-1-yl
5-I-1H-pyrazol-1-yl
3-OCHF$_2$-1H-pyrazol-1-yl
4-OCHF$_2$-1H-pyrazol-1-yl
5-OCHF$_2$-1H-pyrazol-1-yl
3,5-di-F-1H-pyrazol-1-yl
3,5-di-Cl-1H-pyrazol-1-yl
3,5-di-Br-1H-pyrazol-1-yl
3,4-di-Br-1H-pyrazol-1-yl
3-CF$_3$-1H-[1,2,4]triazol-1-yl
3-Br-1H-[1,2,4]triazol-1-yl
3,5-di-Cl-1H-[1,2,4]triazol-1-yl
4-Me-2H-[1,2,3]triazol-2-yl
4-Cl-2H-[1,2,3]triazol-2-yl
4,5-di-CF$_3$-2H-[1,2,3]triazol-2-yl
4-Me-1H-[1,2,3]triazol-1-yl
4-Cl-1H-[1,2,3]triazol-1-yl
3-Me-1H-pyrrol-1-yl
2,4-di-Me-1H-pyrrol-1-yl
3,4-di-Cl-1H-pyrrol-1-yl
1-Et-1H-pyrazol-3-yl
1,4-di-Me-1H-pyrazol-3-yl
1-Et-1H-pyrazol-4-yl
1,3-di-Me-1H-pyrazol-4-yl
1-CF$_3$-1H-[1,2,4]triazol-3-yl
3-I-1H-pyrazol-1-yl
5-CF$_3$-furan-2-yl
4-c-Bu-1H-pyrazol-1-yl
4-I-1H-pyrazol-1-yl
4-c-hex-1H-pyrazol-1-yl

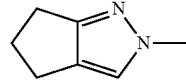

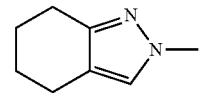

Table 2 is constructed in the same fashion as Table 1, except in the Row Heading the phrase "A is A-1a; n is 0" is replaced with the phrase "A is A-1a; $(R^2)_n$ is 5-F" as shown below in the column labeled Row Heading for Table 2. For Table 2 where $R^2$ is 5-F it is understood to mean that n is 1 and $R^2$ is F located at the 5-position of the G ring. Therefore, the first entry in Table 2 is a compound of Formula 1 wherein Z is O; $R^1$ is H; L is 1,2-phenylene; G is G-1; A is A-1a; $R^2$ is 5-F; n is 1; and Q is 3-CF$_3$-pyrazol-1-yl. The second entry in Table 2 is a compound of Formula 1 wherein Z is O; $R^1$ is H; L is 1,2-phenylene; G is G-1; A is A-1a; $R^2$ is 5-F; n is 1; and Q is 4-CF$_3$-1H-pyrazol-1-yl. The remaining entries in Table 2 are constructed in the same manner.

Tables 3 through 272 are constructed similarly.

| Table | Row heading |
|---|---|
| 2 | A is A-1a, $(R^2)_n$ is 5-F |
| 3 | A is A-1a, $(R^2)_n$ is 5-Cl |
| 4 | A is A-1a, $(R^2)_n$ is 5-Br |
| 5 | A is A-1a, $(R^2)_n$ is 5-I |
| 6 | A is A-1a, $(R^2)_n$ is 5-Me |
| 7 | A is A-1a, $(R^2)_n$ is 5-Et |
| 8 | A is A-1a, $(R^2)_n$ is 5-CF$_3$ |
| 9 | A is A-1a, $(R^2)_n$ is 5-CN |
| 10 | A is A-1a, $(R^2)_n$ is 5-OMe |
| 11 | A is A-1a, $(R^2)_n$ is 5-NO$_2$ |
| 12 | A is A-1a, $(R^2)_n$ is 4-F |
| 13 | A is A-1a, $(R^2)_n$ is 4-Cl |
| 14 | A is A-1a, $(R^2)_n$ is 4-Me |
| 15 | A is A-1a, $(R^2)_n$ is 4,5-di-F |
| 16 | A is A-1a, $(R^2)_n$ is 4,5-di-Cl |
| 17 | A is A-1d, $(R^2)_n$ is H (n is 0) |
| 18 | A is A-1d, $(R^2)_n$ is 5-F |
| 19 | A is A-1d, $(R^2)_n$ is 5-Cl |
| 20 | A is A-1d, $(R^2)_n$ is 5-Br |
| 21 | A is A-1d, $(R^2)_n$ is 5-I |
| 22 | A is A-1d, $(R^2)_n$ is 5-Me |
| 23 | A is A-1d, $(R^2)_n$ is 5-Et |
| 24 | A is A-1d, $(R^2)_n$ is 5-CF$_3$ |
| 25 | A is A-1d, $(R^2)_n$ is 5-CN |
| 26 | A is A-1d, $(R^2)_n$ is 5-OMe |
| 27 | A is A-1d, $(R^2)_n$ is 5-NO$_2$ |
| 28 | A is A-1d, $(R^2)_n$ is 4-F |
| 29 | A is A-1d, $(R^2)_n$ is 4-Cl |
| 30 | A is A-1d, $(R^2)_n$ is 4-Me |
| 31 | A is A-1d, $(R^2)_n$ is 4,5-di-F |
| 32 | A is A-1d, $(R^2)_n$ is 4,5-di-Cl |
| 33 | A is A-1f, $(R^2)_n$ is H (n is 0) |
| 34 | A is A-1f, $(R^2)_n$ is 5-F |
| 35 | A is A-1f, $(R^2)_n$ is 5-Cl |
| 36 | A is A-1f, $(R^2)_n$ is 5-Br |
| 37 | A is A-1f, $(R^2)_n$ is 5-I |
| 38 | A is A-1f, $(R^2)_n$ is 5-Me |
| 39 | A is A-1f, $(R^2)_n$ is 5-Et |
| 40 | A is A-1f, $(R^2)_n$ is 5-CF$_3$ |
| 41 | A is A-1f, $(R^2)_n$ is 5-CN |
| 42 | A is A-1f, $(R^2)_n$ is 5-OMe |
| 43 | A is A-1f, $(R^2)_n$ is 5-NO$_2$ |
| 44 | A is A-1f, $(R^2)_n$ is 4-F |
| 45 | A is A-1f, $(R^2)_n$ is 4-Cl |
| 46 | A is A-1f, $(R^2)_n$ is 4-Me |
| 47 | A is A-1f, $(R^2)_n$ is 4,5-di-F |
| 48 | A is A-1f, $(R^2)_n$ is 4,5-di-Cl |
| 49 | A is A-1h, $(R^2)_n$ is H (n is 0) |
| 50 | A is A-1h, $(R^2)_n$ is 5-F |

-continued

| Table | Row heading |
|---|---|
| 51 | A is A-1h, $(R^2)_n$ is 5-Cl |
| 52 | A is A-1h, $(R^2)_n$ is 5-Br |
| 53 | A is A-1h, $(R^2)_n$ is 5-I |
| 54 | A is A-1h, $(R^2)_n$ is 5-Me |
| 55 | A is A-1h, $(R^2)_n$ is 5-Et |
| 56 | A is A-1h, $(R^2)_n$ is 5-CF$_3$ |
| 57 | A is A-1h, $(R^2)_n$ is 5-CN |
| 58 | A is A-1h, $(R^2)_n$ is 5-OMe |
| 59 | A is A-1h, $(R^2)_n$ is 5-NO$_2$ |
| 60 | A is A-1h, $(R^2)_n$ is 4-F |
| 61 | A is A-1h, $(R^2)_n$ is 4-Cl |
| 62 | A is A-1h, $(R^2)_n$ is 4-Me |
| 63 | A is A-1h, $(R^2)_n$ is 4,5-di-F |
| 64 | A is A-1h, $(R^2)_n$ is 4,5-di-Cl |
| 65 | A is A-1k, $(R^2)_n$ is H (n is 0) |
| 66 | A is A-1k, $(R^2)_n$ is 5-F |
| 67 | A is A-1k, $(R^2)_n$ is 5-Cl |
| 68 | A is A-1k, $(R^2)_n$ is 5-Br |
| 69 | A is A-1k, $(R^2)_n$ is 5-I |
| 70 | A is A-1k, $(R^2)_n$ is 5-Me |
| 71 | A is A-1k, $(R^2)_n$ is 5-Et |
| 72 | A is A-1k, $(R^2)_n$ is 5-CF$_3$ |
| 73 | A is A-1k, $(R^2)_n$ is 5-CN |
| 74 | A is A-1k, $(R^2)_n$ is 5-OMe |
| 75 | A is A-1k, $(R^2)_n$ is 5-NO$_2$ |
| 76 | A is A-1k, $(R^2)_n$ is 4-F |
| 77 | A is A-1k, $(R^2)_n$ is 4-Cl |
| 78 | A is A-1k, $(R^2)_n$ is 4-Me |
| 79 | A is A-1k, $(R^2)_n$ is 4,5-di-F |
| 80 | A is A-1k, $(R^2)_n$ is 4,5-di-Cl |
| 81 | A is A-1l, $(R^2)_n$ is H (n is 0) |
| 82 | A is A-1l, $(R^2)_n$ is 5-F |
| 83 | A is A-1l, $(R^2)_n$ is 5-Cl |
| 84 | A is A-1l, $(R^2)_n$ is 5-Br |
| 85 | A is A-1l, $(R^2)_n$ is 5-I |
| 86 | A is A-1l, $(R^2)_n$ is 5-Me |
| 87 | A is A-1l, $(R^2)_n$ is 5-Et |
| 88 | A is A-1l, $(R^2)_n$ is 5-CF$_3$ |
| 89 | A is A-1l, $(R^2)_n$ is 5-CN |
| 90 | A is A-1l, $(R^2)_n$ is 5-OMe |
| 91 | A is A-1l, $(R^2)_n$ is 5-NO$_2$ |
| 92 | A is A-1l, $(R^2)_n$ is 4-F |
| 93 | A is A-1l, $(R^2)_n$ is 4-Cl |
| 94 | A is A-1l, $(R^2)_n$ is 4-Me |
| 95 | A is A-1l, $(R^2)_n$ is 4,5-di-F |
| 96 | A is A-1l, $(R^2)_n$ is 4,5-di-Cl |
| 97 | A is A-2a, $(R^2)_n$ is H (n is 0) |
| 98 | A is A-2a, $(R^2)_n$ is 5-F |
| 99 | A is A-2a, $(R^2)_n$ is 5-Cl |
| 100 | A is A-2a, $(R^2)_n$ is 5-Br |
| 101 | A is A-2a, $(R^2)_n$ is 5-I |
| 102 | A is A-2a, $(R^2)_n$ is 5-Me |
| 103 | A is A-2a, $(R^2)_n$ is 5-Et |
| 104 | A is A-2a, $(R^2)_n$ is 5-CF$_3$ |
| 105 | A is A-2a, $(R^2)_n$ is 5-CN |
| 106 | A is A-2a, $(R^2)_n$ is 5-OMe |
| 107 | A is A-2a, $(R^2)_n$ is 5-NO$_2$ |
| 108 | A is A-2a, $(R^2)_n$ is 4-F |
| 109 | A is A-2a, $(R^2)_n$ is 4-Cl |
| 110 | A is A-2a, $(R^2)_n$ is 4-Me |
| 111 | A is A-2a, $(R^2)_n$ is 4,5-di-F |
| 112 | A is A-2a, $(R^2)_n$ is 4,5-di-Cl |
| 113 | A is A-2b, $(R^2)_n$ is H (n is 0) |
| 114 | A is A-2b, $(R^2)_n$ is 5-F |
| 115 | A is A-2b, $(R^2)_n$ is 5-Cl |
| 116 | A is A-2b, $(R^2)_n$ is 5-Br |
| 117 | A is A-2b, $(R^2)_n$ is 5-I |
| 118 | A is A-2b, $(R^2)_n$ is 5-Me |
| 119 | A is A-2b, $(R^2)_n$ is 5-Et |
| 120 | A is A-2b, $(R^2)_n$ is 5-CF$_3$ |
| 121 | A is A-2b, $(R^2)_n$ is 5-CN |
| 122 | A is A-2b, $(R^2)_n$ is 5-OMe |
| 123 | A is A-2b, $(R^2)_n$ is 5-NO$_2$ |
| 124 | A is A-2b, $(R^2)_n$ is 4-F |
| 125 | A is A-2b, $(R^2)_n$ is 4-Cl |
| 126 | A is A-2b, $(R^2)_n$ is 4-Me |
| 127 | A is A-2b, $(R^2)_n$ is 4,5-di-F |
| 128 | A is A-2b, $(R^2)_n$ is 4,5-di-Cl |
| 129 | A is A-2c, $(R^2)_n$ is H (n is 0) |
| 130 | A is A-2c, $(R^2)_n$ is 5-F |
| 131 | A is A-2c, $(R^2)_n$ is 5-Cl |
| 132 | A is A-2c, $(R^2)_n$ is 5-Br |
| 133 | A is A-2c, $(R^2)_n$ is 5-I |
| 134 | A is A-2c, $(R^2)_n$ is 5-Me |
| 135 | A is A-2c, $(R^2)_n$ is 5-Et |
| 136 | A is A-2c, $(R^2)_n$ is 5-CF$_3$ |
| 137 | A is A-2c, $(R^2)_n$ is 5-CN |
| 138 | A is A-2c, $(R^2)_n$ is 5-OMe |
| 139 | A is A-2c, $(R^2)_n$ is 5-NO$_2$ |
| 140 | A is A-2c, $(R^2)_n$ is 4-F |
| 141 | A is A-2c, $(R^2)_n$ is 4-Cl |
| 142 | A is A-2c, $(R^2)_n$ is 4-Me |
| 143 | A is A-2c, $(R^2)_n$ is 4,5-di-F |
| 144 | A is A-2c, $(R^2)_n$ is 4,5-di-Cl |
| 145 | A is A-2d, $(R^2)_n$ is H (n is 0) |
| 146 | A is A-2d, $(R^2)_n$ is 5-F |
| 147 | A is A-2d, $(R^2)_n$ is 5-Cl |
| 148 | A is A-2d, $(R^2)_n$ is 5-Br |
| 149 | A is A-2d, $(R^2)_n$ is 5-I |
| 150 | A is A-2d, $(R^2)_n$ is 5-Me |
| 151 | A is A-2d, $(R^2)_n$ is 5-Et |
| 152 | A is A-2d, $(R^2)_n$ is 5-CF$_3$ |
| 153 | A is A-2d, $(R^2)_n$ is 5-CN |
| 154 | A is A-2d, $(R^2)_n$ is 5-OMe |
| 155 | A is A-2d, $(R^2)_n$ is 5-NO$_2$ |
| 156 | A is A-2d, $(R^2)_n$ is 4-F |
| 157 | A is A-2d, $(R^2)_n$ is 4-Cl |
| 158 | A is A-2d, $(R^2)_n$ is 4-Me |
| 159 | A is A-2d, $(R^2)_n$ is 4,5-di-F |
| 160 | A is A-2d, $(R^2)_n$ is 4,5-di-Cl |
| 161 | A is A-3b, $(R^2)_n$ is H (n is 0) |
| 162 | A is A-3b, $(R^2)_n$ is 5-F |
| 163 | A is A-3b, $(R^2)_n$ is 5-Cl |
| 164 | A is A-3b, $(R^2)_n$ is 5-Br |
| 165 | A is A-3b, $(R^2)_n$ is 5-I |
| 166 | A is A-3b, $(R^2)_n$ is 5-Me |
| 167 | A is A-3b, $(R^2)_n$ is 5-Et |
| 168 | A is A-3b, $(R^2)_n$ is 5-CF$_3$ |
| 169 | A is A-3b, $(R^2)_n$ is 5-CN |
| 170 | A is A-3b, $(R^2)_n$ is 5-OMe |
| 171 | A is A-3b, $(R^2)_n$ is 5-NO$_2$ |
| 172 | A is A-3b, $(R^2)_n$ is 4-F |
| 173 | A is A-3b, $(R^2)_n$ is 4-Cl |
| 174 | A is A-3b, $(R^2)_n$ is 4-Me |
| 175 | A is A-3b, $(R^2)_n$ is 4,5-di-F |
| 176 | A is A-3b, $(R^2)_n$ is 4,5-di-Cl |
| 177 | A is A-3c, $(R^2)_n$ is H (n is 0) |
| 178 | A is A-3c, $(R^2)_n$ is 5-F |
| 179 | A is A-3c, $(R^2)_n$ is 5-Cl |
| 180 | A is A-3c, $(R^2)_n$ is 5-Br |
| 181 | A is A-3c, $(R^2)_n$ is 5-I |
| 182 | A is A-3c, $(R^2)_n$ is 5-Me |
| 183 | A is A-3c, $(R^2)_n$ is 5-Et |
| 184 | A is A-3c, $(R^2)_n$ is 5-CF$_3$ |
| 185 | A is A-3c, $(R^2)_n$ is 5-CN |
| 186 | A is A-3c, $(R^2)_n$ is 5-OMe |
| 187 | A is A-3c, $(R^2)_n$ is 5-NO$_2$ |
| 188 | A is A-3c, $(R^2)_n$ is 4-F |
| 189 | A is A-3c, $(R^2)_n$ is 4-Cl |
| 190 | A is A-3c, $(R^2)_n$ is 4-Me |
| 191 | A is A-3c, $(R^2)_n$ is 4,5-di-F |
| 192 | A is A-3c, $(R^2)_n$ is 4,5-di-Cl |
| 193 | A is A-4a, $(R^2)_n$ is H (n is 0) |
| 194 | A is A-4a, $(R^2)_n$ is 5-F |
| 195 | A is A-4a, $(R^2)_n$ is 5-Cl |
| 196 | A is A-4a, $(R^2)_n$ is 5-Br |
| 197 | A is A-4a, $(R^2)_n$ is 5-I |
| 198 | A is A-4a, $(R^2)_n$ is 5-Me |
| 199 | A is A-4a, $(R^2)_n$ is 5-Et |
| 200 | A is A-4a, $(R^2)_n$ is 5-CF$_3$ |
| 201 | A is A-4a, $(R^2)_n$ is 5-CN |
| 202 | A is A-4a, $(R^2)_n$ is 5-OMe |
| 203 | A is A-4a, $(R^2)_n$ is 5-NO$_2$ |
| 204 | A is A-4a, $(R^2)_n$ is 4-F |

-continued

| Table | Row heading |
|---|---|
| 205 | A is A-4a, $(R^2)_n$ is 4-Cl |
| 206 | A is A-4a, $(R^2)_n$ is 4-Me |
| 207 | A is A-4a, $(R^2)_n$ is 4,5-di-F |
| 208 | A is A-4a, $(R^2)_n$ is 4,5-di-Cl |
| 209 | A is A-6c, $(R^2)_n$ is H (n is 0) |
| 210 | A is A-6c, $(R^2)_n$ is 5-F |
| 211 | A is A-6c, $(R^2)_n$ is 5-Cl |
| 212 | A is A-6c, $(R^2)_n$ is 5-Br |
| 213 | A is A-6c, $(R^2)_n$ is 5-I |
| 214 | A is A-6c, $(R^2)_n$ is 5-Me |
| 215 | A is A-6c, $(R^2)_n$ is 5-Et |
| 216 | A is A-6c, $(R^2)_n$ is 5-$CF_3$ |
| 217 | A is A-6c, $(R^2)_n$ is 5-CN |
| 218 | A is A-6c, $(R^2)_n$ is 5-OMe |
| 219 | A is A-6c, $(R^2)_n$ is 5-$NO_2$ |
| 220 | A is A-6c, $(R^2)_n$ is 4-F |
| 221 | A is A-6c, $(R^2)_n$ is 4-Cl |
| 222 | A is A-6c, $(R^2)_n$ is 4-Me |
| 223 | A is A-6c, $(R^2)_n$ is 4,5-di-F |
| 224 | A is A-6c, $(R^2)_n$ is 4,5-di-Cl |
| 225 | A is A-7a, $(R^2)_n$ is H (n is 0) |
| 226 | A is A-7a, $(R^2)_n$ is 5-F |
| 227 | A is A-7a, $(R^2)_n$ is 5-Cl |
| 228 | A is A-7a, $(R^2)_n$ is 5-Br |
| 229 | A is A-7a, $(R^2)_n$ is 5-I |
| 230 | A is A-7a, $(R^2)_n$ is 5-Me |
| 231 | A is A-7a, $(R^2)_n$ is 5-Et |
| 232 | A is A-7a, $(R^2)_n$ is 5-$CF_3$ |
| 233 | A is A-7a, $(R^2)_n$ is 5-CN |
| 234 | A is A-7a, $(R^2)_n$ is 5-OMe |
| 235 | A is A-7a, $(R^2)_n$ is 5-$NO_2$ |
| 236 | A is A-7a, $(R^2)_n$ is 4-F |
| 237 | A is A-7a, $(R^2)_n$ is 4-Cl |
| 238 | A is A-7a, $(R^2)_n$ is 4-Me |
| 239 | A is A-7a, $(R^2)_n$ is 4,5-di-F |
| 240 | A is A-7a, $(R^2)_n$ is 4,5-di-Cl |
| 241 | A is A-8a, $(R^2)_n$ is H (n is 0) |
| 242 | A is A-8a, $(R^2)_n$ is 5-F |
| 243 | A is A-8a, $(R^2)_n$ is 5-Cl |
| 244 | A is A-8a, $(R^2)_n$ is 5-Br |
| 245 | A is A-8a, $(R^2)_n$ is 5-I |
| 246 | A is A-8a, $(R^2)_n$ is 5-Me |
| 247 | A is A-8a, $(R^2)_n$ is 5-Et |
| 248 | A is A-8a, $(R^2)_n$ is 5-$CF_3$ |
| 249 | A is A-8a, $(R^2)_n$ is 5-CN |
| 250 | A is A-8a, $(R^2)_n$ is 5-OMe |
| 251 | A is A-8a, $(R^2)_n$ is 5-$NO_2$ |
| 252 | A is A-8a, $(R^2)_n$ is 4-F |
| 253 | A is A-8a, $(R^2)_n$ is 4-Cl |
| 254 | A is A-8a, $(R^2)_n$ is 4-Me |
| 255 | A is A-8a, $(R^2)_n$ is 4,5-di-F |
| 256 | A is A-8a, $(R^2)_n$ is 4,5-di-Cl |
| 257 | A is A-8b, $(R^2)_n$ is H (n is 0) |
| 258 | A is A-8b, $(R^2)_n$ is 5-F |
| 259 | A is A-8b, $(R^2)_n$ is 5-Cl |
| 260 | A is A-8b, $(R^2)_n$ is 5-Br |
| 261 | A is A-8b, $(R^2)_n$ is 5-I |
| 262 | A is A-8b, $(R^2)_n$ is 5-Me |
| 263 | A is A-8b, $(R^2)_n$ is 5-Et |
| 264 | A is A-8b, $(R^2)_n$ is 5-$CF_3$ |
| 265 | A is A-8b, $(R^2)_n$ is 5-CN |
| 266 | A is A-8b, $(R^2)_n$ is 5-OMe |
| 267 | A is A-8b, $(R^2)_n$ is 5-$NO_2$ |
| 268 | A is A-8b, $(R^2)_n$ is 4-F |
| 269 | A is A-8b, $(R^2)_n$ is 4-Cl |
| 270 | A is A-8b, $(R^2)_n$ is 4-Me |
| 271 | A is A-8b, $(R^2)_n$ is 4,5-di-F |
| 272 | A is A-8b, $(R^2)_n$ is 4,5-di-Cl |

TABLE 273

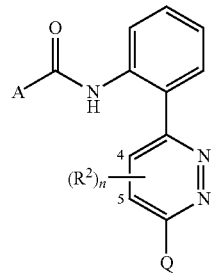

Table 273 is constructed in the same manner as Table 1 except that the chemical structure in Table 1 is replaced with the following structure:
wherein A is A-1a; n is 0; and each Q is selected from the individual values listed in Exhibit B. Therefore, the first entry in Table 273 is a compound of Formula 1 wherein Z is O; $R^1$ is H; L is 1,2-phenylene; G is G-3; n is 0; and Q is 3-$CF_3$-pyrazol-1-yl. The second entry in Table 273 is a compound of Formula 1 wherein Z is O; $R^1$ is H; L is 1,2-phenylene; G is G-3; A is A-1a; n is 0; and Q is 4-$CF_3$-1H-pyrazol-1-yl. The remaining entries in Table 273 are constructed in the same manner.

Table 274 is constructed in the same fashion as Table 2. Tables 275 through 544 are constructed similarly to the corresponding Table listed in the following chart.

| Table | Constructed as in Table: |
|---|---|
| 273 | 1 |
| 274 | 2 |
| 275 | 3 |
| 276 | 4 |
| 277 | 5 |
| 278 | 6 |
| 279 | 7 |
| 280 | 8 |
| 281 | 9 |
| 282 | 10 |
| 283 | 11 |
| 284 | 12 |
| 285 | 13 |
| 286 | 14 |
| 287 | 15 |
| 288 | 16 |
| 289 | 17 |
| 290 | 18 |
| 291 | 19 |
| 292 | 20 |
| 293 | 21 |
| 294 | 22 |
| 295 | 23 |
| 296 | 24 |
| 297 | 25 |
| 298 | 26 |
| 299 | 27 |
| 300 | 28 |
| 301 | 29 |
| 302 | 30 |
| 303 | 31 |
| 304 | 32 |
| 305 | 33 |
| 306 | 34 |
| 307 | 35 |
| 308 | 36 |
| 309 | 37 |
| 310 | 38 |
| 311 | 39 |
| 312 | 40 |
| 313 | 41 |
| 314 | 42 |

-continued

| Table | Constructed as in Table: |
|---|---|
| 315 | 43 |
| 316 | 44 |
| 317 | 45 |
| 318 | 46 |
| 319 | 47 |
| 320 | 48 |
| 321 | 49 |
| 322 | 50 |
| 323 | 51 |
| 324 | 52 |
| 325 | 53 |
| 326 | 54 |
| 327 | 55 |
| 328 | 56 |
| 329 | 57 |
| 330 | 58 |
| 331 | 59 |
| 332 | 60 |
| 333 | 61 |
| 334 | 62 |
| 335 | 63 |
| 336 | 64 |
| 337 | 65 |
| 338 | 66 |
| 339 | 67 |
| 340 | 68 |
| 341 | 69 |
| 342 | 70 |
| 343 | 71 |
| 344 | 72 |
| 345 | 73 |
| 346 | 74 |
| 347 | 75 |
| 348 | 76 |
| 349 | 77 |
| 350 | 78 |
| 351 | 79 |
| 352 | 80 |
| 353 | 81 |
| 354 | 82 |
| 355 | 83 |
| 356 | 84 |
| 357 | 85 |
| 358 | 86 |
| 359 | 87 |
| 360 | 88 |
| 361 | 89 |
| 362 | 90 |
| 363 | 91 |
| 364 | 92 |
| 365 | 93 |
| 366 | 94 |
| 367 | 95 |
| 368 | 96 |
| 369 | 97 |
| 370 | 98 |
| 371 | 99 |
| 372 | 100 |
| 373 | 101 |
| 374 | 102 |
| 375 | 103 |
| 376 | 104 |
| 377 | 105 |
| 378 | 106 |
| 379 | 107 |
| 380 | 108 |
| 381 | 109 |
| 382 | 110 |
| 383 | 111 |
| 384 | 112 |
| 385 | 113 |
| 386 | 114 |
| 387 | 115 |
| 388 | 116 |
| 389 | 117 |
| 390 | 118 |
| 391 | 119 |
| 392 | 120 |
| 393 | 121 |
| 394 | 122 |
| 395 | 123 |
| 396 | 124 |
| 397 | 125 |
| 398 | 126 |
| 399 | 127 |
| 400 | 128 |
| 401 | 129 |
| 402 | 130 |
| 403 | 131 |
| 404 | 132 |
| 405 | 133 |
| 406 | 134 |
| 407 | 135 |
| 408 | 136 |
| 409 | 137 |
| 410 | 138 |
| 411 | 139 |
| 412 | 140 |
| 413 | 141 |
| 414 | 142 |
| 415 | 143 |
| 416 | 144 |
| 417 | 145 |
| 418 | 146 |
| 419 | 147 |
| 420 | 148 |
| 421 | 149 |
| 422 | 150 |
| 423 | 151 |
| 424 | 152 |
| 425 | 153 |
| 426 | 154 |
| 427 | 155 |
| 428 | 156 |
| 429 | 157 |
| 430 | 158 |
| 431 | 159 |
| 432 | 160 |
| 433 | 161 |
| 434 | 162 |
| 435 | 163 |
| 436 | 164 |
| 437 | 165 |
| 438 | 166 |
| 439 | 167 |
| 440 | 168 |
| 441 | 169 |
| 442 | 170 |
| 443 | 171 |
| 444 | 172 |
| 445 | 173 |
| 446 | 174 |
| 447 | 175 |
| 448 | 176 |
| 449 | 177 |
| 450 | 178 |
| 451 | 179 |
| 452 | 180 |
| 453 | 181 |
| 454 | 182 |
| 455 | 183 |
| 456 | 184 |
| 457 | 185 |
| 458 | 186 |
| 459 | 187 |
| 460 | 188 |
| 461 | 189 |
| 462 | 190 |
| 463 | 191 |
| 464 | 192 |
| 465 | 193 |
| 466 | 194 |
| 467 | 195 |
| 468 | 196 |

TABLE 545 continued

| Table | Constructed as in Table: |
|---|---|
| 469 | 197 |
| 470 | 198 |
| 471 | 199 |
| 472 | 200 |
| 473 | 201 |
| 474 | 202 |
| 475 | 203 |
| 476 | 204 |
| 477 | 205 |
| 478 | 206 |
| 479 | 207 |
| 480 | 208 |
| 481 | 209 |
| 482 | 210 |
| 483 | 211 |
| 484 | 212 |
| 485 | 213 |
| 486 | 214 |
| 487 | 215 |
| 488 | 216 |
| 489 | 217 |
| 490 | 218 |
| 491 | 219 |
| 492 | 220 |
| 493 | 221 |
| 494 | 222 |
| 495 | 223 |
| 496 | 224 |
| 497 | 225 |
| 498 | 226 |
| 499 | 227 |
| 500 | 228 |
| 501 | 229 |
| 502 | 230 |
| 503 | 231 |
| 504 | 232 |
| 505 | 233 |
| 506 | 234 |
| 507 | 235 |
| 508 | 236 |
| 509 | 237 |
| 510 | 238 |
| 511 | 239 |
| 512 | 240 |
| 513 | 241 |
| 514 | 242 |
| 515 | 243 |
| 516 | 244 |
| 517 | 245 |
| 518 | 246 |
| 519 | 247 |
| 520 | 248 |
| 521 | 249 |
| 522 | 250 |
| 523 | 251 |
| 524 | 252 |
| 525 | 253 |
| 526 | 254 |
| 527 | 255 |
| 528 | 256 |
| 529 | 257 |
| 530 | 258 |
| 531 | 259 |
| 532 | 260 |
| 533 | 261 |
| 534 | 262 |
| 535 | 263 |
| 536 | 264 |
| 537 | 265 |
| 538 | 266 |
| 539 | 267 |
| 540 | 268 |
| 541 | 269 |
| 542 | 270 |
| 543 | 271 |
| 544 | 272 |

TABLE 545

Table 545 is constructed in the same fashion as Table 1 except the chemical structure is replaced with the following structure:

wherein A is A-1a; n is 0; and each Q is selected from the individual values listed in Exhibit B. Therefore, the first entry in Table 545 is a compound of Formula 1 wherein Z is O; $R^1$ is H; L is 1,2-phenylene; G is G-2; A is A-1a; n is 0; and Q is 3-$CF_3$-pyrazol-1-yl. The second entry in Table 545 is a compound of Formula 1 wherein Z is O; $R^1$ is H; L is 1,2-phenylene; G is G-2; A is A-1a; n is 0; and Q is 4-$CF_3$-1H-pyrazol-1-yl. The remaining entries in Table 545 are constructed in the same manner.

Table 546 is constructed in the same fashion as Table 545 except that the Header Row phrase "A is A-1a; n is 0" is replaced with phrase "A is A-1a; $(R^2)_n$ is 6-F" (i.e. n is 1). Tables 547 through 710 are constructed similarly.

| | |
|---|---|
| 546 | A is A-1a, $(R^2)_n$ is 6-F |
| 547 | A is A-1a, $(R^2)_n$ is 6-Cl |
| 548 | A is A-1a, $(R^2)_n$ is 6-Br |
| 549 | A is A-1a, $(R^2)_n$ is 6-I |
| 550 | A is A-1a, $(R^2)_n$ is 6-Me |
| 551 | A is A-1a, $(R^2)_n$ is 6-Et |
| 552 | A is A-1a, $(R^2)_n$ is 6-$CF_3$ |
| 553 | A is A-1a, $(R^2)_n$ is 6-CN |
| 554 | A is A-1a, $(R^2)_n$ is 6-OMe |
| 555 | A is A-1a, $(R^2)_n$ is 6-$NO_2$ |
| 556 | A is A-1d, $(R^2)_n$ is H (n is 0) |
| 557 | A is A-1d, $(R^2)_n$ is 6-F |
| 558 | A is A-1d, $(R^2)_n$ is 6-Cl |
| 559 | A is A-1d, $(R^2)_n$ is 6-Br |
| 560 | A is A-1d, $(R^2)_n$ is 6-I |
| 561 | A is A-1d, $(R^2)_n$ is 6-Me |
| 562 | A is A-1d, $(R^2)_n$ is 6-Et |
| 563 | A is A-1d, $(R^2)_n$ is 6-$CF_3$ |
| 564 | A is A-1d, $(R^2)_n$ is 6-CN |
| 565 | A is A-1d, $(R^2)_n$ is 6-OMe |
| 566 | A is A-1d, $(R^2)_n$ is 6-$NO_2$ |
| 567 | A is A-1f, $(R^2)_n$ is H (n is 0) |
| 568 | A is A-1f, $(R^2)_n$ is 6-F |
| 569 | A is A-1f, $(R^2)_n$ is 6-Cl |
| 570 | A is A-1f, $(R^2)_n$ is 6-Br |
| 571 | A is A-1f, $(R^2)_n$ is 6-I |
| 572 | A is A-1f, $(R^2)_n$ is 6-Me |
| 573 | A is A-1f, $(R^2)_n$ is 6-Et |
| 574 | A is A-1f, $(R^2)_n$ is 6-$CF_3$ |
| 575 | A is A-1f, $(R^2)_n$ is 6-CN |
| 576 | A is A-1f, $(R^2)_n$ is 6-OMe |
| 577 | A is A-1f, $(R^2)_n$ is 6-$NO_2$ |
| 578 | A is A-1h, $(R^2)_n$ is H (n is 0) |
| 579 | A is A-1h, $(R^2)_n$ is 6-F |
| 580 | A is A-1h, $(R^2)_n$ is 6-Cl |
| 581 | A is A-1h, $(R^2)_n$ is 6-Br |
| 582 | A is A-1h, $(R^2)_n$ is 6-I |
| 583 | A is A-1h, $(R^2)_n$ is 6-Me |
| 584 | A is A-1h, $(R^2)_n$ is 6-Et |
| 585 | A is A-1h, $(R^2)_n$ is 6-$CF_3$ |
| 586 | A is A-1h, $(R^2)_n$ is 6-CN |
| 587 | A is A-1h, $(R^2)_n$ is 6-OMe |
| 588 | A is A-1h, $(R^2)_n$ is 6-$NO_2$ |

| | |
|---|---|
| 589 | A is A-2a, $(R^2)_n$ is H (n is 0) |
| 590 | A is A-2a, $(R^2)_n$ is 6-F |
| 591 | A is A-2a, $(R^2)_n$ is 6-Cl |
| 592 | A is A-2a, $(R^2)_n$ is 6-Br |
| 593 | A is A-2a, $(R^2)_n$ is 6-I |
| 594 | A is A-2a, $(R^2)_n$ is 6-Me |
| 595 | A is A-2a, $(R^2)_n$ is 6-Et |
| 596 | A is A-2a, $(R^2)_n$ is 6-CF$_3$ |
| 597 | A is A-2a, $(R^2)_n$ is 6-CN |
| 598 | A is A-2a, $(R^2)_n$ is 6-OMe |
| 599 | A is A-2a, $(R^2)_n$ is 6-NO$_2$ |
| 600 | A is A-2b, $(R^2)_n$ is H (n is 0) |
| 601 | A is A-2b, $(R^2)_n$ is 6-F |
| 602 | A is A-2b, $(R^2)_n$ is 6-Cl |
| 603 | A is A-2b, $(R^2)_n$ is 6-Br |
| 604 | A is A-2b, $(R^2)_n$ is 6-I |
| 605 | A is A-2b, $(R^2)_n$ is 6-Me |
| 606 | A is A-2b, $(R^2)_n$ is 6-Et |
| 607 | A is A-2b, $(R^2)_n$ is 6-CF$_3$ |
| 608 | A is A-2b, $(R^2)_n$ is 6-CN |
| 609 | A is A-2b, $(R^2)_n$ is 6-OMe |
| 610 | A is A-2b, $(R^2)_n$ is 6-NO$_2$ |
| 611 | A is A-2c, $(R^2)_n$ is H (n is 0) |
| 612 | A is A-2c, $(R^2)_n$ is 6-F |
| 613 | A is A-2c, $(R^2)_n$ is 6-Cl |
| 614 | A is A-2c, $(R^2)_n$ is 6-Br |
| 615 | A is A-2c, $(R^2)_n$ is 6-I |
| 616 | A is A-2c, $(R^2)_n$ is 6-Me |
| 617 | A is A-2c, $(R^2)_n$ is 6-Et |
| 618 | A is A-2c, $(R^2)_n$ is 6-CF$_3$ |
| 619 | A is A-2c, $(R^2)_n$ is 6-CN |
| 620 | A is A-2c, $(R^2)_n$ is 6-OMe |
| 621 | A is A-2c, $(R^2)_n$ is 6-NO$_2$ |
| 622 | A is A-2d, $(R^2)_n$ is H (n is 0) |
| 623 | A is A-2d, $(R^2)_n$ is 6-F |
| 624 | A is A-2d, $(R^2)_n$ is 6-Cl |
| 625 | A is A-2d, $(R^2)_n$ is 6-Br |
| 626 | A is A-2d, $(R^2)_n$ is 6-I |
| 627 | A is A-2d, $(R^2)_n$ is 6-Me |
| 628 | A is A-2d, $(R^2)_n$ is 6-Et |
| 629 | A is A-2d, $(R^2)_n$ is 6-CF3 |
| 630 | A is A-2d, $(R^2)_n$ is 6-CN |
| 631 | A is A-2d, $(R^2)_n$ is 6-OMe |
| 632 | A is A-2d, $(R^2)_n$ is 6-NO$_2$ |
| 633 | A is A-3b, $(R^2)_n$ is H (n is 0) |
| 634 | A is A-3b, $(R^2)_n$ is 6-F |
| 635 | A is A-3b, $(R^2)_n$ is 6-Cl |
| 636 | A is A-3b, $(R^2)_n$ is 6-Br |
| 637 | A is A-3b, $(R^2)_n$ is 6-I |
| 638 | A is A-3b, $(R^2)_n$ is 6-Me |
| 639 | A is A-3b, $(R^2)_n$ is 6-Et |
| 640 | A is A-3b, $(R^2)_n$ is 6-CF$_3$ |
| 641 | A is A-3b, $(R^2)_n$ is 6-CN |
| 642 | A is A-3b, $(R^2)_n$ is 6-OMe |
| 643 | A is A-3b, $(R^2)_n$ is 6-NO$_2$ |
| 644 | A is A-3c, $(R^2)_n$ is H (n is 0) |
| 645 | A is A-3c, $(R^2)_n$ is 6-F |
| 646 | A is A-3c, $(R^2)_n$ is 6-Cl |
| 647 | A is A-3c, $(R^2)_n$ is 6-Br |
| 648 | A is A-3c, $(R^2)_n$ is 6-I |
| 649 | A is A-3c, $(R^2)_n$ is 6-Me |
| 650 | A is A-3c, $(R^2)_n$ is 6-Et |
| 651 | A is A-3c, $(R^2)_n$ is 6-CF$_3$ |
| 652 | A is A-3c, $(R^2)_n$ is 6-CN |
| 653 | A is A-3c, $(R^2)_n$ is 6-OMe |
| 654 | A is A-3c, $(R^2)_n$ is 6-NO$_2$ |
| 655 | A is A-4a, $(R^2)_n$ is H (n is 0) |
| 656 | A is A-4a, $(R^2)_n$ is 6-F |
| 657 | A is A-4a, $(R^2)_n$ is 6-Cl |
| 658 | A is A-4a, $(R^2)_n$ is 6-Br |
| 659 | A is A-4a, $(R^2)_n$ is 6-I |
| 660 | A is A-4a, $(R^2)_n$ is 6-Me |
| 661 | A is A-4a, $(R^2)_n$ is 6-Et |
| 662 | A is A-4a, $(R^2)_n$ is 6-CF$_3$ |
| 663 | A is A-4a, $(R^2)_n$ is 6-CN |
| 664 | A is A-4a, $(R^2)_n$ is 6-OMe |
| 665 | A is A-4a, $(R^2)_n$ is 6-NO$_2$ |
| 666 | A is A-6c, $(R^2)_n$ is H (n is 0) |
| 667 | A is A-6c, $(R^2)_n$ is 6-F |
| 668 | A is A-6c, $(R^2)_n$ is 6-Cl |
| 669 | A is A-6c, $(R^2)_n$ is 6-Br |
| 670 | A is A-6c, $(R^2)_n$ is 6-I |
| 671 | A is A-6c, $(R^2)_n$ is 6-Me |
| 672 | A is A-6c, $(R^2)_n$ is 6-Et |
| 673 | A is A-6c, $(R^2)_n$ is 6-CF$_3$ |
| 674 | A is A-6c, $(R^2)_n$ is 6-CN |
| 675 | A is A-6c, $(R^2)_n$ is 6-OMe |
| 676 | A is A-6c, $(R^2)_n$ is 6-NO$_2$ |
| 677 | A is A-7a, $(R^2)_n$ is H (n is 0) |
| 678 | A is A-7a, $(R^2)_n$ is 6-F |
| 679 | A is A-7a, $(R^2)_n$ is 6-Cl |
| 680 | A is A-7a, $(R^2)_n$ is 6-Br |
| 681 | A is A-7a, $(R^2)_n$ is 6-I |
| 682 | A is A-7a, $(R^2)_n$ is 6-Me |
| 683 | A is A-7a, $(R^2)_n$ is 6-Et |
| 684 | A is A-7a, $(R^2)_n$ is 6-CF$_3$ |
| 685 | A is A-7a, $(R^2)_n$ is 6-CN |
| 686 | A is A-7a, $(R^2)_n$ is 6-OMe |
| 687 | A is A-7a, $(R^2)_n$ is 6-NO$_2$ |
| 688 | A is A-8a, $(R^2)_n$ is H (n is 0) |
| 689 | A is A-8a, $(R^2)_n$ is 6-F |
| 690 | A is A-8a, $(R^2)_n$ is 6-Cl |
| 691 | A is A-8a, $(R^2)_n$ is 6-Br |
| 692 | A is A-8a, $(R^2)_n$ is 6-I |
| 693 | A is A-8a, $(R^2)_n$ is 6-Me |
| 694 | A is A-8a, $(R^2)_n$ is 6-Et |
| 695 | A is A-8a, $(R^2)_n$ is 6-CF$_3$ |
| 696 | A is A-8a, $(R^2)_n$ is 6-CN |
| 697 | A is A-8a, $(R^2)_n$ is 6-OMe |
| 698 | A is A-8a, $(R^2)_n$ is 6-NO$_2$ |
| 699 | A is A-8b, $(R^2)_n$ is H (n is 0) |
| 700 | A is A-8b, $(R^2)_n$ is 6-F |
| 701 | A is A-8b, $(R^2)_n$ is 6-Cl |
| 702 | A is A-8b, $(R^2)_n$ is 6-Br |
| 703 | A is A-8b, $(R^2)_n$ is 6-I |
| 704 | A is A-8b, $(R^2)_n$ is 6-Me |
| 705 | A is A-8b, $(R^2)_n$ is 6-Et |
| 706 | A is A-8b, $(R^2)_n$ is 6-CF$_3$ |
| 707 | A is A-8b, $(R^2)_n$ is 6-CN |
| 708 | A is A-8b, $(R^2)_n$ is 6-OMe |
| 709 | A is A-8b, $(R^2)_n$ is 6-NO$_2$ |

TABLE 710

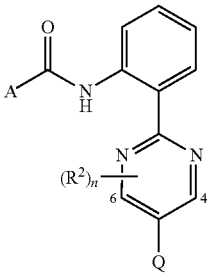

Table 710 is constructed in the same fashion as Table 1 except the chemical structure is replaced with the following structure:

wherein A is A-1a; n is 0; and Q is as defined in Exhibit B for Table 1. Therefore, the first entry in Table 710 is a compound of Formula 1 wherein Z is O; $R^1$ is H; L is 1,2-phenylene; G is G-5; A is A-1a; n is 0; and Q is 3-CF$_3$-pyrazol-1-yl. The second entry in Table 710 is a compound of Formula 1 wherein Z is O; $R^1$ is H; L is 1,2-phenylene; G is G-5; A is A-1a; n is 0; and Q is 4-CF$_3$-1H-pyrazol-1-yl. The remaining entries in Table 710 are constructed in the same manner. Tables 711 through 965 are constructed similarly.

| Table | Row Heading |
|---|---|
| 711 | A is A-1a, $(R^2)_n$ is 4-F |
| 712 | A is A-1a, $(R^2)_n$ is 4-Cl |
| 713 | A is A-1a, $(R^2)_n$ is 4-Br |
| 714 | A is A-1a, $(R^2)_n$ is 4-I |
| 715 | A is A-1a, $(R^2)_n$ is 4-Me |
| 716 | A is A-1a, $(R^2)_n$ is 4-Et |
| 717 | A is A-1a, $(R^2)_n$ is 4-CF$_3$ |
| 718 | A is A-1a, $(R^2)_n$ is 4-CN |
| 719 | A is A-1a, $(R^2)_n$ is 4-OMe |
| 720 | A is A-1a, $(R^2)_n$ is 4,6-di-F |
| 721 | A is A-1a, $(R^2)_n$ is 4,6-di-Cl |
| 722 | A is A-1a, $(R^2)_n$ is 4,6-di-Me |
| 723 | A is A-1a, $(R^2)_n$ is 4-Cl-6-F |
| 724 | A is A-1a, $(R^2)_n$ is 4-Cl-6-Me |
| 725 | A is A-1a, $(R^2)_n$ is 4-F-6-Me |
| 726 | A is A-1d, $(R^2)_n$ is H (n is 0) |
| 727 | A is A-1d, $(R^2)_n$ is 4-F |
| 728 | A is A-1d, $(R^2)_n$ is 4-Cl |
| 729 | A is A-1d, $(R^2)_n$ is 4-Br |
| 730 | A is A-1d, $(R^2)_n$ is 4-I |
| 731 | A is A-1d, $(R^2)_n$ is 4-Me |
| 732 | A is A-1d, $(R^2)_n$ is 4-Et |
| 733 | A is A-1d, $(R^2)_n$ is 4-CF$_3$ |
| 734 | A is A-1d, $(R^2)_n$ is 4-CN |
| 735 | A is A-1d, $(R^2)_n$ is 4-OMe |
| 736 | A is A-1d, $(R^2)_n$ is 4,6-di-F |
| 737 | A is A-1d, $(R^2)_n$ is 4,6-di-Cl |
| 738 | A is A-1d, $(R^2)_n$ is 4,6-di-Me |
| 739 | A is A-1d, $(R^2)_n$ is 4-Cl-6-F |
| 740 | A is A-1d, $(R^2)_n$ is 4-Cl-6-Me |
| 741 | A is A-1d, $(R^2)_n$ is 4-F-6-Me |
| 742 | A is A-1f, $(R^2)_n$ is H (n is 0) |
| 743 | A is A-1f, $(R^2)_n$ is 4-F |
| 744 | A is A-1f, $(R^2)_n$ is 4-Cl |
| 745 | A is A-1f, $(R^2)_n$ is 4-Br |
| 746 | A is A-1f, $(R^2)_n$ is 4-I |
| 747 | A is A-1f, $(R^2)_n$ is 4-Me |
| 748 | A is A-1f, $(R^2)_n$ is 4-Et |
| 749 | A is A-1f, $(R^2)_n$ is 4-CF$_3$ |
| 750 | A is A-1f, $(R^2)_n$ is 4-CN |
| 751 | A is A-1f, $(R^2)_n$ is 4-OMe |
| 752 | A is A-1f, $(R^2)_n$ is 4,6-di-F |
| 753 | A is A-1f, $(R^2)_n$ is 4,6-di-Cl |
| 754 | A is A-1f, $(R^2)_n$ is 4,6-di-Me |
| 755 | A is A-1f, $(R^2)_n$ is 4-Cl-6-F |
| 756 | A is A-1f, $(R^2)_n$ is 4-Cl-6-Me |
| 757 | A is A-1f, $(R^2)_n$ is 4-F-6-Me |
| 758 | A is A-1h, $(R^2)_n$ is H (n is 0) |
| 759 | A is A-1h, $(R^2)_n$ is 4-F |
| 760 | A is A-1h, $(R^2)_n$ is 4-Cl |
| 761 | A is A-1h, $(R^2)_n$ is 4-Br |
| 762 | A is A-1h, $(R^2)_n$ is 4-I |
| 763 | A is A-1h, $(R^2)_n$ is 4-Me |
| 764 | A is A-1h, $(R^2)_n$ is 4-Et |
| 765 | A is A-1h, $(R^2)_n$ is 4-CF$_3$ |
| 766 | A is A-1h, $(R^2)_n$ is 4-CN |
| 767 | A is A-1h, $(R^2)_n$ is 4-OMe |
| 768 | A is A-1h, $(R^2)_n$ is 4,6-di-F |
| 769 | A is A-1h, $(R^2)_n$ is 4,6-di-Cl |
| 770 | A is A-1h, $(R^2)_n$ is 4,6-di-Me |
| 771 | A is A-1h, $(R^2)_n$ is 4-Cl-6-F |
| 772 | A is A-1h, $(R^2)_n$ is 4-Cl-6-Me |
| 773 | A is A-1h, $(R^2)_n$ is 4-F-6-Me |
| 774 | A is A-1k, $(R^2)_n$ is H (n is 0) |
| 775 | A is A-1k, $(R^2)_n$ is 4-F |
| 776 | A is A-1k, $(R^2)_n$ is 4-Cl |
| 777 | A is A-1k, $(R^2)_n$ is 4-Br |
| 778 | A is A-1k, $(R^2)_n$ is 4-I |
| 779 | A is A-1k, $(R^2)_n$ is 4-Me |
| 780 | A is A-1k, $(R^2)_n$ is 4-Et |
| 781 | A is A-1k, $(R^2)_n$ is 4-CF$_3$ |
| 782 | A is A-1k, $(R^2)_n$ is 4-CN |
| 783 | A is A-1k, $(R^2)_n$ is 4-OMe |
| 784 | A is A-1k, $(R^2)_n$ is 4,6-di-F |
| 785 | A is A-1k, $(R^2)_n$ is 4,6-di-Cl |
| 786 | A is A-1k, $(R^2)_n$ is 4,6-di-Me |
| 787 | A is A-1k, $(R^2)_n$ is 4-Cl-6-F |
| 788 | A is A-1k, $(R^2)_n$ is 4-Cl-6-Me |
| 789 | A is A-1k, $(R^2)_n$ is 4-F-6-Me |
| 790 | A is A-1l, $(R^2)_n$ is H (n is 0) |
| 791 | A is A-1l, $(R^2)_n$ is 4-F |
| 792 | A is A-1l, $(R^2)_n$ is 4-Cl |
| 793 | A is A-1l, $(R^2)_n$ is 4-Br |
| 794 | A is A-1l, $(R^2)_n$ is 4-I |
| 795 | A is A-1l, $(R^2)_n$ is 4-Me |
| 796 | A is A-1l, $(R^2)_n$ is 4-Et |
| 797 | A is A-1l, $(R^2)_n$ is 4-CF$_3$ |
| 798 | A is A-1l, $(R^2)_n$ is 4-CN |
| 799 | A is A-1l, $(R^2)_n$ is 4-OMe |
| 800 | A is A-1l, $(R^2)_n$ is 4,6-di-F |
| 801 | A is A-1l, $(R^2)_n$ is 4,6-di-Cl |
| 802 | A is A-1l, $(R^2)_n$ is 4,6-di-Me |
| 803 | A is A-1l, $(R^2)_n$ is 4-Cl-6-F |
| 804 | A is A-1l, $(R^2)_n$ is 4-Cl-6-Me |
| 805 | A is A-1l, $(R^2)_n$ is 4-F-6-Me |
| 806 | A is A-2a, $(R^2)_n$ is H (n is 0) |
| 807 | A is A-2a, $(R^2)_n$ is 4-F |
| 808 | A is A-2a, $(R^2)_n$ is 4-Cl |
| 809 | A is A-2a, $(R^2)_n$ is 4-Br |
| 810 | A is A-2a, $(R^2)_n$ is 4-I |
| 811 | A is A-2a, $(R^2)_n$ is 4-Me |
| 812 | A is A-2a, $(R^2)_n$ is 4-Et |
| 813 | A is A-2a, $(R^2)_n$ is 4-CF$_3$ |
| 814 | A is A-2a, $(R^2)_n$ is 4-CN |
| 815 | A is A-2a, $(R^2)_n$ is 4-OMe |
| 816 | A is A-2a, $(R^2)_n$ is 4,6-di-F |
| 817 | A is A-2a, $(R^2)_n$ is 4,6-di-Cl |
| 818 | A is A-2a, $(R^2)_n$ is 4,6-di-Me |
| 819 | A is A-2a, $(R^2)_n$ is 4-Cl-6-F |
| 820 | A is A-2a, $(R^2)_n$ is 4-Cl-6-Me |
| 821 | A is A-2a, $(R^2)_n$ is 4-F-6-Me |
| 822 | A is A-2b, $(R^2)_n$ is H (n is 0) |
| 823 | A is A-2b, $(R^2)_n$ is 4-F |
| 824 | A is A-2b, $(R^2)_n$ is 4-Cl |
| 825 | A is A-2b, $(R^2)_n$ is 4-Br |
| 826 | A is A-2b, $(R^2)_n$ is 4-I |
| 827 | A is A-2b, $(R^2)_n$ is 4-Me |
| 828 | A is A-2b, $(R^2)_n$ is 4-Et |
| 829 | A is A-2b, $(R^2)_n$ is 4-CF$_3$ |
| 830 | A is A-2b, $(R^2)_n$ is 4-CN |
| 831 | A is A-2b, $(R^2)_n$ is 4-OMe |
| 832 | A is A-2b, $(R^2)_n$ is 4,6-di-F |
| 833 | A is A-2b, $(R^2)_n$ is 4,6-di-Cl |
| 834 | A is A-2b, $(R^2)_n$ is 4,6-di-Me |
| 835 | A is A-2b, $(R^2)_n$ is 4-Cl-6-F |
| 836 | A is A-2b, $(R^2)_n$ is 4-Cl-6-Me |
| 837 | A is A-2b, $(R^2)_n$ is 4-F-6-Me |
| 838 | A is A-2c, $(R^2)_n$ is H (n is 0) |
| 839 | A is A-2c, $(R^2)_n$ is 4-F |
| 840 | A is A-2c, $(R^2)_n$ is 4-Cl |
| 841 | A is A-2c, $(R^2)_n$ is 4-Br |
| 842 | A is A-2c, $(R^2)_n$ is 4-I |
| 843 | A is A-2c, $(R^2)_n$ is 4-Me |
| 844 | A is A-2c, $(R^2)_n$ is 4-Et |
| 845 | A is A-2c, $(R^2)_n$ is 4-CF$_3$ |
| 846 | A is A-2c, $(R^2)_n$ is 4-CN |
| 847 | A is A-2c, $(R^2)_n$ is 4-OMe |
| 848 | A is A-2c, $(R^2)_n$ is 4,6-di-F |
| 849 | A is A-2c, $(R^2)_n$ is 4,6-di-Cl |
| 850 | A is A-2c, $(R^2)_n$ is 4,6-di-Me |
| 851 | A is A-2c, $(R^2)_n$ is 4-Cl-6-F |
| 852 | A is A-2c, $(R^2)_n$ is 4-Cl-6-Me |
| 853 | A is A-2c, $(R^2)_n$ is 4-F-6-Me |
| 854 | A is A-2d, $(R^2)_n$ is H (n is 0) |
| 855 | A is A-2d, $(R^2)_n$ is 4-F |
| 856 | A is A-2d, $(R^2)_n$ is 4-Cl |
| 857 | A is A-2d, $(R^2)_n$ is 4-Br |
| 858 | A is A-2d, $(R^2)_n$ is 4-I |
| 859 | A is A-2d, $(R^2)_n$ is 4-Me |
| 860 | A is A-2d, $(R^2)_n$ is 4-Et |
| 861 | A is A-2d, $(R^2)_n$ is 4-CF$_3$ |
| 862 | A is A-2d, $(R^2)_n$ is 4-CN |
| 863 | A is A-2d, $(R^2)_n$ is 4-OMe |
| 864 | A is A-2d, $(R^2)_n$ is 4,6-di-F |
| 865 | A is A-2d, $(R^2)_n$ is 4,6-di-Cl |
| 866 | A is A-2d, $(R^2)_n$ is 4,6-di-Me |

| Table | Row Heading |
|---|---|
| 867 | A is A-2d, $(R^2)_n$ is 4-Cl-6-F |
| 868 | A is A-2d, $(R^2)_n$ is 4-Cl-6-Me |
| 869 | A is A-2d, $(R^2)_n$ is 4-F-6-Me |
| 870 | A is A-3b, $(R^2)_n$ is H (n is 0) |
| 871 | A is A-3b, $(R^2)_n$ is 4-F |
| 872 | A is A-3b, $(R^2)_n$ is 4-Cl |
| 873 | A is A-3b, $(R^2)_n$ is 4-Br |
| 874 | A is A-3b, $(R^2)_n$ is 4-I |
| 875 | A is A-3b, $(R^2)_n$ is 4-Me |
| 876 | A is A-3b, $(R^2)_n$ is 4-Et |
| 877 | A is A-3b, $(R^2)_n$ is 4-CF$_3$ |
| 878 | A is A-3b, $(R^2)_n$ is 4-CN |
| 879 | A is A-3b, $(R^2)_n$ is 4-OMe |
| 880 | A is A-3b, $(R^2)_n$ is 4,6-di-F |
| 881 | A is A-3b, $(R^2)_n$ is 4,6-di-Cl |
| 882 | A is A-3b, $(R^2)_n$ is 4,6-di-Me |
| 883 | A is A-3b, $(R^2)_n$ is 4-Cl-6-F |
| 884 | A is A-3b, $(R^2)_n$ is 4-Cl-6-Me |
| 885 | A is A-3b, $(R^2)_n$ is 4-F-6-Me |
| 886 | A is A-3c, $(R^2)_n$ is H (n is 0) |
| 887 | A is A-3c, $(R^2)_n$ is 4-F |
| 888 | A is A-3c, $(R^2)_n$ is 4-Cl |
| 889 | A is A-3c, $(R^2)_n$ is 4-Br |
| 890 | A is A-3c, $(R^2)_n$ is 4-I |
| 891 | A is A-3c, $(R^2)_n$ is 4-Me |
| 892 | A is A-3c, $(R^2)_n$ is 4-Et |
| 893 | A is A-3c, $(R^2)_n$ is 4-CF$_3$ |
| 894 | A is A-3c, $(R^2)_n$ is 4-CN |
| 895 | A is A-3c, $(R^2)_n$ is 4-OMe |
| 896 | A is A-3c, $(R^2)_n$ is 4,6-di-F |
| 897 | A is A-3c, $(R^2)_n$ is 4,6-di-Cl |
| 898 | A is A-3c, $(R^2)_n$ is 4,6-di-Me |
| 899 | A is A-3c, $(R^2)_n$ is 4-Cl-6-F |
| 900 | A is A-3c, $(R^2)_n$ is 4-Cl-6-Me |
| 901 | A is A-3c, $(R^2)_n$ is 4-F-6-Me |
| 902 | A is A-4a, $(R^2)_n$ is H (n is 0) |
| 903 | A is A-4a, $(R^2)_n$ is 4-F |
| 904 | A is A-4a, $(R^2)_n$ is 4-Cl |
| 905 | A is A-4a, $(R^2)_n$ is 4-Br |
| 906 | A is A-4a, $(R^2)_n$ is 4-I |
| 907 | A is A-4a, $(R^2)_n$ is 4-Me |
| 908 | A is A-4a, $(R^2)_n$ is 4-Et |
| 909 | A is A-4a, $(R^2)_n$ is 4-CF$_3$ |
| 910 | A is A-4a, $(R^2)_n$ is 4-CN |
| 911 | A is A-4a, $(R^2)_n$ is 4-OMe |
| 912 | A is A-4a, $(R^2)_n$ is 4,6-di-F |
| 913 | A is A-4a, $(R^2)_n$ is 4,6-di-Cl |
| 914 | A is A-4a, $(R^2)_n$ is 4,6-di-Me |
| 915 | A is A-4a, $(R^2)_n$ is 4-Cl-6-F |
| 916 | A is A-4a, $(R^2)_n$ is 4-Cl-6-Me |
| 917 | A is A-4a, $(R^2)_n$ is 4-F-6-Me |
| 918 | A is A-6c, $(R^2)_n$ is H (n is 0) |
| 919 | A is A-6c, $(R^2)_n$ is 4-F |
| 920 | A is A-6c, $(R^2)_n$ is 4-Cl |
| 921 | A is A-6c, $(R^2)_n$ is 4-Br |
| 922 | A is A-6c, $(R^2)_n$ is 4-I |
| 923 | A is A-6c, $(R^2)_n$ is 4-Me |
| 924 | A is A-6c, $(R^2)_n$ is 4-Et |
| 925 | A is A-6c, $(R^2)_n$ is 4-CF$_3$ |
| 926 | A is A-6c, $(R^2)_n$ is 4-CN |
| 927 | A is A-6c, $(R^2)_n$ is 4-OMe |
| 928 | A is A-6c, $(R^2)_n$ is 4,6-di-F |
| 929 | A is A-6c, $(R^2)_n$ is 4,6-di-Cl |
| 930 | A is A-6c, $(R^2)_n$ is 4,6-di-Me |
| 931 | A is A-6c, $(R^2)_n$ is 4-Cl-6-F |
| 932 | A is A-6c, $(R^2)_n$ is 4-Cl-6-Me |
| 933 | A is A-6c, $(R^2)_n$ is 4-F-6-Me |
| 934 | A is A-7a, $(R^2)_n$ is H (n is 0) |
| 935 | A is A-7a, $(R^2)_n$ is 4-F |
| 936 | A is A-7a, $(R^2)_n$ is 4-Cl |
| 937 | A is A-7a, $(R^2)_n$ is 4-Br |
| 938 | A is A-7a, $(R^2)_n$ is 4-I |
| 939 | A is A-7a, $(R^2)_n$ is 4-Me |
| 940 | A is A-7a, $(R^2)_n$ is 4-Et |
| 941 | A is A-7a, $(R^2)_n$ is 4-CF$_3$ |
| 942 | A is A-7a, $(R^2)_n$ is 4-CN |
| 943 | A is A-7a, $(R^2)_n$ is 4-OMe |
| 944 | A is A-7a, $(R^2)_n$ is 4,6-di-F |
| 945 | A is A-7a, $(R^2)_n$ is 4,6-di-Cl |
| 946 | A is A-7a, $(R^2)_n$ is 4,6-di-Me |
| 947 | A is A-7a, $(R^2)_n$ is 4-Cl-6-F |
| 948 | A is A-7a, $(R^2)_n$ is 4-Cl-6-Me |
| 949 | A is A-7a, $(R^2)_n$ is 4-F-6-Me |
| 950 | A is A-8a, $(R^2)_n$ is H (n is 0) |
| 951 | A is A-8a, $(R^2)_n$ is 4-F |
| 952 | A is A-8a, $(R^2)_n$ is 4-Cl |
| 953 | A is A-8a, $(R^2)_n$ is 4-Br |
| 954 | A is A-8a, $(R^2)_n$ is 4-I |
| 955 | A is A-8a, $(R^2)_n$ is 4-Me |
| 956 | A is A-8a, $(R^2)_n$ is 4-Et |
| 957 | A is A-8a, $(R^2)_n$ is 4-CF$_3$ |
| 958 | A is A-8a, $(R^2)_n$ is 4-CN |
| 959 | A is A-8a, $(R^2)_n$ is 4-OMe |
| 960 | A is A-8a, $(R^2)_n$ is 4,6-di-F |
| 961 | A is A-8a, $(R^2)_n$ is 4,6-di-Cl |
| 962 | A is A-8a, $(R^2)_n$ is 4,6-di-Me |
| 963 | A is A-8a, $(R^2)_n$ is 4-Cl-6-F |
| 964 | A is A-8a, $(R^2)_n$ is 4-Cl-6-Me |
| 965 | A is A-8a, $(R^2)_n$ is 4-F-6-Me |

TABLE 966

Table 966 is constructed as Table 1 except the chemical structure is replaced with the following structure: wherein A is A-1a; n is 0; and each Q is selected from the values listed in Exhibit B. Therefore, the first entry in Table 968 is a compound of Formula 1 wherein Z is O; $R^1$ is H; L is 1,2-phenylene; G is G-4; A is A-1a; n is 0; and Q is 3-CF$_3$-pyrazol-1-yl. The second entry in Table 966 is a compound of Formula 1 wherein Z is O; $R^1$ is H; L is 1,2-phenylene; G is G-4; A is A-1a; n is 0; and Q is 4-CF$_3$-1H-pyrazol-1-yl. The remaining entries in Table 966 are constructed in the same manner.

Tables 967 through 1221 are constructed similarly.

| Table | Row heading |
|---|---|
| 967 | A is A-1a, $(R^2)_n$ is 4-F |
| 968 | A is A-1a, $(R^2)_n$ is 4-Cl |
| 969 | A is A-1a, $(R^2)_n$ is 4-Br |
| 970 | A is A-1a, $(R^2)_n$ is 4-I |
| 971 | A is A-1a, $(R^2)_n$ is 4-Me |
| 972 | A is A-1a, $(R^2)_n$ is 4-Et |
| 973 | A is A-1a, $(R^2)_n$ is 4-CF$_3$ |
| 974 | A is A-1a, $(R^2)_n$ is 4-CN |
| 975 | A is A-1a, $(R^2)_n$ is 4-OMe |
| 976 | A is A-1a, $(R^2)_n$ is 4,6-di-F |
| 977 | A is A-1a, $(R^2)_n$ is 4,6-di-Cl |
| 978 | A is A-1a, $(R_2)_n$ is 4,6-di-Me |
| 979 | A is A-1a, $(R^2)_n$ is 4-Cl-6-F |
| 980 | A is A-1a, $(R^2)_n$ is 4-Cl-6-Me |
| 981 | A is A-1a, $(R^2)_n$ is 4-F-6-Me |
| 982 | A is A-1d, $(R^2)_n$ is H (n is 0) |

-continued

| Table | Row heading |
|---|---|
| 983 | A is A-1d, $(R^2)_n$ is 4-F |
| 984 | A is A-1d, $(R^2)_n$ is 4-Cl |
| 985 | A is A-1d, $(R^2)_n$ is 4-Br |
| 986 | A is A-1d, $(R^2)_n$ is 4-I |
| 987 | A is A-1d, $(R^2)_n$ is 4-Me |
| 988 | A is A-1d, $(R^2)_n$ is 4-Et |
| 989 | A is A-1d, $(R^2)_n$ is 4-CF$_3$ |
| 990 | A is A-1d, $(R^2)_n$ is 4-CN |
| 991 | A is A-1d, $(R^2)_n$ is 4-OMe |
| 992 | A is A-1d, $(R^2)_n$ is 4,6-di-F |
| 993 | A is A-1d, $(R^2)_n$ is 4,6-di-Cl |
| 994 | A is A-1d, $(R^2)_n$ is 4,6-di-Me |
| 995 | A is A-1d, $(R^2)_n$ is 4-Cl-6-F |
| 996 | A is A-1d, $(R^2)_n$ is 4-Cl-6-Me |
| 997 | A is A-1d, $(R^2)_n$ is 4-F-6-Me |
| 998 | A is A-1f, $(R^2)_n$ is H (n is 0) |
| 999 | A is A-1f, $(R^2)_n$ is 4-F |
| 1000 | A is A-1f, $(R^2)_n$ is 4-Cl |
| 1001 | A is A-1f, $(R^2)_n$ is 4-Br |
| 1002 | A is A-1f, $(R^2)_n$ is 4-I |
| 1003 | A is A-1f, $(R^2)_n$ is 4-Me |
| 1004 | A is A-1f, $(R^2)_n$ is 4-Et |
| 1005 | A is A-1f, $(R^2)_n$ is 4-CF$_3$ |
| 1006 | A is A-1f, $(R^2)_n$ is 4-CN |
| 1007 | A is A-1f, $(R^2)_n$ is 4-OMe |
| 1008 | A is A-1f, $(R^2)_n$ is 4,6-di-F |
| 1009 | A is A-1f, $(R^2)_n$ is 4,6-di-Cl |
| 1010 | A is A-1f, $(R^2)_n$ is 4,6-di-Me |
| 1011 | A is A-1f, $(R^2)_n$ is 4-Cl-6-F |
| 1012 | A is A-1f, $(R^2)_n$ is 4-Cl-6-Me |
| 1013 | A is A-1f, $(R^2)_n$ is 4-F-6-Me |
| 1014 | A is A-1h, $(R^2)_n$ is H (n is 0) |
| 1015 | A is A-1h, $(R^2)_n$ is 4-F |
| 1016 | A is A-1h, $(R^2)_n$ is 4-Cl |
| 1017 | A is A-1h, $(R^2)_n$ is 4-Br |
| 1018 | A is A-1h, $(R^2)_n$ is 4-I |
| 1019 | A is A-1h, $(R^2)_n$ is 4-Me |
| 1020 | A is A-1h, $(R^2)_n$ is 4-Et |
| 1021 | A is A-1h, $(R^2)_n$ is 4-CF$_3$ |
| 1022 | A is A-1h, $(R^2)_n$ is 4-CN |
| 1023 | A is A-1h, $(R^2)_n$ is 4-OMe |
| 1024 | A is A-1h, $(R^2)_n$ is 4,6-di-F |
| 1025 | A is A-1h, $(R^2)_n$ is 4,6-di-Cl |
| 1026 | A is A-1h, $(R^2)_n$ is 4,6-di-Me |
| 1027 | A is A-1h, $(R^2)_n$ is 4-Cl-6-F |
| 1028 | A is A-1h, $(R^2)_n$ is 4-Cl-6-Me |
| 1029 | A is A-1h, $(R^2)_n$ is 4-F-6-Me |
| 1030 | A is A-1k, $(R^2)_n$ is H (n is 0) |
| 1031 | A is A-1k, $(R^2)_n$ is 4-F |
| 1032 | A is A-1k, $(R^2)_n$ is 4-Cl |
| 1033 | A is A-1k, $(R^2)_n$ is 4-Br |
| 1034 | A is A-1k, $(R^2)_n$ is 4-I |
| 1035 | A is A-1k, $(R^2)_n$ is 4-Me |
| 1036 | A is A-1k, $(R^2)_n$ is 4-Et |
| 1037 | A is A-1k, $(R^2)_n$ is 4-CF$_3$ |
| 1038 | A is A-1k, $(R^2)_n$ is 4-CN |
| 1039 | A is A-1k, $(R^2)_n$ is 4-OMe |
| 1040 | A is A-1k, $(R^2)_n$ is 4,6-di-F |
| 1041 | A is A-1k, $(R^2)_n$ is 4,6-di-Cl |
| 1042 | A is A-1k, $(R^2)_n$ is 4,6-di-Me |
| 1043 | A is A-1k, $(R^2)_n$ is 4-Cl-6-F |
| 1044 | A is A-1k, $(R^2)_n$ is 4-Cl-6-Me |
| 1045 | A is A-1k, $(R^2)_n$ is 4-F-6-Me |
| 1046 | A is A-1l, $(R^2)_n$ is H (n is 0) |
| 1047 | A is A-1l, $(R^2)_n$ is 4-F |
| 1048 | A is A-1l, $(R^2)_n$ is 4-Cl |
| 1049 | A is A-1l, $(R^2)_n$ is 4-Br |
| 1050 | A is A-1l, $(R^2)_n$ is 4-I |
| 1051 | A is A-1l, $(R^2)_n$ is 4-Me |
| 1052 | A is A-1l, $(R^2)_n$ is 4-Et |
| 1053 | A is A-1l, $(R^2)_n$ is 4-CF$_3$ |
| 1054 | A is A-1l, $(R^2)_n$ is 4-CN |
| 1055 | A is A-1l, $(R^2)_n$ is 4-OMe |
| 1056 | A is A-1l, $(R^2)_n$ is 4,6-di-F |
| 1057 | A is A-1l, $(R^2)_n$ is 4,6-di-Cl |
| 1058 | A is A-1l, $(R^2)_n$ is 4,6-di-Me |
| 1059 | A is A-1l, $(R^2)_n$ is 4-Cl-6-F |
| 1060 | A is A-1l, $(R^2)_n$ is 4-Cl-6-Me |
| 1061 | A is A-1l, $(R^2)_n$ is 4-F-6-Me |
| 1062 | A is A-2a, $(R^2)_n$ is H (n is 0) |
| 1063 | A is A-2a, $(R^2)_n$ is 4-F |
| 1064 | A is A-2a, $(R^2)_n$ is 4-Cl |
| 1065 | A is A-2a, $(R^2)_n$ is 4-Br |
| 1066 | A is A-2a, $(R^2)_n$ is 4-I |
| 1067 | A is A-2a, $(R^2)_n$ is 4-Me |
| 1068 | A is A-2a, $(R^2)_n$ is 4-Et |
| 1069 | A is A-2a, $(R^2)_n$ is 4-CF$_3$ |
| 1070 | A is A-2a, $(R^2)_n$ is 4-CN |
| 1071 | A is A-2a, $(R^2)_n$ is 4-OMe |
| 1072 | A is A-2a, $(R^2)_n$ is 4,6-di-F |
| 1073 | A is A-2a, $(R^2)_n$ is 4,6-di-Cl |
| 1074 | A is A-2a, $(R^2)_n$ is 4,6-di-Me |
| 1075 | A is A-2a, $(R^2)_n$ is 4-Cl-6-F |
| 1076 | A is A-2a, $(R^2)_n$ is 4-Cl-6-Me |
| 1077 | A is A-2a, $(R^2)_n$ is 4-F-6-Me |
| 1078 | A is A-2b, $(R^2)_n$ is H (n is 0) |
| 1079 | A is A-2b, $(R^2)_n$ is 4-F |
| 1080 | A is A-2b, $(R^2)_n$ is 4-Cl |
| 1081 | A is A-2b, $(R^2)_n$ is 4-Br |
| 1082 | A is A-2b, $(R^2)_n$ is 4-I |
| 1083 | A is A-2b, $(R^2)_n$ is 4-Me |
| 1084 | A is A-2b, $(R^2)_n$ is 4-Et |
| 1085 | A is A-2b, $(R^2)_n$ is 4-CF$_3$ |
| 1086 | A is A-2b, $(R^2)_n$ is 4-CN |
| 1087 | A is A-2b, $(R^2)_n$ is 4-OMe |
| 1088 | A is A-2b, $(R^2)_n$ is 4,6-di-F |
| 1089 | A is A-2b, $(R^2)_n$ is 4,6-di-Cl |
| 1090 | A is A-2b, $(R^2)_n$ is 4,6-di-Me |
| 1091 | A is A-2b, $(R^2)_n$ is 4-Cl-6-F |
| 1092 | A is A-2b, $(R^2)_n$ is 4-Cl-6-Me |
| 1093 | A is A-2b, $(R^2)_n$ is 4-F-6-Me |
| 1094 | A is A-2c, $(R^2)_n$ is H (n is 0) |
| 1095 | A is A-2c, $(R^2)_n$ is 4-F |
| 1096 | A is A-2c, $(R^2)_n$ is 4-Cl |
| 1097 | A is A-2c, $(R^2)_n$ is 4-Br |
| 1098 | A is A-2c, $(R^2)_n$ is 4-I |
| 1099 | A is A-2c, $(R^2)_n$ is 4-Me |
| 1100 | A is A-2c, $(R^2)_n$ is 4-Et |
| 1101 | A is A-2c, $(R^2)_n$ is 4-CF$_3$ |
| 1102 | A is A-2c, $(R^2)_n$ is 4-CN |
| 1103 | A is A-2c, $(R^2)_n$ is 4-OMe |
| 1104 | A is A-2c, $(R^2)_n$ is 4,6-di-F |
| 1105 | A is A-2c, $(R^2)_n$ is 4,6-di-Cl |
| 1106 | A is A-2c, $(R^2)_n$ is 4,6-di-Me |
| 1107 | A is A-2c, $(R^2)_n$ is 4-Cl-6-F |
| 1108 | A is A-2c, $(R^2)_n$ is 4-Cl-6-Me |
| 1109 | A is A-2c, $(R^2)_n$ is 4-F-6-Me |
| 1110 | A is A-2d, $(R^2)_n$ is H (n is 0) |
| 1111 | A is A-2d, $(R^2)_n$ is 4-F |
| 1112 | A is A-2d, $(R^2)_n$ is 4-Cl |
| 1113 | A is A-2d, $(R^2)_n$ is 4-Br |
| 1114 | A is A-2d, $(R^2)_n$ is 4-I |
| 1115 | A is A-2d, $(R^2)_n$ is 4-Me |
| 1116 | A is A-2d, $(R^2)_n$ is 4-Et |
| 1117 | A is A-2d, $(R^2)_n$ is 4-CF$_3$ |
| 1118 | A is A-2d, $(R^2)_n$ is 4-CN |
| 1119 | A is A-2d, $(R^2)_n$ is 4-OMe |
| 1120 | A is A-2d, $(R^2)_n$ is 4,6-di-F |
| 1121 | A is A-2d, $(R^2)_n$ is 4,6-di-Cl |
| 1122 | A is A-2d, $(R^2)_n$ is 4,6-di-Me |
| 1123 | A is A-2d, $(R^2)_n$ is 4-Cl-6-F |
| 1124 | A is A-2d, $(R^2)_n$ is 4-Cl-6-Me |
| 1125 | A is A-2d, $(R^2)_n$ is 4-F-6-Me |
| 1126 | A is A-3b, $(R^2)_n$ is H (n is 0) |
| 1127 | A is A-3b, $(R^2)_n$ is 4-F |
| 1128 | A is A-3b, $(R^2)_n$ is 4-Cl |
| 1129 | A is A-3b, $(R^2)_n$ is 4-Br |
| 1130 | A is A-3b, $(R^2)_n$ is 4-I |
| 1131 | A is A-3b, $(R^2)_n$ is 4-Me |
| 1132 | A is A-3b, $(R^2)_n$ is 4-Et |
| 1133 | A is A-3b, $(R^2)_n$ is 4-CF$_3$ |
| 1134 | A is A-3b, $(R^2)_n$ is 4-CN |
| 1135 | A is A-3b, $(R^2)_n$ is 4-OMe |
| 1136 | A is A-3b, $(R^2)_n$ is 4,6-di-F |

| Table | Row heading |
|---|---|
| 1137 | A is A-3b, $(R^2)_n$ is 4,6-di-Cl |
| 1138 | A is A-3b, $(R^2)_n$ is 4,6-di-Me |
| 1139 | A is A-3b, $(R^2)_n$ is 4-Cl-6-F |
| 1140 | A is A-3b, $(R^2)_n$ is 4-Cl-6-Me |
| 1141 | A is A-3b, $(R^2)_n$ is 4-F-6-Me |
| 1142 | A is A-3c, $(R^2)_n$ is H (n is 0) |
| 1143 | A is A-3c, $(R^2)_n$ is 4-F |
| 1144 | A is A-3c, $(R^2)_n$ is 4-Cl |
| 1145 | A is A-3c, $(R^2)_n$ is 4-Br |
| 1146 | A is A-3c, $(R^2)_n$ is 4-I |
| 1147 | A is A-3c, $(R^2)_n$ is 4-Me |
| 1148 | A is A-3c, $(R^2)_n$ is 4-Et |
| 1149 | A is A-3c, $(R^2)_n$ is 4-$CF_3$ |
| 1150 | A is A-3c, $(R^2)_n$ is 4-CN |
| 1151 | A is A-3c, $(R^2)_n$ is 4-OMe |
| 1152 | A is A-3c, $(R^2)_n$ is 4,6-di-F |
| 1153 | A is A-3c, $(R^2)_n$ is 4,6-di-Cl |
| 1154 | A is A-3c, $(R^2)_n$ is 4,6-di-Me |
| 1155 | A is A-3c, $(R^2)_n$ is 4-Cl-6-F |
| 1156 | A is A-3c, $(R^2)_n$ is 4-Cl-6-Me |
| 1157 | A is A-3c, $(R^2)_n$ is 4-F-6-Me |
| 1158 | A is A-4a, $(R^2)_n$ is H (n is 0) |
| 1159 | A is A-4a, $(R^2)_n$ is 4-F |
| 1160 | A is A-4a, $(R^2)_n$ is 4-Cl |
| 1161 | A is A-4a, $(R^2)_n$ is 4-Br |
| 1162 | A is A-4a, $(R^2)_n$ is 4-I |
| 1163 | A is A-4a, $(R^2)_n$ is 4-Me |
| 1164 | A is A-4a, $(R^2)_n$ is 4-Et |
| 1165 | A is A-4a, $(R^2)_n$ is 4-$CF_3$ |
| 1166 | A is A-4a, $(R^2)_n$ is 4-CN |
| 1167 | A is A-4a, $(R^2)_n$ is 4-OMe |
| 1168 | A is A-4a, $(R^2)_n$ is 4,6-di-F |
| 1169 | A is A-4a, $(R^2)_n$ is 4,6-di-Cl |
| 1170 | A is A-4a, $(R^2)_n$ is 4,6-di-Me |
| 1171 | A is A-4a, $(R^2)_n$ is 4-Cl-6-F |
| 1172 | A is A-4a, $(R^2)_n$ is 4-Cl-6-Me |
| 1173 | A is A-4a, $(R^2)_n$ is 4-F-6-Me |
| 1174 | A is A-6c, $(R^2)_n$ is H, n is 0 |
| 1175 | A is A-6c, $(R^2)_n$ is 4-F |
| 1176 | A is A-6c, $(R^2)_n$ is 4-Cl |
| 1177 | A is A-6c, $(R^2)_n$ is 4-Br |
| 1178 | A is A-6c, $(R^2)_n$ is 4-I |
| 1179 | A is A-6c, $(R^2)_n$ is 4-Me |
| 1180 | A is A-6c, $(R^2)_n$ is 4-Et |
| 1181 | A is A-6c, $(R^2)_n$ is 4-$CF_3$ |
| 1182 | A is A-6c, $(R^2)_n$ is 4-CN |
| 1183 | A is A-6c, $(R^2)_n$ is 4-OMe |
| 1184 | A is A-6c, $(R^2)_n$ is 4,6-di-F |
| 1185 | A is A-6c, $(R^2)_n$ is 4,6-di-Cl |
| 1186 | A is A-6c, $(R^2)_n$ is 4,6-di-Me |
| 1187 | A is A-6c, $(R^2)_n$ is 4-Cl-6-F |
| 1188 | A is A-6c, $(R^2)_n$ is 4-Cl-6-Me |
| 1189 | A is A-6c, $(R^2)_n$ is 4-F-6-Me |
| 1190 | A is A-7a, $(R^2)_n$ is H (n is 0) |
| 1191 | A is A-7a, $(R^2)_n$ is 4-F |
| 1192 | A is A-7a, $(R^2)_n$ is 4-Cl |
| 1193 | A is A-7a, $(R^2)_n$ is 4-Br |
| 1194 | A is A-7a, $(R^2)_n$ is 4-I |
| 1195 | A is A-7a, $(R^2)_n$ is 4-Me |
| 1196 | A is A-7a, $(R^2)_n$ is 4-Et |
| 1197 | A is A-7a, $(R^2)_n$ is 4-$CF_3$ |
| 1198 | A is A-7a, $(R^2)_n$ is 4-CN |
| 1199 | A is A-7a, $(R^2)_n$ is 4-OMe |
| 1200 | A is A-7a, $(R^2)_n$ is 4,6-di-F |
| 1201 | A is A-7a, $(R^2)_n$ is 4,6-di-Cl |
| 1202 | A is A-7a, $(R^2)_n$ is 4,6-di-Me |
| 1203 | A is A-7a, $(R^2)_n$ is 4-Cl-6-F |
| 1204 | A is A-7a, $(R^2)_n$ is 4-Cl-6-Me |
| 1205 | A is A-7a, $(R^2)_n$ is 4-F-6-Me |
| 1206 | A is A-8a, $(R^2)_n$ is H (n is 0) |
| 1207 | A is A-8a, $(R^2)_n$ is 4-F |
| 1208 | A is A-8a, $(R^2)_n$ is 4-Cl |
| 1209 | A is A-8a, $(R^2)_n$ is 4-Br |
| 1210 | A is A-8a, $(R^2)_n$ is 4-I |
| 1211 | A is A-8a, $(R^2)_n$ is 4-Me |
| 1212 | A is A-8a, $(R^2)_n$ is 4-Et |
| 1213 | A is A-8a, $(R^2)_n$ is 4-$CF_3$ |
| 1214 | A is A-8a, $(R^2)_n$ is 4-CN |
| 1215 | A is A-8a, $(R^2)_n$ is 4-OMe |
| 1216 | A is A-8a, $(R^2)_n$ is 4,6-di-F |
| 1217 | A is A-8a, $(R^2)_n$ is 4,6-di-Cl |
| 1218 | A is A-8a, $(R^2)_n$ is 4,6-di-Me |
| 1219 | A is A-8a, $(R^2)_n$ is 4-Cl-6-F |
| 1220 | A is A-8a, $(R^2)_n$ is 4-Cl-6-Me |
| 1221 | A is A-8a, $(R^2)_n$ is 4-F-6-Me |

Formulation/Utility

A compound of Formula 1 of this invention (including N-oxides and salts thereof) will generally be used as a fungicidal active ingredient in a composition, i.e. formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

One embodiment of the present invention relates to a method for controlling fungal pathogens, comprising diluting the fungicidal composition of the present invention (a compound of Formula 1 formulated with surfactants, solid diluents and liquid diluents or a formulated mixture of a compound of Formula 1 and at least one other fungicide) with water, and optionally adding an adjuvant to form a diluted composition, and contacting the fungal pathogen or its environment with an effective amount of said diluted composition.

Although a spray composition formed by diluting with water a sufficient concentration of the present fungicidal composition can provide sufficient efficacy for controlling fungal pathogens, separately formulated adjuvant products can also be added to spray tank mixtures. These additional adjuvants are commonly known as "spray adjuvants" or "tank-mix adjuvants", and include any substance mixed in a spray tank to improve the performance of a pesticide or alter the physical properties of the spray mixture. Adjuvants can be anionic or nonionic surfactants, emulsifying agents, petroleum-based crop oils, crop-derived seed oils, acidifiers, buffers, thickeners or defoaming agents. Adjuvants are used to enhancing efficacy (e.g., biological availability, adhesion, penetration, uniformity of coverage and durability of protection), or minimizing or eliminating spray application problems associated with incompatibility, foaming, drift, evaporation, volatilization and degradation. To obtain optimal performance, adjuvants are selected with regard to the properties of the active ingredient, formulation and target (e.g., crops, insect pests).

The amount of adjuvants added to spray mixtures is generally in the range of about 2.5% to 0.1% by volume. The application rates of adjuvants added to spray mixtures are typically between about 1 to 5 L per hectare. Representative examples of spray adjuvants include: Adigor® (Syngenta) 47% methylated rapeseed oil in liquid hydrocarbons, Silwet® (Helena Chemical Company) polyalkyleneoxide modified heptamethyltrisiloxane and Assist® (BASF) 17% surfactant blend in 83% paraffin based mineral oil.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1 and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects*, 1994 BCPC Monograph No. 57, and references listed therein.

For further information regarding the art of formulation, see T. S. Woods, "The Formulator's Toolbox—Product Forms for Modern Agriculture" in *Pesticide Chemistry and Bioscience, The Food—Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A B, and C. Without further elaboration, it is believed that one skilled in the art using the preceding description can utilize the present invention to its fullest extent. The following Examples are, therefore, to be constructed as merely illustrative, and not limiting of the disclosure in any way whatsoever. Percentages are by weight except where otherwise indicated.

Example A

| High Strength Concentrate | |
| --- | --- |
| Compound 68 | 98.5% |
| silica aerogel | 0.5% |
| synthetic amorphous fine silica | 1.0% |

Example B

| Wettable Powder | |
| --- | --- |
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
| --- | --- |
| Compound 54 | 10.0% |
| attapulgite granules (low volatile matter, 0.71/0.30 mm; U.S.S. No. 25-50 sieves) | 90.0% |

Example D

| Extruded Pellet | |
| --- | --- |
| Compound 58 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
| --- | --- |
| Compound 83 | 10.0% |
| polyoxyethylene sorbitol hexoleate | 20.0% |
| $C_6$-$C_{10}$ fatty acid methyl ester | 70.0% |

Example F

| Microemulsion | |
| --- | --- |
| Compound 34 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
| --- | --- |
| Compound 50 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

| Fertilizer Stick | |
| --- | --- |
| compound 84 | 2.50% |
| pyrrolidone-styrene copolymer | 4.80% |
| tristyrylphenyl 16-ethoxylate | 2.30% |
| talc | 0.80% |
| corn starch | 5.00% |
| slow-release fertilizer | 36.00% |
| kaolin | 38.00% |
| water | 10.60% |

Example I

| Suspension Concentrate | |
| --- | --- |
| Compound 68 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

| Emulsion in Water | |
| --- | --- |
| compound 2 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |

-continued

| Emulsion in Water | |
|---|---|
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example K

| Oil Dispersion | |
|---|---|
| compound 34 | 25% |
| polyoxyethylene sorbitol hexaoleate | 15% |
| organically modified bentonite clay | 2.5% |
| fatty acid methyl ester | 57.5% |

Example L

| Suspoemulsion | |
|---|---|
| compound 50 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Water-soluble and water-dispersible formulations are typically diluted with water to form aqueous compositions before application. Aqueous compositions for direct applications to the plant or portion thereof (e.g., spray tank compositions) typically contain at least about 1 ppm or more (e.g., from 1 ppm to 100 ppm) of the compound(s) of this invention.

Seed is normally treated at a rate of from about 0.001 g (more typically about 0.1 g) to about 10 g per kilogram of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Ascomycota, Basidiomycota, Zygomycota phyla, and the fungal-like Oomycata class. They are effective in controlling a broad spectrum of plant diseases, particularly foliar pathogens of ornamental, turf, vegetable, field, cereal, and fruit crops. These pathogens include but are not limited to those listed in Table I. For Ascomycetes and Basidiomycetes, names for both the sexual/teleomorph/perfect stage as well as names for the asexual/anamorph/imperfect stage (in parentheses) are listed where known. Synonymous names for pathogens are indicated by an equal sign. For example, the sexual/teleomorph/perfect stage name *Phaeosphaeria nodorum* is followed by the corresponding asexual/anamorph/imperfect stage name *Stagnospora nodorum* and the synonymous older name *Septoria nodorum*.

TABLE I

Ascomycetes in the order Pleosporales including *Alternaria solani*, *A. alternata* and *A. brassicae*, *Guignardia bidwellii*, *Venturia inaequalis*, *Pyrenophora tritici-repentis* (*Dreschlera tritici-repentis* = *Helminthosporium tritici-repentis*) and *Pyrenophora teres* (*Dreschlera teres* = *Helminthosporium teres*), *Corynespora cassiicola*, *Phaeosphaeria nodorum* (*Stagonospora nodorum* = *Septoria nodorum*), *Cochliobolus carbonum* and *C. heterostrophus*, *Leptosphaeria biglobosa* and *L. maculans*;
Ascomycetes in the order Mycosphaerellales including *Mycosphaerella graminicola* (*Zymoseptoria tritici* = *Septoria tritici*), *M. berkelevi* (*Cercosporidium personatum*), *M. arachidis* (*Cercospora arachidicola*), *Passalora sojina* (*Cercospora sojina*), *Cercospora zeae-maydis* and *C. beticola*;
Ascomycetes in the order Erysiphales (the powdery mildews) such as *Blumeria graminis* f. sp. *tritici* and *Blumeria graminis* f. sp. *hordei*, *Erysiphe polygoni*, *E. necator* (=*Uncinula necator*), *Podosphaera fuliginea* (=*Sphaerotheca fuliginea*), and *Podosphaera leucotricha* (=*Sphaerotheca fuliginea*);
Ascomycetes in the order Helotiales such as *Botryotinia fuckeliana* (*Botrytis cinerea*), *Oculimacula yallundae* (=*Tapesia yallundae*; anamorph *Helgardia herpotrichoides* = *Pseudocercosporella herpetrichoides*), *Monilinia fructicola*, *Sclerotinia sclerotiorum*, *Sclerotinia minor*, and *Sclerotinia homoeocarpa*;
Ascomycetes in the order Hypocreales such as *Giberella zeae* (*Fusarium graminearum*), *G. moniliformis* (*Fusarium moniliforme*), *Fusarium solani* and *Verticillium dahliae*;
Ascomycetes in the order Eurotiales such as *Aspergillus flavus* and *A. parasiticus*;
Ascomycetes in the order Diaporthales such as *Cryptosphorella viticola* (=*Phomopsis viticola*), *Phomopsis longicolla*, and *Diaporthe phaseolorum*;
Other Ascomycete pathogens including *Magnaporthe grisea*, *Gaeumannomyces graminis*, *Rhynchosporium secalis*, and anthracnose pathogens such as *Glomerella acutata* (*Colletotrichum acutatum*), *G. graminicola* (*C. graminicola*) and *G. lagenaria* (*C. orbiculare*);

TABLE I-continued

Basidiomycetes in the order Urediniales (the rusts) including *Puccinia recondita*, *P. striiformis*, *Puccinia hordei*, *P. graminis* and *P. arachidis*), *Hemileia vastatrix* and *Phakopsora pachyrhizi*;
Basidiomycetes in the order Ceratobasidiales such as *Thanatophorum cucumeris* (*Rhizoctonia solani*) and *Ceratobasidium oryzae-sativae* (*Rhizoctonia oryzae*);
Basidiomycetes in the order Polyporales such as *Athelia rolfsii* (*Sclerotium rolfsii*);
Basidiomycetes in the order Ustilaginales such as *Ustilago maydis*;
Zygomycetes in the order Mucorales such as *Rhizopus stolonifer*;
Oomycetes in the order Pythiales, including *Phytophthora infestans*, *P. megasperma*, *P. parasitica*, *P. sojae*, *P. cinnamomi* and *P. capsici*, and *Pythium* pathogens such as *Pythium aphanidermatum*, *P. graminicola*, *P. irregulare*, *P. ultimum* and *P. dissoticum*;
Oomycetes in the order Peronosporales such as *Plasmopara viticola*, *P. halstedii*, *Peronospora hyoscyami* (=*Peronospora tabacina*), *P. manshurica*, *Hyaloperonospora parasitica* (=*Peronospora parasitica*), *Pseudoperonospora cubensis* and *Bremia lactucae*;
and other genera and species closely related to all of the above pathogens.

The compounds of the invention are believed to provide protection from fungal plant pathogens by inhibiting Complex II (succinate dehydrogenase) fungal respiration by disrupting a key enzyme in the Krebs Cycle (TCA cycle) named succinate dehydrogenase (SDH). SDH is composed of four nuclear-encoded polypeptides, identified as SDHA, SDHB, SDHC and SDHD. Inhibiting respiration prevents the fungus from making ATP, and thus inhibits growth and reproduction. At the molecular level, carboxamides inhibit ubiquinone reduction by binding to the ubiquinone binding site ($Q_p$ site) formed by subunits SDHB, SDHC and SDHD in the SDH enzyme. The Fungicide Resistance Action Committee (FRAC) has identified chemical compounds having this fungicidal mode of action as "SDHIs" as an abbreviation for succinate dehydrogenase inhibitors and categorized them with FRAC Code 7.

A variety of mutations in subunits SDHB, SDHC and SDHD forming the ubiquinone binding site are now known to cause resistance to SDHIs. FRAC has published on their website a "List of fungal species with resistance reports towards SDHI fungicides and mutations in the succinate dehydrogenates gene (updated March 2012)" frac.info/frac/work/List%20of%20SDHI%20resistant%20species.pdf available as of 28 Jun. 2012), which includes both mutants produced in the laboratory through artificial mutagenesis and naturally occurring mutants found in the field showing resistance to SDHIs. Scalliet et al., "Mutagenesis and Functional Studies with Succinate Dehydrogenase Inhibitors in the Wheat Pathogen *Mycosphaerella graminicola*", *PLoS ONE*, 2012, 7 (4), 1-20 (published in Adobe Acrobat file format as journal.pone.0035429.pdf and available through www.plosone.org/article/info%3Adoi%2F10.1371%2Fjournal.pone.0035429 on 28 Jun. 2012) describes additional mutants of *Mycosphaerella graminicola*. These publications disclose fungal pathogens having known resistant mutants include *Alternaria alternata* (SDHB: H277Y, H277R; SDHC: H134R; SDHD: D123E, H133R), *Aspergillus oryzae* (SDHB: H249Y, H249L, H249N; SDHC: T901; SDHD: D124E), *Botrytis cinearea* (SDHB: P225L, P225T, P225F, H272Y, H272R, H272L, N230I; SDHD: H132R), *Botrytis elliptica* (SDHB: H272Y, H272R), *Corynespora cassiicola* (SDHB: H287Y, H287R; SDHC: S73P, SDHD: S89P), *Didymella bryoniae* (SDHB: H277R, H277Y), *Mycosphaerella graminicola* (SDHB: S218F, P220T, P220L, S221P, N225H, N225I, R265P, H267L, H267N, H267R, H267Q, H267Y, I269V, N271K; SDHC: T79I, S83G, A84V, A84I, L85P, N86K, R87C, V88D, H145R, H152R; SDHD: D129E, D129G, D129S, D129T, H139E), *Podosphaera xanthii* (SDHB: H[???]Y), *Sclerotinia sclerotiorum* (SDHD: H132R), *Ustilago maydis* (SDHB: H257L), *Stemphylium botryose* (SDHB: P225L, H272Y, H272R) and *Ustilago maydis* (SDHB: H257L), wherein the left letter identifies the amino acid in the prevalent wild-type enzyme subunit, the number specifies the amino acid location in the subunit, and the right letter identifies the amino acid in the mutant subunit (the amino acids are identified by standard single letter codes; see for example www.bio.davidson.edu/Biology/aatable.html, accessed 28 Jun. 2012). Because the metabolism of other fungal pathogens, such as *Septoria tritici*, also involve succinate dehydrogenase, SDHI-resistant mutants are possible for them as well.

Remarkably, compounds of the present invention, retain sufficient activity against mutant fungal pathogens highly resistant to other SDHIs, so that the present compounds remain agronomically useful for protecting plants against the mutant as well as wild-type pathogens. The improved efficacy of the present compounds compared to other SDHI fungicides for controlling plant disease caused by the SDHI-resistant fungal pathogens can be determined by simple plant disease control testing, for example tests similar to Tests A-E disclosed herein, but using SDHI-resistant instead of wild-type fungal pathogens.

In addition to their fungicidal activity, the compositions or combinations also have activity against bacteria such as *Erwinia amylovora*, *Xanthomonas campestris*, *Pseudomonas syringae*, and other related species. By controlling harmful microorganisms, the compounds of the invention are useful for improving (i.e. increasing) the ratio of beneficial to harmful microorganisms in contact with crop plants or their propagules (e.g., seeds, corms, bulbs, tubers, cuttings) or in the agronomic environment of the crop plants or their propagules.

Compounds of the invention are useful in treating all plants, plant parts and seeds. Plant and seed varieties and cultivars can be obtained by conventional propagation and breeding methods or by genetic engineering methods. Genetically modified plants or seeds (transgenic plants or seeds) are those in which a heterologous gene (transgene) has been stably integrated into the plant's or seed's genome. A transgene that is defined by its particular location in the plant genome is called a transformation or transgenic event.

Genetically modified plant cultivars which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Table II. Additional information for the genetic modifications listed in Table 2 can be obtained from publicly available databases maintained, for example, by the U.S. Department of Agriculture.

The following abbreviations, T1 through T37, are used in Table 2 for traits. A "-" means the entry is not available.

| Trait | Description |
|---|---|
| T1 | Glyphosate tolerance |
| T2 | High lauric acid oil |
| T3 | Glufosinate tolerance |
| T4 | Phytate breakdown |
| T5 | Oxynil tolerance |
| T6 | Disease resistance |
| T7 | Insect resistance |
| T9 | Modified flower color |
| T11 | ALS herbicide tol. |
| T12 | Dicamba tolerance |
| T13 | Anti-allergy |
| T14 | Salt tolerance |
| T15 | Cold tolerance |
| T16 | Imidazolinone herbicide tol. |
| T17 | Modified alpha-amylase |
| T18 | Pollination control |
| T19 | 2,4-D tolerance |
| T20 | Increased lysine |
| T21 | Drought tolerance |
| T22 | Delayed ripening/senescence |
| T23 | Modified product quality |
| T24 | High cellulose |
| T25 | Modified starch/carbohydrate |
| T26 | Insect & disease resist. |
| T27 | High tryptophan |
| T28 | Erect leaves semidwarf |
| T29 | Semidwarf |
| T30 | Low iron tolerance |
| T31 | Modified oil/fatty acid |
| T32 | HPPD tolerance |
| T33 | High oil |
| T34 | Aryloxyalkanoate tol. |
| T35 | Mesotrione tolerance |
| T36 | Reduced nicotine |
| T37 | Modified product |

TABLE II

| Crop | Event Name | Event Code | Trait(s) | Gene(s) |
|---|---|---|---|---|
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA5.1 | EMB-PV051-1 | T6 | ac1 (sense and antisense) |
| Brinjal# | EE-1 | — | T7 | cry1Ac |
| Carnation | 11 (7442) | FLO-07442-4 | T8; T9 | surB; dfr; hfl (f3'5'h) |
| Carnation | 11363 (1363A) | FLO-11363-1 | T8; T9 | surB; dfr; bp40 (f3'5'h) |
| Carnation | 1226A (11226) | FLO-11226-8 | T8; T9 | surB; dfr; bp40 (f3'5'h) |
| Carnation | 123.2.2 (40619) | FLO-4Ø619-7 | T8; T9 | surB; dfr; hfl (f3'5'h) |
| Carnation | 123.2.38 (40644) | FLO-4Ø644-4 | T8; T9 | surB; dfr; hfl (f3'5'h) |
| Carnation | 123.8.12 | FLO-4Ø689-6 | T8; T9 | surB; dfr; bp40 (f3'5'h) |
| Carnation | 123.8.8 (40685) | FLO-4Ø685-1 | T8; T9 | surB; dfr; bp40 (f3'5'h) |
| Carnation | 1351A (11351) | FLO-11351-7 | T8; T9 | surB; dfr; bp40 (f3'5'h) |
| Carnation | 1400A (11400) | FLO-114ØØ-2 | T8; T9 | surB; dfr; bp40 (f3'5'h) |
| Carnation | 15 | FLO-ØØØ15-2 | T8; T9 | surB; dfr; hfl (f3'5'h) |
| Carnation | 16 | FLO-ØØØ16-3 | T8; T9 | surB; dfr; hfl (f3'5'h) |
| Carnation | 4 | FLO-ØØØØ4-9 | T8; T9 | surB; dfr; hfl (f3'5'h) |
| Carnation | 66 | FLO-ØØØ66-8 | T8; T10 | surB; acc |
| Carnation | 959A (11959) | FLO-11959-3 | T8; T9 | surB; dfr; bp40 (f3'5'h) |
| Carnation | 988A (11988) | FLO-11988-7 | T8; T9 | surB; dfr; bp40 (f3'5'h) |
| Carnation | 26407 | IFD-26497-2 | ST8; T9 | surB; dfr; bp40 (f3'5'h) |
| Carnation | 25958 | IFD-25958-3 | T8; T9 | surB; dfr; bp40 (f3'5'h) |
| Chicory | RM3-3 | — | T3 | bar |
| Chicory | RM3-4 | — | T3 | bar |

TABLE II-continued

| Crop | Event Name | Event Code | Trait(s) | Gene(s) |
|---|---|---|---|---|
| Chicory | RM3-6 | — | T3 | bar |
| Cotton | 19-51a | DD-Ø1951A-7 | T11 | S4-HrA |
| Cotton | 281-24-236 | DAS-24236-5 | T3; T7 | pat (syn); cry1F |
| Cotton | 3006-210-23 | DAS-21Ø23-5 | T3; T7 | pat (syn); cry1Ac |
| Cotton | 31707 | — | T5; T7 | bxn; cry1Ac |
| Cotton | 31803 | — | T5; T7 | bxn; cry1Ac |
| Cotton | 31807 | — | T5; T7 | bxn; cry1Ac |
| Cotton | 31808 | — | T5; T7 | bxn; cry1Ac |
| Cotton | 42317 | — | T5; T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T7; T3 | cry1Ab; bar |
| Cotton | T304-40 | BCS-GH004-7 | T7; T3 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T12; T3 | Modified dmo; bar |
| Cotton | OsCr11 | — | T13 | Modified Cry j |
| Creeping Bentgrass | ASR368 | SMG-368ØØ-2 | T1 | cp4 epsps (aroA:CP4) |
| Eucalyptus | 20-C | — | T14 | codA |
| Eucalyptus | 12-5C | — | T14 | codA |
| Eucalyptus | 12-5B | — | T14 | codA |
| Eucalyptus | 107-1 | — | T14 | codA |
| Eucalyptus | 1/9/2001 | — | T14 | codA |
| Eucalyptus | 2/1/2001 | — | T14 | codA |
| Eucalyptus | | — | T15 | des9 |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T7; T3 | cry34Ab1; cry35Ab1; pat |
| Maize | 676 | PH-000676-7 | T3; T18 | pat; dam |
| Maize | 678 | PH-000678-9 | T3; T18 | pat; dam |
| Maize | 680 | PH-000680-2 | T3; T18 | pat; dam |
| Maize | 98140 | DP-098140-6 | T1; T11 | gat4621; zm-hra |
| Maize | Bt10 | — | T7; T3 | cry1Ab; pat |
| Maize | Bt176 (176) | SYN-EV176-9 | T7; T3 | cry1Ab; bar |
| Maize | BVLA430101 | — | T4 | phyA2 |
| Maize | CBH-351 | ACS-ZM004-3 | T7; T3 | cry9C; bar |
| Maize | DAS40278-9 | DAS40278-9 | T19 | aad-1 |
| Maize | DBT418 | DKB-89614-9 | T7; T3 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | FI117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |

TABLE II-continued

| Crop | Event Name | Event Code | Trait(s) | Gene(s) |
|---|---|---|---|---|
| Maize | MIR604 | SYN-IR604-5 | T7 | mcry3A |
| Maize | MON801 (MON80100) | MON801 | T7; T1 | cry1Ab; cp4 epsps (aroA:CP4); goxv247 |
| Maize | MON802 | MON-80200-7 | T7; T1 | cry1Ab; cp4 epsps (aroA:CP4); goxv247 |
| Maize | MON809 | PH-MON-809-2 | T7; T1 | cry1Ab; cp4 epsps (aroA:CP4); goxv247 |
| Maize | MON810 | MON-00810-6 | T7; T1 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T7; T1 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3; T18 | bar; bar-se |
| Maize | MS6 | ACS-ZM005-4 | T3; T18 | bar; bar-se |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T7; T3 | cry1Fa2; pat |
| Maize | TC6275 | DAS-06275-8 | T7; T3 | mocry1F; bar |
| Maize | VIP1034 | — | T7; T3 | vip3A; pat |
| Maize | 43A47 | DP-043A47-3 | T7; T3 | cry1F; cry34Ab1; cry35Ab1; pat |
| Maize | 40416 | DP-040416-8 | T7; T3 | cry1F; cry34Ab1; cry35Ab1; pat |
| Maize | 32316 | DP-032316-8 | T7; T3 | cry1F; cry34Ab1; cry35Ab1; pat |
| Maize | 4114 | DP-004114-3 | T7; T3 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Petunia | Petunia-CHS | — | T25 | CHS suppres.sion |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Poplar | Bt poplar | — | T7 | cry1Ac; API |
| Poplar | Hybrid poplar clone 741 | — | T7 | cry1Ac; API |
| Poplar | trg300-l | — | T24 | AaXEG2 |
| Poplar | trg300-2 | — | T24 | AaXEG2 |
| Potato | 1210 amk | — | T7 | cry3A |
| Potato | 2904/1 kgs | — | T7 | cry3A |
| Canola** | ZSR500 | — | T1 | cp4 epsps (aroA:CP4); goxv247 |
| Canola** | ZSR502 | — | T1 | cp4 epsps (aroA:CP4); goxv247 |
| Potato | ATBT04-27 | NMK-89367-8 | T7 | cry3A |
| Potato | ATBT04-30 | NMK-89613-2 | T7 | cry3A |
| Potato | ATBT04-31 | NMK-89170-9 | T7 | cry3A |
| Potato | ATBT04-36 | NMK-89279-1 | T7 | cry3A |
| Potato | ATBT04-6 | NMK-89761-6 | T7 | cry3A |
| Potato | BT06 | NMK-89812-3 | T7 | cry3A |
| Potato | BT10 | NMK-89175-5 | T7 | cry3A |
| Potato | BT12 | NMK-89601-8 | T7 | cry3A |
| Potato | BT16 | NMK-89167-6 | T7 | cry3A |
| Potato | BT17 | NMK-89593-9 | T7 | cry3A |
| Potato | BT18 | NMK-89906-7 | T7 | cry3A |
| Potato | BT23 | NMK-89675-1 | T7 | cry3A |
| Potato | EH92-527-1 | BPS-25271-9 | T25 | gbss (antisense) |
| Potato | HLMT15-15 | — | T7; T6 | cry3A; pvy cp |
| Potato | HLMT15-3 | — | T7; T6 | cry3A; pvy cp |
| Potato | HLMT15-46 | — | T7; T6 | cry3A; pvy cp |
| Potato | RBMT15-101 | NMK-89653-6 | T7; T6 | cry3A; pvy cp |
| Potato | RBMT21-129 | NMK-89684-1 | T7; T6 | cry3A; plrv orf1; plrv orf2 |
| Potato | RBMT21-152 | — | T7; T6 | cry3A; plrv orf1; plrv orf2 |
| Potato | RBMT21-350 | NMK-89185-6 | T7; T6 | cry3A; plrv orf1; plrv orf2 |
| Potato | RBMT22-082 | NMK-89896-6 | T7; T6.; T1 | cry3A; plrv orf1; plrv orf2; cp4 epsps (aroA:CP4) |
| Potato | RBMT22-186 | — | T7; T6.; T1 | cry3A; plrv orf1; plrv orf2; cp4 epsps (aroA:CP4) |
| Potato | RBMT22-238 | — | T7; T6.; T1 | cry3A; plrv orf1; plrv orf2; cp4 epsps (aroA:CP4) |
| Potato | RBMT22-262 | — | T7; T6.; T1 | cry3A; plrv orf1; plrv orf2; cp4 epsps (aroA:CP4) |
| Potato | SEMT15-02 | NMK-89935-9 | T7; T6 | cry3A; pvy cp |
| Potato | SEMT15-07 | — | T7; T6 | cry3A; pvy cp |
| Potato | SEMT15-15 | NMK-89930-4 | T7; T6 | cry3A; pvy cp |

TABLE II-continued

| Crop | Event Name | Event Code | Trait(s) | Gene(s) |
|---|---|---|---|---|
| Potato | SPBT02-5 | NMK-89576-1 | T7 | cry3A |
| Potato | SPBT02-7 | NMK-89724-5 | T7 | cry3A |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13p-s-atAprt1 | — | T30 | Hv-S1; Hv-AT-A; APRT |
| Rice | 13pAprt1 | — | T30 | APRT |
| Rice | gHv-S1-gHv-AT-1 | — | T30 | Hv-S1; Hv-AT-A; Hv-AT-B |
| Rice | gHvIDS3-1 | — | T30 | HvIDS3 |
| Rice | gHv-AT1 | — | T30 | Hv-AT-A; Hv-AT-B |
| Rice | gHv-S1-1 | — | T30 | Hv-S1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T31; T11 | gm-fad2-1 (silencing locus); gm-hra |
| Soybean | DP356043 | DP-356043-5 | T31; T1 | gm-fad2-1 (silencing locus); gat4601 |
| Soybean | FG72 | MST-FG072-3 | T1; T32 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T31; T1 | fatb1-A (sense & antisense); fad2-1A (sense & antisense); cp4 epsps (aroA:CP4) |
| Soybean | MON87708 | MON-87708-9 | T12; T1 | dmo; cp4 epsps (aroA:CP4) |
| Soybean | MON87769 | MON-87769-7 | T31; T1 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34; T3 | Modified aad-12; pat |
| Soybean | DAS44406 | DAS-44406-6 | T34; T1; T3 | Modified aad-12; 2mepsps; pat |
| Soybean | SYHT04R | SYN-0004R-8 | T35 | Modified avhppd |
| Soybean | 9582.814.19.1 | | T7; T3 | cry1Ac; cry1F; pat |
| Squash | CZW3 | SEM-ØCZW3-2 | T6 | cmv cp; zymv cp; wmv cp |
| Squash | ZW20 | SEM-0ZW20-7 | T6 | zymv cp; wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |

TABLE II-continued

| Crop | Event Name | Event Code | Trait(s) | Gene(s) |
|---|---|---|---|---|
| Sugarcane | NXI-1T | — | T21 | EcbetA |
| Sunflower | X81359 | — | T16 | als |
| Sweet Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Tomato | 1345-4 | — | T22 | acc (truncated) |
| Tomato | 35-1-N | — | T22 | sam-k |
| Tomato | 5345 | — | T7 | cry1Ac |
| Tomato | 8338 | CGN-89322-3 | T22 | accd |
| Tomato | B | SYN-0000B-6 | T22 | pg (sense or antisense) |
| Tomato | Da | SYN-0000DA-9 | T22 | pg (sense or antisense) |
| Tomato | Da Dong No 9 | | T37 | — |
| Tomato | F (1401F, h38F, 11013F, 7913F) | SYN-0000F-1 | T22 | pg (sense or antisense) |
| Tomato | FLAVR SAVR ™ | CGN-89564-2 | T22 | pg (sense or antisense) |
| Tomato | Huafan No 1 | — | T22 | anti-efe |
| Tomato | PK-TM8805R (8805R) | — | T6 | cmv cp |
| Wheat | MON71800 | MON-718ØØ-3 | T1 | cp4 epsps (aroA:CP4) |

*Argentine,
**Polish,
Eggplant

Treatment of genetically modified plants and seeds with compounds of the invention may result in super-additive or synergistic effects. For example, reduction in application rates, broadening of the activity spectrum, increased tolerance to biotic/abiotic stresses or enhanced storage stability may be greater than expected from just simple additive effects of the application of compounds of the invention on genetically modified plants and seeds.

Compounds of this invention are useful in seed treatments for protecting seeds from plant diseases. In the context of the present disclosure and claims, treating a seed means contacting the seed with a biologically effective amount of a compound of this invention, which is typically formulated as a composition of the invention. This seed treatment protects the seed from soil-borne disease pathogens and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as Bacillus thuringiensis toxin or those expressing herbicide resistance such as glyphosate acetyltransferase, which provides resistance to glyphosate. Seed treatments with compounds of this invention can also increase vigor of plants growing from the seed.

Compounds of this invention and their compositions, both alone and in combination with other fungicides, nematicides and insecticides, are particularly useful in seed treatment for crops including, but not limited to, maize or corn, soybeans, cotton, cereal (e.g., wheat, oats, barley, rye and rice), potatoes, vegetables and oilseed rape.

Furthermore, the compounds of this invention are useful in treating postharvest diseases of fruits and vegetables caused by fungi and bacteria. These infections can occur before, during and after harvest. For example, infections can occur before harvest and then remain dormant until some point during ripening (e.g., host begins tissue changes in such a way that infection can progress); also infections can arise from surface wounds created by mechanical or insect injury. In this respect, the compounds of this invention can reduce losses (i.e. losses resulting from quantity and quality) due to postharvest diseases which may occur at any time from harvest to consumption. Treatment of postharvest diseases with compounds of the invention can increase the period of time during which perishable edible plant parts (e.g, fruits, seeds, foliage, stems, bulbs, tubers) can be stored refrigerated or un-refrigerated after harvest, and remain edible and free from noticeable or harmful degradation or contamination by fungi or other microorganisms. Treatment of edible plant parts before or after harvest with compounds of the invention can also decrease the formation of toxic metabolites of fungi or other microorganisms, for example, mycotoxins such as aflatoxins.

Plant disease control is ordinarily accomplished by applying an effective amount of a compound of this invention either pre- or post-infection, to the portion of the plant to be protected such as the roots, stems, foliage, fruits, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants. Control of postharvest pathogens which infect the produce before harvest is typically accomplished by field application of a compound of this invention, and in cases where infection occurs after harvest the compounds can be applied to the harvested crop as dips, sprays, fumigants, treated wraps and box liners.

Rates of application for these compounds (i.e. a fungicidally effective amount) can be influenced by factors such as the plant diseases to be controlled, the plant species to be protected, ambient moisture and temperature and should be determined under actual use conditions. One skilled in the art can easily determine through simple experimentation the fungicidally effective amount necessary for the desired level of plant disease control. Foliage can normally be protected when treated at a rate of from less than about 1 g/ha to about 5,000 g/ha of active ingredient. Seed and seedlings can normally be protected when seed is treated at a rate of from about 0.001 g (more typically about 0.1 g) to about 10 g per kilogram of seed. Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multicomponent pesticide giving an even broader spectrum of agricultural protection. Thus the present invention also pertains to a composition comprising a compound of Formula 1 (in a fungicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

As mentioned in the Summary of the Invention, one aspect of the present invention is a fungicidal composition comprising (i.e. a mixture or combination of) a compound of Formula 1, an N-oxide, or a salt thereof (i.e. component a), and at least one other fungicide (i.e. component b). Of note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a fungicidally effective amount of at least one additional fungicidal active ingredient having a similar spectrum of control but a different site of action.

Of note is a composition which in addition to the Formula 1 compound of component (a), includes as component (b) at least one fungicidal compound selected from the group consisting of the FRAC-defined mode of action (MOA) classes (A) nucleic acid synthesis, (B) mitosis and cell division, (C) respiration, (D) amino acid and protein synthesis, (E) signal transduction, (F) lipid synthesis and membrane integrity, (G) sterol biosynthesis in membranes, (H) cell wall biosynthesis in membranes, (I) melanin synthesis in cell wall, (P) host plant defense induction, multi-site contact activity and unknown mode of action.

FRAC-recognized or proposed target sites of action along with their FRAC target site codes belonging to the above MOA classes are (A1) RNA polymerase I, (A2) adenosine deaminase, (A3) DNA/RNA synthesis (proposed), (A4) DNA topoisomerase, (B1-B3) β-tubulin assembly in mitosis, (B4) cell division (proposed), (B5) delocalization of spectrin-like proteins, (C1) complex I NADH odxido-reductase, (C2) complex II: succinate dehydrogenase, (C3) complex III: cytochrome bc1 (ubiquinol oxidase) at Qo site, (C4) complex III: cytochrome bc1 (ubiquinone reductase) at Qi site, (C5) uncouplers of oxidative phosphorylation, (C6) inhibitors of oxidative phosphorylation, ATP synthase, (C7) ATP production (proposed), (C8) complex III: cytochrome bc1 (ubiquinone reductase) at Qx (unknown) site, (D1) methionine biosynthesis (proposed), (D2-D5) protein synthesis, (E1) signal transduction (mechanism unknown), (E2-E3) MAP/histidine kinase in osmotic signal transduction, (F2) phospholipid biosynthesis, methyl transferase, (F3) lipid peroxidation (proposed), (F4) cell membrane permeability, fatty acids (proposed), (F6) microbial disrupters of pathogen cell membranes, (F7) cell membrane disruption (proposed), (G1) C14-demethylase in sterol biosynthesis, (G2) Δ14-reductase and Δ8→Δ7-isomerase in sterol biosynthesis, (G3) 3-keto reductase, C4-demethylation, (G4) squalene epoxidase in sterol biosynthesis, (H3) trehalase and inositol biosynthesis, (H4) chitin synthase, (H5) cellulose synthase, (I1) reductase in melanin biosynthesis and (I2) dehydratase in melanin biosynthesis.

Of particular note is a composition which in addition to the Formula 1 compound of component (a), includes as component (b) at least one fungicidal compound selected from the group consisting of the classes (b1) methyl benzimidazole carbamate (MBC) fungicides; (b2) dicarboximide fungicides; (b3) demethylation inhibitor (DMI) fungicides; (b4) phenylamide fungicides; (b5) amine/morpholine fungicides; (b6) phospholipid biosynthesis inhibitor fungicides; (b7) succinate dehydrogenase inhibitor fungicides; (b8) hydroxy(2-amino-)pyrimidine fungicides; (b9) anilinopyrimidine fungicides; (b10) N-phenyl carbamate fungicides; (b11) quinone outside inhibitor (QoI) fungicides; (b12) phenylpyrrole fungicides; (b13) azanaphthalene fungicides; (b14) lipid peroxidation inhibitor fungicides; (b15) melanin biosynthesis inhibitor-reductase (MBI-R) fungicides; (b16) melanin biosynthesis inhibitor-dehydratase (MBI-D) fungicides; (b17) sterol biosynthesis inhibitor (SBI): Class III fungicides; (b18) squalene-epoxidase inhibitor fungicides; (b19) polyoxin fungicides; (b20) phenylurea fungicides; (b21) quinone inside inhibitor (QiI) fungicides; (b22) benzamide and thiazole carboxamide fungicides; (b23) enopyranuronic acid antibiotic fungicides; (b24) hexopyranosyl antibiotic fungicides; (b25) glucopyranosyl antibiotic: protein synthesis fungicides; (b26) glucopyranosyl antibiotic: trehalase and inositol biosynthesis fungicides; (b27) cyanoacetamideoxime fungicides; (b28) carbamate fungicides; (b29) oxidative phosphorylation uncoupling fungicides; (b30) organo tin fungicides; (b31) carboxylic acid fungicides; (b32) heteroaromatic fungicides; (b33) phosphonate fungicides; (b34) phthalamic acid fungicides; (b35) benzotriazine fungicides; (b36) benzene-sulfonamide fungicides; (b37) pyridazinone fungicides; (b38) thiophene-carboxamide fungicides; (b39) complex I NADH oxidoreductase inhibitor fungicides; (b40) carboxylic acid amide (CAA) fungicides; (b41) tetracycline antibiotic fungicides; (b42) thiocarbamate fungicides; (b43) benzamide fungicides; (b44) microbial fungicides; (b45) $Q_xI$ fungicides; (b46) plant extract fungicides; (b47) host plant defense induction fungicides; (b48) multi-site contact activity fungicides; (b49) fungicides other than fungicides of classes (b1) through (b48); and salts of compounds of classes (b1) through (b48).

Further descriptions of these classes of fungicidal compounds are provided below.

(b1) "Methyl benzimidazole carbamate (MBC) fungicides" (FRAC code 1) inhibit mitosis by binding to β-tubulin during microtubule assembly Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(b2) "Dicarboximide fungicides" (FRAC code 2) inhibit a MAP/histidine kinase in osmotic signal transduction. Examples include chlozolinate, iprodione, procymidone and vinclozolin.

(b3) "Demethylation inhibitor (DMI) fungicides" (FRAC code 3) (Sterol Biosynthesis Inhibitors (SBI): Class I) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. DMI fungicides are divided between several chemical classes: azoles (including triazoles and imidazoles), pyrimidines, piperazines, pyridines and triazolinthiones. The triazoles include azaconazole, bitertanol, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, quinconazole, simeconazole, tebuconazole, tetraconazole, triadimefon, triadimenol, triticonazole, uniconazole, uniconazole-P, α-(1-chlorocyclopropyl)-α-[2-(2,2-dichlorocyclopropyl)ethyl]-1H-1,2,4-triazole-1-ethanol, rel-1-[[(2R,3S)-3-(2-chlorophenyl)-2-(2,4-difluorophenyl)-2-oxiranyl]methyl]-1H-1,2,4-triazole, rel-2-[[(2R,3S)-3-(2-chlorophenyl)-2-(2,4-difluorophenyl)-2-oxiranyl]methyl]-1,2-dihydro-3H-1,2,4-triazole-3-thione, and rel-1-[[(2R,3S)-3-(2-chlorophenyl)-2-(2,4-difluorophenyl)-2-oxiranyl]methyl]-5-(2-propen-1-ylthio)-1H-1,2,4-triazole. The imidazoles include econazole, imazalil, oxpoconazole, prochloraz, pefurazoate and triflumizole. The pyrimidines include fenarimol, nuarimol and triarimol. The piperazines include triforine. The pyridines include buthiobate, pyrifenox, pyrisoxazole (3-[(3R)-5-(4-chlorophenyl)-2,3-dimethyl-3-isoxazolidinyl]pyridine, mixture of 3R,5R- and 3R,5S-isomers) and (αS)-[3-(4-chloro-2-fluorophenyl)-5-(2,4-difluorophenyl)-4-isoxazolyl]-3-pyridinemethanol. The triazolinthiones include prothioconazole and 2-[2-(1-chlorocyclopropyl)-4-(2,2-dichlorocyclopropyl)-2-hydroxybutyl]-1,2-dihydro-3H-1,2,4-triazole-3-thione. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(b4) "Phenylamide fungicides" (FRAC code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M (also known as kiralaxyl), furalaxyl, metalaxyl and metalaxyl-M (also known as mefenoxam). The oxazolidinones include oxadixyl. The butyrolactones include ofurace.

(b5) "Amine/morpholine fungicides" (FRAC code 5) (SBI: Class II) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(b6) "Phospholipid biosynthesis inhibitor fungicides" (FRAC code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

(b7) "Succinate dehydrogenase inhibitor (SDHI) fungicides" (FRAC code 7) inhibit Complex II fungal respiration by disrupting a key enzyme in the Krebs Cycle (TCA cycle) named succinate dehydrogenase. Inhibiting respiration prevents the fungus from making ATP, and thus inhibits growth and reproduction. SDHI fungicides include phenylbenzamide, furan carboxamide, oxathiin carboxamide, thiazole carboxamide, pyrazole-4-carboxamide, pyridine carboxamide, phenyl oxoethyl thiophene amides and pyridinylethyl benzamides The benzamides include benodanil, flutolanil and mepronil. The furan carboxamides include fenfuram. The oxathiin carboxamides include carboxin and oxycarboxin. The thiazole carboxamides include thifluzamide. The pyrazole-4-carboxamides include benzovindiflupyr (N-[9-(dichloromethylene)-1,2,3,4-tetrahydro-1,4-methanonaphthalen-5-yl]-3-(difluoromethyl)-1-methyl-1H-pyrazole-4-carboxamide), bixafen, fluxapyroxad (3-(difluoromethyl)-1-methyl-N-(3',4',5'-trifluoro[1,1'-biphenyl]-2-yl)-1H-pyrazole-4-carboxamide), furametpyr, isopyrazam (3-(difluoromethyl)-1-methyl-N-[1,2,3,4-tetrahydro-9-(1-methylethyl)-1,4-methanonaphthalen-5-yl]-1H-pyrazole-4-carboxamide), penflufen (N-[2-(1,3-dimethylbutyl)phenyl]-5-fluoro-1,3-dimethyl-1H-pyrazole-4-carboxamide), penthiopyrad, sedaxane (N-[2-[1,1'-bicyclopropyl]-2-ylphenyl]-3-(difluoromethyl)-1-methyl-1H-pyrazole-4-carboxamide), N-[2-(1S,2R)-[1,1'-bicyclopropyl]-2-ylphenyl]-3-(difluoromethyl)-1-methyl-1H-pyrazole-4-carboxamide, 3-(difluoromethyl)-N-(2,3-dihydro-1,1,3-trimethyl-1H-inden-4-yl)-1-methyl-1H-pyrazole-4-carboxamide, N-[2-(2,4-dichlorophenyl)-2-methoxy-1-methylethyl]-3-(difluoromethyl)-1-methyl-1H-pyrazole-4-carboxamide and N-cyclopropyl-3-(difluoromethyl)-5-fluoro-1-methyl-N-[[2-(1-methyl-ethyl)phenyl]methyl]-1H-pyrazole-4-carboxamide. The pyridine carboxamides include boscalid. The phenyl oxoethyl thiophene amides include isofetamid (N-[1,1-dimethyl-2-[2-methyl-4-(1-methylethoxy)phenyl]-2-oxoethyl]-3-methyl-2-thiophenecarboxamide). The pyridinylethyl benzamides include fluopyram.

(b8) "Hydroxy-(2-amino-)pyrimidine fungicides" (FRAC code 8) inhibit nucleic acid synthesis by interfering with adenosine deaminase. Examples include bupirimate, dimethirimol and ethirimol.

(b9) "Anilinopyrimidine fungicides" (FRAC code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(b10) "N-Phenyl carbamate fungicides" (FRAC code 10) inhibit mitosis by binding to β-tubulin and disrupting microtubule assembly. Inhibition of microtubule assembly can disrupt cell division, transport within the cell and cell structure. Examples include diethofencarb.

(b11) "Quinone outside inhibitor (QoI) fungicides" (FRAC code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi Inhibiting mitochondrial respiration prevents normal fungal growth and development. Quinone outside inhibitor fungicides include methoxyacrylate, methoxycarbamate, oximinoacetate, oximinoacetamide and dihydrodioxazine fungicides (collectively also known as strobilurin fungicides), and oxazolidinedione, imidazolinone and benzylcarbamate fungicides. The methoxyacrylates include azoxystrobin, coumoxystrobin (methyl(αE)-2-[[(3-butyl-4-methyl-2-oxo-2H-1-benzopyran-7-yl)oxy]methyl]-α-(methoxymethylene)benzeneacetate), enoxastrobin (methyl(αE)-2-[[[(E)-[(2E)-3-(4-chlorophenyl)-1-methyl-2-propen-1-ylidene]amino]oxy]methyl]-α-(methoxymethylene)benzeneacetate) (also known as enestroburin), flufenoxystrobin (methyl(αE)-2-[[2-chloro-4-(trifluoromethyl)phenoxy]methyl]-α-(methoxymethylene)benzeneacetate), picoxystrobin and pyraoxystrobin (methyl (αE)-2-[[[3-(4-chlorophenyl)-1-methyl-1H-pyrazol-5-yl]oxy]methyl]-α-(methoxymethylene)benzeneacetate). The methoxycarbamates include pyraclostrobin, pyrametostrobin (methyl N-[2-[[(1,4-dimethyl-3-phenyl-1H-pyrazol-5-yl)oxy]methyl]phenyl]-N-methoxycarbamate) and triclopyricarb (methyl N-methoxy-N-[2-[[(3,5,6-trichloro-2-pyridinyl)oxy]methyl]phenyl]carbamate). The oximinoacetates include kresoxim-methyl and trifloxystrobin. The oximinoacetamides include dimoxystrobin, fenaminstrobin ((αE)-2-[[[(E)-[(2E)-3-(2,6-dichlorophenyl)-1-methyl-2-propen-1-ylidene]amino]oxy]methyl]-α-(methoxyimino)-N-methylbenzeneacetamide), metominostrobin, orysastrobin and α-[methoxyimino]-N-methyl-2-[[[1-[3-(trifluoro-methyl)phenyl]ethoxy]imino]methyl]benzeneacetamide. The dihydrodioxazines include fluoxastrobin. The oxazolidinediones include famoxadone. The imidazolinones include fenamidone. The benzylcarbamates include pyribencarb. Class (b11) also includes mandestrobin (2-[(2,5-dimethylphenoxy)methyl]-α-methoxy-N-benzeneacetamide).

(b12) "Phenylpyrrole fungicides" (FRAC code 12) inhibit a MAP/histidine kinase associated with osmotic signal transduction in fungi. Fenpiclonil and fludioxonil are examples of this fungicide class.

(b13) "Azanaphthalene fungicides" (FRAC code 13) are proposed to inhibit signal transduction by a mechanism which is as yet unknown. They have been shown to interfere with germination and/or appressorium formation in fungi that cause powdery mildew diseases. Azanaphthalene fungicides include aryloxyquinolines and quinazolinones. The aryloxyquinolines include quinoxyfen. The quinazolinones include proquinazid.

(b14) "Lipid peroxidation inhibitor fungicides" (FRAC code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic hydrocarbon and 1,2,4-thiadiazole fungicides. The aromatic hydrocarboncarbon fungicides include biphenyl, chloroneb, dicloran, quintozene, tecnazene and tolclofos-methyl. The 1,2,4-thiadiazoles include etridiazole.

(b15) "Melanin biosynthesis inhibitors-reductase (MBI-R) fungicides" (FRAC code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(b16) "Melanin biosynthesis inhibitors-dehydratase (MBI-D) fungicides" (FRAC code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(b17) "Sterol Biosynthesis Inhibitor (SBI): Class III fungicides (FRAC code 17) inhibit 3-ketoreductase during C4-demethylation in sterol production. SBI: Class III inhibitors include hydroxyanilide fungicides and amino-pyrazolinone fungicides. Hydroxyanilides include fenhexamid. Amino-pyrazolinones include fenpyrazamine (S-2-propen-1-yl 5-amino-2,3-dihydro-2-(1-methylethyl)-4-(2-methylphenyl)-3-oxo-1H-pyrazole-1-carbothioate).

(b18) "Squalene-epoxidase inhibitor fungicides" (FRAC code 18) (SBI: Class IV) inhibit squalene-epoxidase in the sterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(b19) "Polyoxin fungicides" (FRAC code 19) inhibit chitin synthase. Examples include polyoxin.

(b20) "Phenylurea fungicides" (FRAC code 20) are proposed to affect cell division. Examples include pencycuron.

(b21) "Quinone inside inhibitor (QiI) fungicides" (FRAC code 21) inhibit Complex III mitochondrial respiration in fungi by affecting ubiquinone reductase. Reduction of ubiquinone is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(b22) "Benzamide and thiazole carboxamide fungicides" (FRAC code 22) inhibit mitosis by binding to β-tubulin and disrupting microtubule assembly. Inhibition of microtubule assembly can disrupt cell division, transport within the cell and cell structure. The benzamides include zoxamide. The thiazole carboxamides include ethaboxam.

(b23) "Enopyranuronic acid antibiotic fungicides" (FRAC code 23) inhibit growth of fungi by affecting protein biosynthesis. Examples include blasticidin-S.

(b24) "Hexopyranosyl antibiotic fungicides" (FRAC code 24) inhibit growth of fungi by affecting protein biosynthesis. Examples include kasugamycin.

(b25) "Glucopyranosyl antibiotic: protein synthesis fungicides" (FRAC code 25) inhibit growth of fungi by affecting protein biosynthesis. Examples include streptomycin.

(b26) "Glucopyranosyl antibiotic: trehalase and inositol biosynthesis fungicides" (FRAC code 26) inhibit trehalase and inositol biosynthesis. Examples include validamycin.

(b27) "Cyanoacetamideoxime fungicides (FRAC code 27) include cymoxanil.

(b28) "Carbamate fungicides" (FRAC code 28) are considered multi-site inhibitors of fungal growth. They are proposed to interfere with the synthesis of fatty acids in cell membranes, which then disrupts cell membrane permeability. Propamacarb, iodocarb, and prothiocarb are examples of this fungicide class.

(b29) "Oxidative phosphorylation uncoupling fungicides" (FRAC code 29) inhibit fungal respiration by uncoupling oxidative phosphorylation. Inhibiting respiration prevents normal fungal growth and development. This class includes 2,6-dinitroanilines such as fluazinam, and dinitrophenyl crotonates such as dinocap, meptyldinocap and binapacryl.

(b30) "Organo tin fungicides" (FRAC code 30) inhibit adenosine triphosphate (ATP) synthase in oxidative phosphorylation pathway. Examples include fentin acetate, fentin chloride and fentin hydroxide.

(b31) "Carboxylic acid fungicides" (FRAC code 31) inhibit growth of fungi by affecting deoxyribonucleic acid (DNA) topoisomerase type II (gyrase). Examples include oxolinic acid.

(b32) "Heteroaromatic fungicides" (Fungicide Resistance Action Committee (FRAC) code 32) are proposed to affect DNA/ribonucleic acid (RNA) synthesis. Heteroaromatic fungicides include isoxazoles and isothiazolones. The isoxazoles include hymexazole and the isothiazolones include octhilinone.

(b33) "Phosphonate fungicides" (FRAC code 33) include phosphorous acid and its various salts, including fosetyl-aluminum.

(b34) "Phthalamic acid fungicides" (FRAC code 34) include teclofthalam.

(b35) "Benzotriazine fungicides" (FRAC code 35) include triazoxide.

(b36) "Benzene-sulfonamide fungicides" (FRAC code 36) include flusulfamide.

(b37) "Pyridazinone fungicides" (FRAC code 37) include diclomezine.

(b38) "Thiophene-carboxamide fungicides" (FRAC code 38) are proposed to affect ATP production. Examples include silthiofam.

(b39) "Complex I NADH oxidoreductase inhibitor fungicides" (FRAC code 39) inhibit electron transport in mitochondria and include pyrimidinamines such as diflumetorim, and pyrazole-5-carboxamides such as tolfenpyrad.

(b40) "Carboxylic acid amide (CAA) fungicides" (FRAC code 40) inhibit cellulose synthase which prevents growth and leads to death of the target fungus. Carboxylic acid amide fungicides include cinnamic acid amide, valinamide and other carbamate, and mandelic acid amide fungicides. The cinnamic acid amides include dimethomorph, flumorph and pyrimorph (3-(2-chloro-4-pyridinyl)-3-[4-(1,1-dimethylethyl)phenyl]-1-(4-morpholinyl)-2-propene-1-one). The valinamide and other carbamates include benthiavalicarb, benthiavalicarb-isopropyl, iprovalicarb, tolprocarb (2,2,2-trifluoroethyl N-[(1S)-2-methyl-1-[[(4-methylbenzoyl)amino]methyl]propyl]carbamate) and valifenalate (methyl N-[(1-methylethoxy)carbonyl]-L-valyl-3-(4-chlorophenyl)-β-alaninate) (also known as valiphenal). The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)-amino]butanamide and N-[2-[4-[[3-(4-chlorophenyl)-2-propyn-1-yl]oxy]-3-methoxyphenyl]-ethyl]-3-methyl-2-[(ethylsulfonyl)amino]butanamide.

(b41) "Tetracycline antibiotic fungicides" (FRAC code 41) inhibit growth of fungi by affecting protein synthesis. Examples include oxytetracycline.

(b42) "Thiocarbamate fungicides" (FRAC code 42) include methasulfocarb.

(b43) "Benzamide fungicides" (FRAC code 43) inhibit growth of fungi by delocalization of spectrin-like proteins. Examples include pyridinylmethyl benzamide fungicides such as fluopicolide (now FRAC code 7, pyridinylethyl benzamides).

(b44) "Microbial fungicides" (FRAC code 44) disrupt fungal pathogen cell membranes. Microbial fungicides include *Bacillus* species such as *Bacillus amyloliquefaciens* strains QST 713, FZB24, MB1600, D747 and the fungicidal lipopeptides which they produce.

(b45) "$Q_xI$ fungicides" (FRAC code 45) inhibit Complex III mitochondrial respiration in fungi by affecting ubiquinone reductase at an unknown ($Q_x$) site of the cytochrome $bc_1$ complex. Inhibiting mitochondrial respiration prevents normal fungal growth and development. $Q_xI$ fungicides include triazolopyrimidylamines such as ametoctradin (5-ethyl-6-octyl[1,2,4]triazolo[1,5-a]pyrimidin-7-amine).

(b46) "Plant extract fungicides" are proposed to act by cell membrane disruption. Plant extract fungicides include terpene hydrocarbons and terpene alcohols such as the extract from *Melaleuca alternifolia* (tea tree).

(b47) "Host plant defense induction fungicides" (FRAC code P) induce host plant defense mechanisms. Host plant defense induction fungicides include benzothiadiazoles, benzisothiazole and thiadiazole-carboxamide fungicides. The benzothiadiazoles include acibenzolar-S-methyl. The benzisothiazoles include probenazole. The thiadiazole-carboxamides include tiadinil and isotianil.

(b48) "Multi-site contact fungicides" inhibit fungal growth through multiple sites of action and have contact/preventive activity. This class of fungicides includes: (b48.1) "copper fungicides" (FRAC code M1)", (b48.2) "sulfur fungicides" (FRAC code M2), (b48.3) "dithiocarbamate fungicides" (FRAC code M3), (b48.4) "phthalimide fungicides" (FRAC code M4), (b48.5) "chloronitrile fungicides" (FRAC code M5), (b48.6) "sulfamide fungicides" (FRAC code M6), (b48.7) multi-site contact "guanidine fungicides" (FRAC code M7), (b48.8) "triazine fungicides" (FRAC code M8), (b48.9) "quinone fungicides" (FRAC code M9), (b48.10) "quinoxaline fungicides" (FRAC code M10) and (b48.11) "maleimide fungicides" (FRAC code M11). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. Multi-site contact "guanidine fungicides" include, guazatine, iminoctadine albesilate and iminoctadine triacetate. "Triazine fungicides" include anilazine. "Quinone fungicides" include dithianon. "Quinoxaline fungicides" include quinomethionate (also known as chinomethionate). "Maleimide fungicides" include fluoroimide.

(b49) "Fungicides other than fungicides of classes (b1) through (b48)" include certain fungicides whose mode of action may be unknown. These include: (b49.1) "phenyl-acetamide fungicides" (FRAC code U6), (b49.2) "aryl-phenyl-ketone fungicides" (FRAC code U8), (b49.3) "guanidine fungicides" (FRAC code U12), (b49.4) "thiazolidine fungicides" (FRAC code U13), (b49.5) "pyrimidinone-hydrazone fungicides" (FRAC code U14) and (b49.6) compounds that bind to oxysterol-binding protein as described in PCT Patent Publication WO 2013/009971. The phenyl-acetamides include cyflufenamid and N-[[cyclopropylmethoxy)amino][6-(difluoromethoxy)-2,3-difluorophenyl]-methylene]-benzeneacetamide. The aryl-phenyl ketones include benzophenones such as metrafenone, and benzoylpyridines such as pyriofenone ((5-chloro-2-methoxy-4-methyl-3-pyridinyl)(2,3,4-trimethoxy-6-methyl-phenyl)methanone). The guanidines include dodine. The thiazolidines include flutianil ((2Z)-2-[[2-fluoro-5-(trifluoromethyl)phenyl]thio]-2-[3-(2-methoxyphenyl)-2-thiazolidinylidene]acetonitrile). The pyrimidinone-hydrazones include ferimzone. The (b49.6) class includes oxathiapiprolin (1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone) and its R-enantiomer which is 1-[4-[4-[5R-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone (Registry Number 1003319-79-6).

The (b49) class also includes bethoxazin, flometoquin (2-ethyl-3,7-dimethyl-6-[4-(trifluoromethoxy)phenoxy]-4-quinolinyl methyl carbonate), fluoroimide, neo-asozin (ferric methanearsonate), picarbutrazox (1,1-dimethylethyl N-[6-[[[[((Z)-1-methyl-1H-tetrazol-5-yl)phenylmethylene]amino]oxy]methyl]-2-pyridinyl]carbamate), pyrrolnitrin, quinomethionate, tebufloquin (6-(1,1-dimethylethyl)-8-fluoro-2,3-dimethyl-4-quinolinyl acetate), tolnifanide (N-(4-chloro-2-nitrophenyl)-N-ethyl-4-methylbenzenesulfonamide), 2-butoxy-6-iodo-3-propyl-4H-1-benzopyran-4-one, 3-butyn-1-yl N-[6-[[[[(1-methyl-1H-tetrazol-5-yl)phenylmethylene]amino]oxy]methyl]-2-pyridinyl]carbamate, (N-(4-chloro-2-nitrophenyl)-N-ethyl-4-methylbenzenesulfonamide), N-[4-[4-chloro-3-(trifluoromethyl)-phenoxy]-2,5-dimethylphenyl]-N-ethyl-N-methylmethanimidamide, N-[[(cyclopropyl-methoxy)amino][6-(difluoromethoxy)-2,3-difluorophenyl]methylene]benzeneacetamide, 2,6-dimethyl-1H,5H-[1,4]dithiino[2,3-c:5,6-c']dipyrrole-1,3,5,7 (2H,6H)-tetrone, 5-fluoro-2-[(4-methylphenyl)methoxy]-4-pyrimidinamine, 5-fluoro-2-[(4-fluorophenyl)methoxy]-4-pyrimidinamine and 4-fluorophenyl N-[1-[[[1-(4-cyanophenyl)ethyl]sulfonyl]methyl]-propyl]carbamate, pentyl N-[6-[[[[(1-methyl-1H-tetrazol-5-yl)phenyl-methylene]amino]oxy]methyl]-2-pyridinyl]carbamate, pentyl N-[4-[[[[(1-methyl-1H-tetrazol-5-yl)phenylmethylene]amino]oxy]methyl]-2-thiazolyl]carbamate and pentyl N-[6-[[[[(Z)-(1-methyl-1H-tetrazol-5-yl)phenylmethylene]amino]oxy]methyl]-2-pyridinyl]-carbamate. The (b49) class further includes mitosis- and cell division-inhibiting fungicides besides those of the particular classes described above (e.g., (b1), (b10) and (b22)).

Additional "Fungicides other than fungicides of classes (b1) through (b48)" whose mode of action may be unknown, or may not yet be classified include a fungicidal compound selected from components (b49.7) through (b49.12), as shown below.

Component (b49.7) relates to a compound of Formula b49.7

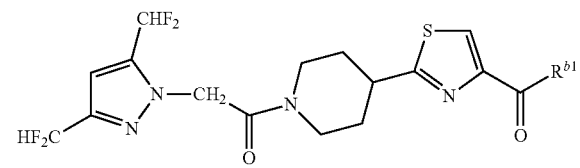

b49.7 wherein $R^{b1}$ is

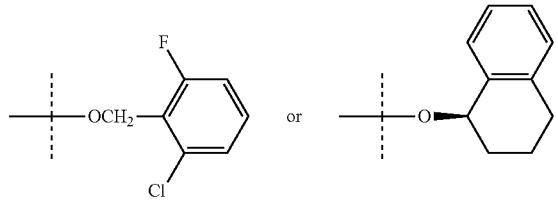

Examples of a compound of Formula b49.7 include (b49.7a) (2-chloro-6-fluorophenyl)-methyl 2-[1-[2-[3,5-bis(difluoromethyl)-1H-pyrazol-1-yl]acetyl]-4-piperidinyl]-4-thiazole-carboxylate (Registry Number 1299409-40-7) and (b49.7b) (1R)-1,2,3,4-tetrahydro-1-naphthalenyl 2-[1-[2-[3,5-bis(difluoromethyl)-1H-pyrazol-1-yl]acetyl]-4-piperidinyl]-4-thiazolecarboxylate (Registry Number 1299409-42-9). Methods for preparing compounds of Formula b49.7 are described in PCT Patent Publications WO 2009/132785 and WO 2011/051243.

Component (b49.8) relates to a compound of Formula b49.8

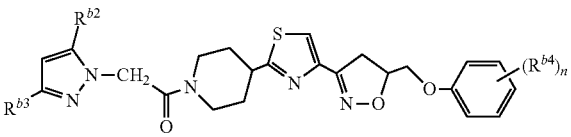

b49.8 wherein $R^{b2}$ is $CH_3$, $CF_3$ or $CHF_2$; $R^{b3}$ is $CH_3$, $CF_3$ or $CHF_2$; $R^{b4}$ is halogen or cyano; and n is 0, 1, 2 or 3. Examples of a compound of Formula b49.8 include (b49.8a) 1-[4-[4-[5-[(2,6-difluorophenoxy)methyl]-4,5-dihydro-3-isoxazolyl]-2-thiazolyl]-1-piperidinyl]-2-[5-methyl-3-(trifluoromethyl)-1H-pyrazol-1-yl]ethanone. Methods for preparing compounds of Formula b49.8 are described in PCT Patent Application PCT/US11/64324.

Component (b49.9) relates to a compound of Formula b49.9

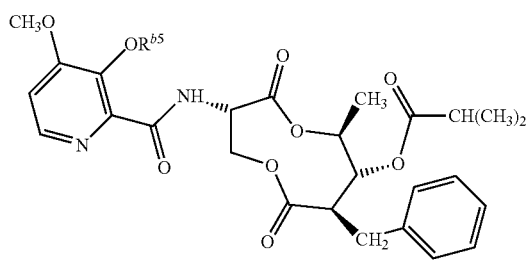

b49.9 wherein $R^{b5}$ is $-CH_2OC(O)CH(CH_3)_2$, $-C(O)CH_3$, $-CH_2OC(O)CH_3$, $-C(O)OCH_2CH(CH_3)_2$ or

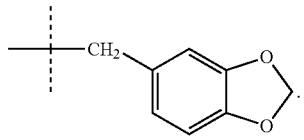

Examples of a compound of Formula b49.9 include (b49.9a) [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]carbonyl]-3-pyridinyl]oxy]methyl 2-methylpropanoate (Registry Number 517875-34-2), (b49.9b) (3S,6S,7R,8R)-3-[[[3-(acetyloxy)-4-methoxy-2-pyridinyl]-carbonyl]amino]-6-methyl-4,9-dioxo-8-(phenylmethyl)-1,5-dioxonan-7-yl 2-methyl-propanoate (Registry Number 234112-93-7), (b49.9c) (3S,6S,7R,8R)-3-[[[3-[(acetyloxy)methoxy]-4-methoxy-2-pyridinyl]carbonyl]amino]-6-methyl-4,9-dioxo-8-(phenylmethyl)-1,5-dioxonan-7-yl 2-methylpropanoate (Registry Number 517875-31-9), (b49.9d) (3S,6S,7R,8R)-3-[[[4-methoxy-3-[[(2-methylpropoxy)carbonyl]oxy]-2-pyridinyl]-carbonyl]amino]-6-methyl-4,9-dioxo-8-(phenylmethyl)-1,5-dioxonan-7-yl 2-methylpropanoate (Registry Number 328256-72-0), and (b49.9e) N-[[3-(1,3-benzodioxol-5-ylmethoxy)-4-methoxy-2-pyridinyl]carbonyl]-O-[2,5-dideoxy-3-O-(2-methyl-1-oxopropyl)-2-(phenylmethyl)-L-arabinonoyl]-L-serine, (1→4)-lactone (Registry Number 1285706-70-8). Methods for preparing compounds of Formula b49.9 are described in PCT Patent Publications WO 99/40081, WO 2001/014339, WO 2003/035617 and WO 2011044213.

Component (b49.10) relates to a compound of Formula b49.10

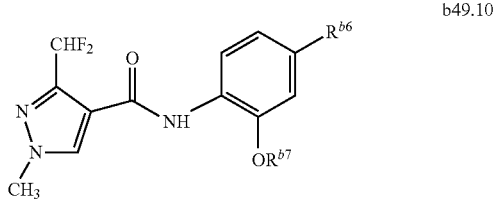

b49.10 wherein $R^{b6}$ is H or F, and $R^{b7}$ is —CF$_2$CHFCF$_3$ or —CF$_2$CF$_2$H. Examples of a compound of Formula b49.10 are (b49.10a) 3-(difluoromethyl)-N-[4-fluoro-2-(1,1,2,3,3,3-hexafluoro-propoxy)phenyl]-1-methyl-1H-pyrazole-4-carboxamide (Registry Number 1172611-40-3) and (b49.10b) 3-(difluoromethyl)-1-methyl-N-[2-(1,1,2,2-tetrafluoroethoxy)phenyl]-1H-pyrazole-4-carboxamide (Registry Number 923953-98-4). Compounds of Formula 49.10 can be prepared by methods described in PCT Patent Publication WO 2007/017450.

Component b49.11 relates a compound of Formula b49.11

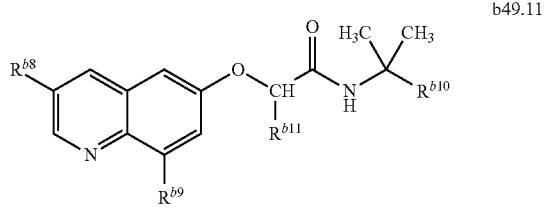

b49.11 wherein
$R^{b8}$ is halogen, $C_1$-$C_4$ alkoxy or $C_2$-$C_4$ alkynyl;
$R^{b9}$ is H, halogen or $C_1$-$C_4$ alkyl;
$R^{b10}$ is $C_1$-$C_{12}$ alkyl, $C_1$-$C_{12}$ haloalkyl, $C_1$-$C_{12}$ alkoxy, $C_2$-$C_{12}$ alkoxyalkyl, $C_2$-$C_{12}$ alkenyl, $C_2$-$C_{12}$ alkynyl, $C_4$-$C_{12}$ alkoxyalkenyl, $C_4$-$C_{12}$ alkoxyalkynyl, $C_1$-$C_{12}$ alkylthio or $C_2$-$C_{12}$ alkylthioalkyl;
$R^{b11}$ is methyl or —$Y^{b13}$—$R^{b12}$;
$R^{b12}$ is $C_1$-$C_2$ alkyl; and
$Y^{b13}$ is CH$_2$, O or S.

Examples of compounds of Formula b49.11 include (b49.11a) 2-[(3-bromo-6-quinolinyl)oxy]-N-(1,1-dimethyl-2-butyn-1-yl)-2-(methylthio)acetamide, (b49.11b) 2-[(3-ethynyl-6-quinolinyl)oxy]-N-[1-(hydroxymethyl)-1-methyl-2-propyn-1-yl]-2-(methylthio)-acetamide, (b49.11c) N-(1,1-dimethyl-2-butyn-1-yl)-2-[(3-ethynyl-6-quinolinyl)oxy]-2-(methylthio)acetamide, (b49.11d) 2-[(3-bromo-8-methyl-6-quinolinyl)oxy]-N-(1,1-dimethyl-2-propyn-1-yl)-2-(methylthio)acetamide and (b49.11e) 2-[(3-bromo-6-quinolinyl)oxy]-N-(1,1-dimethylethyl)butanamide.

Compounds of Formula b49.11, their use as fungicides and methods of preparation are generally known; see, for example, PCT Patent Publications WO 2004/047538, WO 2004/108663, WO 2006/058699, WO 2006/058700, WO 2008/110355, WO 2009/030469, WO 2009/049716 and WO 2009/087098.

Component 49.12 relates to N-[4-[[3-[(4-chlorophenyl)methyl]-1,2,4-thiadiazol-5-yl]oxy]-2,5-dimethylphenyl]-N-ethyl-N-methylmethanimidamide, which is believed to inhibit C24-methyl transferase involved in the biosynthesis of sterols.

Therefore of note is a mixture (i.e. composition) comprising a compound of Formula 1 and at least one fungicidal compound selected from the group consisting of the aforedescribed classes (1) through (49). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 and at least one fungicidal compound selected from the group of specific compounds listed above in connection with classes (1) through (49). Also of particular note is a composition comprising said mixture (in fungicidally effective amount) and further comprising at least one additional surfactant selected from the group consisting of surfactants, solid diluents and liquid diluents.

Examples of component (b) fungicides include acibenzolar-S-methyl, aldimorph, ametoctradin, amisulbrom, anilazine, azaconazole, azoxystrobin, benalaxyl (including benalaxyl-M), benodanil, benomyl, benthiavalicarb (including benthiavalicarb-isopropyl), benzovindiflupyr, bethoxazin, binapacryl, biphenyl, bitertanol, bixafen, blasticidin-S, boscalid, bromuconazole, bupirimate, buthiobate, captafol, captan, carbendazim, carboxin, carpropamid, chloroneb, chlorothalonil, chlozolinate, clotrimazole, copper hydroxide, copper oxychloride, copper sulfate, coumoxystrobin, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole (including diniconazole-M), dinocap, dithianon, dithiolanes, dodemorph, dodine, econazole, edifenphos, enoxastrobin (also known as enestroburin), epoxiconazole, etaconazole, ethaboxam, ethirimol, etridiazole, famoxadone, fenamidone, fenarimol, fenaminstrobin, fenbuconazole, fenfuram, fenhexamid, fenoxanil, fenpiclonil, fenpropidin, fenpropimorph, fenpyrazamine, fentin acetate, fentin chloride, fentin hydroxide, ferbam, ferimzone, flometoquin, fluazinam, fludioxonil, flufenoxystrobin, flumorph, fluopicolide, fluopyram, fluoroimide, fluoxastrobin, fluquinconazole, flusilazole, flusulfamide, flutianil, flutolanil, flutriafol, fluxapyroxad, folpet, fthalide, fuberidazole, furalaxyl, furametpyr, guazatine, hexaconazole, hymexazole, imazalil, imibenconazole, iminoctadine albesilate, iminoctadine triacetate, iodocarb, ipconazole, iprobenfos, iprodione, iprovalicarb, isoconazole, isofetamid, isoprothiolane, isopyrazam, isotianil, kasugamycin, kresoxim-methyl, mancozeb, mandepropamid, mandestrobin, maneb, mepanipyrim, mepronil, meptyldinocap, metalaxyl (including metalaxyl-M/mefenoxam), metconazole, methasulfocarb, metiram, metominostrobin, metrafenone, miconazole, myclobutanil, naftifine, neo-asozin, nuarimol, octhilinone, ofurace, orysastrobin, oxadixyl, oxathiapiprolin, oxolinic acid, oxpoconazole, oxycarboxin, oxytetracycline, pefurazoate, penconazole, pencycuron, penflufen, penthiopyrad, phosphorous acid (including salts thereof, e.g., fosetyl-aluminum), picarbutrazox, picoxystrobin, piperalin, polyoxin, probenazole, prochloraz, procymidone, propamacarb, propiconazole, propineb, proquinazid, prothiocarb, prothioconazole, pyraclostrobin, pyrametostrobin, pyraoxystrobin, pyrazophos, pyribencarb, pyributicarb, pyrifenox, pyrimethanil, pyriofenone, pyrisoxazole, pyroquilon, pyrrolnitrin, quinconazole, quinomethionate, quinoxyfen, quintozene, sedaxane, silthiofam, simeconazole, spiroxamine, streptomycin, sulfur, tebuconazole, tebufloquin, teclofthalam, tecnazene, terbinafine, tetraconazole, thiabendazole, thifluzamide, thiophanate, thiophanate-methyl, thiram, tiadinil, tolclofos-methyl, tolnifanide, tolprocarb, tolyfluanid, triadimefon, triadimenol, triarimol, triticonazole, triazoxide, tribasic copper sulfate, tricyclazole, triclopyricarb, tridemorph, trifloxystrobin, triflumizole, triforine, trimorphamide, uniconazole, uniconazole-P, validamycin, valifenalate (also known as valiphenal), vinclozolin, zineb, ziram, zoxamide, (3S,6S,7R,8R)-3-[[[3-[(acetyloxy)methoxy]-4-methoxy-2-pyridinyl] carbonyl]amino]-6-methyl-4,9-dioxo-8-(phenylmethyl)-1, 5-dioxonan-7-yl 2-methylpropanoate, (3S,6S,7R,8R)-3-[[[3-(acetyloxy)-4-methoxy-2-pyridinyl]carbonyl]amino]-6-methyl-4,9-dioxo-8-(phenylmethyl)-1,5-dioxonan-7-yl 2-methylpropanoate, N-[[3-(1,3-benzodioxol-5-yl-methoxy)-4-methoxy-2-pyridinyl]carbonyl]-O-[2,5-dideoxy-3-O-(2-methyl-1-oxopropyl)-2-(phenylmethyl)-L-arabinonoyl]-L-serine, (1→4)-lactone, N-[2-(1S,2R)-[1,1'-bicyclopropyl]-2-ylphenyl]-3-(difluoromethyl)-1-methyl-1H-pyrazole-4-carboxamide, 2-[(3-bromo-6-quinolinyl) oxy]-N-(1,1-dimethyl-2-butyn-1-yl)-2-(methylthio) acetamide, 2-[(3-bromo-6-quinolinyl)oxy]-N-(1,1-dimethylethyl)butanamide, 2-[(3-bromo-8-methyl-6-quinolinyl)oxy]-N-(1,1-dimethyl-2-propyn-1-yl)-2-(methylthio)acetamide, 2-butoxy-6-iodo-3-propyl-4H-1-benzopyran-4-one, 3-butyn-1-yl N-[6-[[[[(1-methyl-1H-tetrazol-5-yl)-phenylmethylene]amino]oxy]methyl]-2-pyridinyl]carbamate, α-(1-chlorocyclopropyl)-α-[2-(2,2-dichlorocyclopropyl)ethyl]-1H-1,2,4-triazole-1-ethanol, 2-[2-(1-chlorocyclopropyl)-4-(2,2-dichlorocyclopropyl)-2-hydroxybutyl]-1,2-dihydro-3H-1,2,4-triazole-3-thione, (αS)-[3-(4-chloro-2-fluorophenyl)-5-(2,4-difluorophenyl)-4-isoxazolyl]-3-pyridinemethanol, rel-1-[[(2R,3S)-3-(2-chlorophenyl)-2-(2,4-difluorophenyl)-2-oxiranyl]methyl]-1H-1,2,4-triazole, rel-2-[[(2R,3S)-3-(2-chlorophenyl)-2-(2,4-difluorophenyl)-2-oxiranyl]methyl]-1,2-dihydro-3H-1,2,4-triazole-3-thione, rel-1-[[(2R,3S)-3-(2-chlorophenyl)-2-(2,4-difluorophenyl)-2-oxiranyl]methyl]-5-(2-propen-1-ylthio)-1H-1,2,4-triazole, 3-[5-(4-chlorophenyl)-2,3-dimethyl-3-isoxazolidinyl]pyridine, (2-chloro-6-fluorophenyl)methyl 2-[1-[2-[3,5-bis(difluoromethyl)-1H-pyrazol-1-yl]acetyl]-4-piperidinyl]-4-thiazolecarboxylate, N-[4-[[3-[(4-chlorophenyl)methyl]-1,2,4-thiadiazol-5-yl] oxy]-2,5-dimethylphenyl]-N-ethyl-N-methyl-methanimidamide, N-[2-[4-[[3-(4-chlorophenyl)-2-propyn-1-yl]oxy]-3-methoxyphenyl]-ethyl]-3-methyl-2-[(methylsulfonyl) amino]butanamide, N-[2-[4-[[3-(4-chlorophenyl)-2-propyn-1-yl]oxy]-3-methoxyphenyl]ethyl]-3-methyl-2-[(ethylsulfonyl)amino]butanamide, N-[4-[4-chloro-3-(trifluoromethyl)phenoxy]-2,5-dimethylphenyl]-N-ethyl-N-methyl-methanimidamide, N-cyclopropyl-3-(difluoromethyl)-5-fluoro-1-methyl-N-[[2-(1-methyl-ethyl) phenyl]methyl]-1H-pyrazole-4-carboxamide, N-[[(cyclopropylmethoxy)amino][6-(difluoromethoxy)-2,3-difluorophenyl]methylene]benzeneacetamide, N-[2-(2,4-dichlorophenyl)-2-methoxy-1-methylethyl]-3-(difluoromethyl)-1-methyl-1H-pyrazole-4-carboxamide, N-(3',4'-difluoro[1,1'-biphenyl]-2-yl)-3-(trifluoromethyl)-2-pyrazinecarboxamide, 3-(difluoromethyl)-N-(2,3-dihydro-1,1,3-trimethyl-1H-inden-4-yl)-1-methyl-1H-pyrazole-4-carboxamide, 3-(difluoromethyl)-N-[4-fluoro-2-(1,1,2,3,3,3-hexa-fluoropropoxy)phenyl]-1-methyl-1H-pyrazole-4-carboxamide, 5,8-difluoro-N-[2-[3-methoxy-4-[[4-(trifluoromethyl)-2-pyridinyl]oxy]phenyl]ethyl]-4-quinazolinamine, 3-(difluoromethyl)-1-methyl-N-[2-(1,1,2,2-tetrafluoroethoxy)phenyl]-1H-pyrazole-4-carboxamide, 1-[4-[4-[5R-[(2,6-difluorophenoxy)methyl]-4,5-dihydro-3-isoxazolyl]-2-thiazolyl]-1-piperidinyl]-2-[5-methyl-3-(trifluoromethyl)-1H-pyrazol-1-yl]ethanone, N-(1,1-dimethyl-2-butyn-1-yl)-2-[(3-ethynyl-6-quinolinyl)oxy]-2-(methylthio)acetamide, 2,6-dimethyl-1H,5H-[1,4]dithiino [2,3-c:5,6-c']dipyrrole-1,3,5,7(2H,6H)-tetrone, 2-[(3-ethynyl-6-quinolinyl)oxy]-N-[1-(hydroxymethyl)-1-methyl-2-propyn-1-yl]-2-(methylthio)acetamide, 4-fluorophenyl N-[1-[[[1-(4-cyanophenyl)ethyl]sulfonyl] methyl]propyl]carbamate, 5-fluoro-2-[(4-fluorophenyl) methoxy]-4-pyrimidinamine, 5-fluoro-2-[(4-methylphenyl) methoxy]-4-pyrimidinamine, (3S,6S,7R,8R)-3-[[[4-methoxy-3-[[(2-methylpropoxy)carbonyl]oxy]-2-pyridinyl] carbonyl]amino]-6-methyl-4,9-dioxo-8-(phenylmethyl)-1, 5-dioxonan-7-yl 2-methylpropanoate, α-(methoxyimino)-N-methyl-2-[[[1-[3-(trifluoro-methyl)phenyl]ethoxy]imino] methyl]benzeneacetamide, [[4-methoxy-2-[[[(3S,7R,8R, 9S)-9-methyl-8-(2-methyl-1-oxopropoxy)-2,6-dioxo-7-(phenylmethyl)-1,5-dioxonan-3-yl]-amino]carbonyl]-3-pyridinyl]oxy]methyl 2-methylpropanoate, pentyl N-[6-[[[[(1-methyl-1H-tetrazol-5-yl)phenylmethylene]amino] oxy]methyl]-2-pyridinyl]carbamate, pentyl N-[4-[[[[(1-methyl-1H-tetrazol-5-yl)phenylmethylene]amino]oxy] methyl]-2-thiazolyl]carbamate, and pentyl N-[6-[[[[(Z)-(1-methyl-1H-tetrazol-5-yl)phenylmethylene]amino]oxy] methyl]-2-pyridinyl]carbamate and (1R)-1,2,3,4-tetrahydro-1-naphthalenyl 2-[1-[2-[3,5-bis(difluoromethyl)-1H-pyrazol-1-yl]acetyl]-4-piperidinyl]-4-thiazolecarboxylate. Therefore of note is a fungicidal composition comprising as component (a) a compound of Formula 1 (or an N-oxide or salt thereof) and as component (b) at least one fungicide selected from the preceding list.

Of particular note are combinations of compounds of Formula 1 (or an N-oxide or salt thereof) (i.e. Component (a) in compositions) with azoxystrobin, benzovindiflupyr, bixafen, captan, carpropamid, chlorothalonil, copper hydroxide, copper oxychloride, copper sulfate, cymoxanil, cyproconazole, cyprodinil, diethofencarb, difenoconazole, dimethomorph, epoxiconazole, ethaboxam, fenarimol, fenhexamid, fluazinam, fludioxonil, fluopyram, flusilazole, flutianil, flutriafol, fluxapyroxad, folpet, iprodione, isofetamid, isopyrazam, kresoxim-methyl, mancozeb, mandestrobin, meptyldinocap, metalaxyl (including metalaxyl-M/mefenoxam), metconazole, metrafenone, myclobutanil, oxathiapiprolin, penflufen, penthiopyrad, phosphorous acid (including salts thereof, e.g., fosetyl-aluminum), picoxystrobin, propiconazole, proquinazid, prothioconazole, pyraclostrobin, pyrimethanil, sedaxane spiroxamine, sulfur, tebuconazole, thiophanate-methyl, trifloxystrobin, zoxamide, α-(1-chlorocyclopropyl)-α-[2-(2,2-dichlorocyclopropyl)ethyl]-1H-1,2,4-triazole-1-ethanol, 2-[2-(1 chlorocyclopropyl)-4-(2,2-dichlorocyclopropyl)-2-hydroxybutyl]-1,2-dihydro-3H-1,2,4-triazole-3-thione, N-[2-(2,4-dichlorophenyl)-2-methoxy-1-methylethyl]-3-(difluoromethyl)-1-methyl-1H-pyrazole-4-carboxamide, 3-(difluoromethyl)-N-(2,3-dihydro-1,1,3-trimethyl-1H-inden-4-yl)-1-methyl-1H-pyrazole-4-carboxamide, 1-[4-[4-[5R-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, 1,1-dimethylethyl N-[6-[[[[(1-methyl-1H-tetrazol-5-yl)phenylmethylene]amino]oxy] methyl]-2-pyridinyl]carbamate, 2,6-dimethyl-1H,5H-[1,4] dithiino[2,3-c:5,6-c']dipyrrole-1,3,5,7(2H,6H)-tetrone, 5-fluoro-2-[(4-fluoro-phenyl)methoxy]-4-pyrimidinamine, 5-fluoro-2-[(4-methylphenyl)methoxy]-4-pyrimidin-amine, (αS)-[3-(4-chloro-2-fluorophenyl)-5-(2,4-difluorophenyl)-4-isoxazolyl]-3-pyridinemethanol, rel-1-[[(2R,3S)-3-(2-chlorophenyl)-2-(2,4-difluorophenyl)-2-oxiranyl]-methyl]-1H-1,2,4-triazole, rel-2-[[(2R,3S)-3-(2-chlorophenyl)-2-(2,4-difluorophenyl)-2-oxiranyl]methyl]-1,2-dihydro-3H-1,2,4-triazole-3-thione, and rel-1-[[(2R,3S)-3-(2-chlorophenyl)-2-(2,4-difluorophenyl)-2-oxiranyl]methyl]-5-(2-propen-1-ylthio)-1H-1,2,4-triazole (i.e. as Component (b) in compositions).

Examples of other biologically active compounds or agents with which compounds of this invention can be formulated are: invertebrate pest control compounds or agents such as abamectin, acephate, acetamiprid, acrinathrin, afidopyropen ([(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11H-naphtho[2,1-b]pyrano[3,4-e]pyran-4-yl] methyl cyclopropanecarboxylate), amidoflumet (S-1955), avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyclaniliprole (3-bromo-N-[2-bromo-4-chloro-6-[[(1-cyclopropylethyl)amino]carbonyl]phenyl]-1-(3-chloro-2-pyridinyl)-1H-pyrazole-5-carboxamide), cycloxaprid ((5S,8R)-1-[(6-chloro-3-pyridinyl)methyl]-2,3,5,6,7,8-hexahydro-9-nitro-5,8-epoxy-1H-imidazo[1,2-a]azepine), cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, flufenoxystrobin (methyl(αE)-2-[[2-chloro-4-(trifluoromethyl)phenoxy]methyl]-α-(methoxymethylene)benzeneacetate), flufensulfone (5-chloro-2-[(3,4,4-trifluoro-3-buten-1-yl)sulfonyl]thiazole), flupiprole (1-[2,6-dichloro-4-(trifluoromethyl)phenyl]-5-[(2-methyl-2-propen-1-yl)amino]-4-[(trifluoromethyl) sulfinyl]-1H-pyrazole-3-carbonitrile), flupyradifurone (4-[[[(6-chloro-3-pyridinyl)methyl](2,2-difluoroethyl)amino]-2 (5H)-furanone), tau-fluvalinate, flufenerim (UR-50701), flufenoxuron, fonophos, halofenozide, heptafluthrin ([2,3,5, 6-tetrafluoro-4-(methoxymethyl)phenyl]methyl 2,2-dimethyl-3-[(1Z)-3,3,3-trifluoro-1-propen-1-yl]cyclopropanecarboxylate), hexaflumuron, hydramethylnon, imidacloprid, indoxacarb, isofenphos, lufenuron, malathion, meperfluthrin ([2,3,5,6-tetrafluoro-4-(methoxymethyl)phenyl]methyl(1R,3S)-3-(2,2-dichloroethenyl)-2,2-dimethylcyclopropanecarboxylate), metaflumizone, metaldehyde, methamidophos, methidathion, methomyl, methoprene, methoxychlor, methoxyfenozide, metofluthrin, milbemycin oxime, momfluorothrin ([2,3,5,6-tetrafluoro-4-(methoxymethyl)phenyl]methyl 3-(2-cyano-1-propen-1-yl)-2,2-dimethylcyclopropanecarboxylate), monocrotophos, nicotine, nitenpyram, nithiazine, novaluron, noviflumuron (XDE-007), oxamyl, pyflubumide (1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide), parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriminostrobin (methyl (αE)-2-[[[2-[(2,4-dichlorophenyl)amino]-6-(trifluoromethyl)-4-pyrimidinyl]oxy]methyl]-α-(methoxymethylene) benzeneacetate), pyriprole, pyriproxyfen, rotenone, ryanodine, spinetoram, spinosad, spirodiclofen, spiromesifen (BSN 2060), spirotetramat, sulfoxaflor, sulprofos, tebufenozide, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon and triflumuron; and biological agents including entomopathogenic bacteria, such as *Bacillus thuringiensis* subsp. *aizawai, Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U. K., 2003 and *The BioPesticide Manual, 2nd Edition*, L. G. Copping, Ed., British Crop Protection Council, Farnham, Surrey, U. K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Also in certain instances, combinations of a compound of the invention with other biologically active compounds or agents can result in a less-than-additive (i.e. safening) effect on organisms beneficial to the agronomic environment. For example, a compound of the invention may safen a herbicide on crop plants or protect a beneficial insect species (e.g., insect predators, pollinators such as bees) from an insecticide.

Fungicides of note for formulation with compounds of Formula 1 to provide mixtures useful in seed treatment include but are not limited to amisulbrom, azoxystrobin, boscalid, carbendazim, carboxin, cymoxanil, cyproconazole, difenoconazole, dimethomorph, fluazinam, fludioxonil, flufenoxystrobin, fluquinconazole, fluopicolide, fluoxastrobin, flutriafol, fluxapyroxad, ipconazole, iprodione, metalaxyl, mefenoxam, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Invertebrate pest control compounds or agents with which compounds of Formula 1 can be formulated to provide mixtures useful in seed treatment include but are not limited to abamectin, acetamiprid, acrinathrin, afidopyropen, amitraz, avermectin, azadirachtin, bensultap, bifenthrin, buprofezin, cadusafos, carbaryl, carbofuran, cartap, chlorantraniliprole, chlorfenapyr, chlorpyrifos, clothianidin, cyantraniliprole, cyclaniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, fluensulfone, flufenoxuron, flufiprole, flupyradifurone, fluvalinate, formetanate, fosthiazate, heptafluthrin, hexaflumuron, hydramethylnon, imidacloprid, indoxacarb, lufenuron, meperfluthrin, metaflumizone, methiocarb, methomyl, methoprene, methoxyfenozide, momfluorothrin, nitenpyram, nithiazine, novaluron, oxamyl, pyflubumide, pymetrozine, pyrethrin, pyridaben, pyriminostrobin, pyridalyl, pyriproxyfen, ryanodine, spinetoram, spinosad, spirodiclofen, spiromesifen, spirotetramat, sulfoxaflor, tebufenozide, tetramethrin, tetramethylfluthrin, thiacloprid, thiamethoxam, thiodicarb, thiosultap-sodium, tralomethrin, triazamate, triflumuron, *Bacillus thuringiensis* delta-endotoxins, strains of *Bacillus thuringiensis* and strains of *Nucleo polyhydrosis* viruses.

Compositions comprising compounds of Formula 1 useful for seed treatment can further comprise bacteria and fungi that have the ability to provide protection from the harmful effects of plant pathogenic fungi or bacteria and/or soil born animals such as nematodes. Bacteria exhibiting nematicidal properties may include but are not limited to *Bacillus firmus, Bacillus cereus, Bacillius subtiliis* and *Pasteuria penetrans*. A suitable *Bacillus firmus* strain is strain CNCM 1-1582 (GB-126) which is commercially available as BioNem™. A suitable *Bacillus cereus* strain is strain NCMM 1-1592. Both *Bacillus* strains are disclosed in U.S. Pat. No. 6,406,690. Other suitable bacteria exhibiting nematicidal activity are *B. amyloliquefaciens* IN937a and *B. subtilis* strain GB03. Bacteria exhibiting fungicidal properties may include but are not limited to *B. pumilus* strain GB34. Fungal species exhibiting nematicidal properties may include but are not limited to *Myrothecium verrucaria, Paecilomyces lilacinus* and *Purpureocillium lilacinum*.

Seed treatments can also include one or more nematicidal agents of natural origin such as the elicitor protein called harpin which is isolated from certain bacterial plant pathogens such as *Erwinia amylovora*. An example is the Harpin-N-Tek seed treatment technology available as N-Hibit™ Gold CST.

Seed treatments can also include one or more species of legume-root nodulating bacteria such as the microsymbiotic nitrogen-fixing bacteria *Bradyrhizobium japonicum*. These inoculants can optionally include one or more lipo-chitooligosaccharides (LCOs), which are nodulation (Nod) factors produced by rhizobia bacteria during the initiation of nodule formation on the roots of legumes. For example, the Optimize® brand seed treatment technology incorporates LCO Promoter Technology™ in combination with an inocculant.

Seed treatments can also include one or more isoflavones which can increase the level of root colonization by mycorrhizal fungi. Mycorrhizal fungi improve plant growth by enhancing the root uptake of nutrients such as water, sulfates, nitrates, phosphates and metals. Examples of isoflavones include, but are not limited to, genistein, biochanin A, formononetin, daidzein, glycitein, hesperetin, naringenin and pratensein. Formononetin is available as an active ingredient in mycorrhizal inocculant products such as PHC Colonize® AG.

Seed treatments can also include one or more plant activators that induce systemic acquired resistance in plants following contact by a pathogen. An example of a plant activator which induces such protective mechanisms is acibenzolar-S-methyl.

The following Tests demonstrate the control efficacy of compounds of this invention on specific pathogens. The pathogen control protection afforded by the compounds is not limited, however, to these species. See Index Tables A-C for compound descriptions. The following abbreviations are used in the Index Tables which follow: Me is methyl, Et is ethyl, Ph is phenyl and OMe is methoxy. The abbreviation "Ex." stands for "Example" and is followed by a number indicating in which example the compound is prepared. In the following Index Tables each value of G refers to the G ring as described in the Summary of the Invention. When an $(R^2)_n$ substituent is present, it is noted immediately after the value of the G ring. In the absence of an $(R^2)_n$ substituent, this means that n is 0, and hydrogen atoms instead of $R^2$ substituents are bonded to all available G ring carbon atoms. In the following Index Tables each value of A refers to the A rings as described in Exhibit A. Mass spectra are reported as the molecular weight of the highest isotopic abundance parent ion (M+1) formed by addition of $H^+$ (molecular weight of 1) to the molecule, or (M−1) formed by the loss of $H^+$ (molecular weight of 1) from the molecule, observed by using an liquid chromatography coupled to a mass spectrometer (MS) using either atmospheric pressure chemical ionization ($AP^+$) or electrospray ionization ($ESI^+$), where "amu" stands for atomic mass units.

INDEX TABLE A

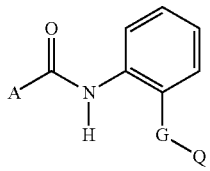

| Cmpd. No. | A | G, (R²)ₙ | Q | M.P. | M + 1 | M − 1 |
|---|---|---|---|---|---|---|
| 1 | A-1a | G-2 | 3-CF₃-1H-pyrazol-1-yl | 180-182 | | |
| 2 | A-2b | G-2 | 3-CF₃-1H-pyrazol-1-yl | 207-209 | | |
| 3 (Ex. 3) | A-1d | G-2 | 3-CF₃-1H-pyrazol-1-yl | 207-209* | | |
| 4 | A-2b | G-1 | 4-(3,5-di-F—Ph)-1H-pyrazol-1-yl | | 507 | |
| 5 | A-2b | G-1 | 4-(3-F—Ph)-1H-pyrazol-1-yl | | 488 | |
| 6 | A-1d | G-1 | 5-(4-F—Ph)-isoxazolidin-3-yl | | 507 | |
| 7 | A-2b | G-1 | 4-(2-F—Ph)-1H-pyrazol-1-yl | | 489 | |
| 8 | A-2b | G-1 | 4-(2-OMe—Ph)-1H-pyrazol-1-yl | | 501 | |
| 9 | A-2b | G-1 | 4-(3-OMe—Ph)-1H-pyrazol-1-yl | | 501 | |
| 10 | A-2b | G-1 | 4-(3,5-di-OMe—Ph)-1H-pyrazol-1-yl | | | 529 |
| 11 | A-2b | G-1 | 3-Br-1H-pyrazol-1-yl | | 475 | |
| 12 | A-1d | G-1 | 1H-pyrazol-1-yl | | 410 | |
| 13 | A-1d | G-1 | 3-Br-1H-pyrazol-1-yl | | 489 | |
| 14 | A-1d | G-1 | 4-Br-1H-pyrazol-1-yl | | 489 | |
| 15 | A-2b | G-1 | 1H-pyrazol-1-yl | | | 393 |
| 16 | A-1d | G-1 | 4-(3-OMe—Ph)-1H-pyrazol-1-yl | | 516 | |
| 17 | A-1d | G-1 | 5-(3-F—Ph)-isoxazolidin-3-yl | | 507 | |
| 18 | A-1d | G-1 | 5-(3-OMe—Ph)-isoxazolidin-3-yl | | 519 | |
| 19 | A-1d | G-1 | 5-(3,5-di-F—Ph)-isoxazolidin-3-yl | | 525 | |
| 20 | A-1d | G-1 | 5-(3,5-di-OMe—Ph)-isoxazolidin-3-yl | | 549 | |
| 21 | A-2b | G-1 | 5-Me-thiophen-2-yl | | | 423 |
| 22 | A-2b | G-1 | 5-Me-furan-2-yl | | 409 | |
| 23 | A-1b | G-1 | 3-CF₃-1H-pyrazol-1-yl | 172-174 | | |
| 24 | A-1h | G-1 | 3-CF₃-1H-pyrazol-1-yl | 142-144 | | |
| 25 | A-1f | G-1 | 3-CF₃-1H-pyrazol-1-yl | 141-143 | | |
| 26 | A-1d | G-1 | 3-CF₃-1H-pyrazol-1-yl | 157-159 | | |
| 27 | A-1d | G-1 | 4-(3-F—Ph)-1H-pyrazol-1-yl | | 504 | |
| 28 | A-1d | G-1 | 4-(3,5-di-F—Ph)-1H-pyrazol-1-yl | | 522 | |
| 29 | A-1d | G-1 | 4-(2-F—Ph)-1H-pyrazol-1-yl | | 504 | |
| 30 | A-1d | G-1 | 4-(4-F—Ph)-1H-pyrazol-1-yl | | 504 | |
| 31 | A-2b | G-1 | 4-Br-1H-pyrazol-1-yl | | 475 | |
| 32 | A-1d | G-1 | 4-Cl-1H-pyrazol-1-yl | | 444 | |
| 33 | A-1a | G-1, 5-Cl | 3-CF₃-1H-pyrazol-1-yl | | 511 | |
| 34 | A-1d | G-1, 5-Cl | 3-CF₃-1H-pyrazol-1-yl | | 512 | |
| 35 | A-2b | G-1, 5-Cl | 3-CF₃-1H-pyrazol-1-yl | | 497 | |
| 36 | A-1a | G-1, 5-CH₃ | 3-CF₃-1H-pyrazol-1-yl | | 491 | |
| 37 | A-1d | G-1, 5-CH₃ | 3-CF₃-1H-pyrazol-1-yl | | 492 | |
| 38 | A-2b | G-1, 5-CH₃ | 3-CF₃-1H-pyrazol-1-yl | | 477 | |
| 39 | A-1d | G-1 | 3-Ph-1H-pyrazol-1-yl | | | 484 |
| 40 | A-2b | G-1 | 4-Cl-1H-pyrazol-1-yl | | | 427 |
| 41 | A-2b | G-1 | 3-Ph-1H-pyrazol-1-yl | | 471 | |
| 42 | A-1a | G-1 | 3-Ph-1H-pyrazol-1-yl | | | 483 |
| 43 | A-1a | G-1 | 4-Me-1H-pyrazol-1-yl | | | 422 |
| 44 | A-1a | G-1 | 4-Me-1H-pyrazol-1-yl | | | 421 |
| 45 | A-2b | G-1 | 4-Me-1H-pyrazol-1-yl | | | 407 |
| 46 | A-1b | G-1 | 4-Me-1H-pyrazol-1-yl | | 391 | |
| 47 | A-1b | G-1 | 4-Br-1H-pyrazol-1-yl | | 455 | |
| 48 | A-1d | G-1 | 3-CF₃-5-OMe-1H-pyrazol-1-yl | | 508 | |
| 49 | A-1a | G-1, 5-F | 3-CF₃-1H-pyrazol-1-yl | 116-118 | 496 | |
| 50 | A-1d | G-1, 5-F | 3-CF₃-1H-pyrazol-1-yl | 169-170 | 497 | |
| 51 | A-2b | G-1 | 3-CF₃-1H-pyrazol-1-yl | 157-159 | | |
| 52 | A-1d | G-1 | 3,5-di-Me-1H-pyrazol-1-yl | | | 436 |
| 53 | A-1b | G-1 | 3-Ph-1H-pyrazol-1-yl | | 453 | |
| 54 | A-2b | G-3 | 3-CF₃-1H-pyrazol-1-yl | 248-250 | | |
| 55 | A-1f | G-4 | 3-CF₃-1H-pyrazol-1-yl | 178-180 | | |
| 56 | A-1d | G-4 | 3-CF₃-1H-pyrazol-1-yl | 178-180 | | |
| 57 | A-1a | G-3 | 3-CF₃-1H-pyrazol-1-yl | 175-177 | | |
| 58 | A-2b | G-4 | 3-CF₃-1H-pyrazol-1-yl | 167-169 | | |
| 59 (Ex. 4) | A-1d | G-3 | 3-CF₃-1H-pyrazol-1-yl | 197-199* | | |
| 60 | A-1a | G-1, 5-Cl | 4-Cl-1H-pyrazol-1-yl | | 477 | |
| 61 | A-1d | G-1, 5-Cl | 4-Cl-1H-pyrazol-1-yl | | 478 | |
| 62 | A-2b | G-1, 5-Cl | 4-Cl-1H-pyrazol-1-yl | | 463 | |
| 63 | A-1a | G-1, 5-CH₃ | 4-Cl-1H-pyrazol-1-yl | | 457 | |
| 64 | A-1d | G-1, 5-CH₃ | 4-Cl-1H-pyrazol-1-yl | | 458 | |
| 65 | A-2b | G-1, 5-CH₃ | 4-Cl-1H-pyrazol-1-yl | | 443 | |

INDEX TABLE A-continued

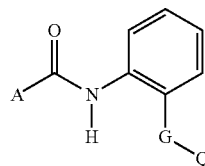

| Cmpd. No. | A | G, (R$^2$)$_n$ | Q | M.P. | M + 1 | M − 1 |
|---|---|---|---|---|---|---|
| 66 | A-1a | G-1 | 4-Cl-1H-pyrazol-1-yl | | 444 | |
| 67 | A-1b | G-1 | 4-Cl-1H-pyrazol-1-yl | | 411 | |
| 68 (Ex. 2) | A-2b | G-1, 5-F | 3-CF$_3$-1H-pyrazol-1-yl | 205-210* | 481 | 479 |
| 69 | A-1d | G-1, 5-F | 3-Cl-1H-pyrazol-1-yl | | 462 | |
| 70 | A-1d | G-1, 5-F | 4-Cl-1H-pyrazol-1-yl | | 462 | |
| 71 | A-1d | G-1, 5-F | 3-Br-1H-pyrazol-1-yl | | 508 | |
| 72 | A-1d | G-1, 5-F | 3-Ph-1H-pyrazol-1-yl | | | 503 |
| 73 | A-2b | G-1, 5-F | 3-Cl-1H-pyrazol-1-yl | | 447 | |
| 74 | A-2b | G-1, 5-F | 4-Cl-1H-pyrazol-1-yl | | 447 | |
| 75 | A-2b | G-1, 5-F | 3-Br-1H-pyrazol-1-yl | | 493 | |
| 76 | A-2b | G-1, 5-F | 3-Ph-1H-pyrazol-1-yl | | 489 | |
| 77 | A-1a | G-1, 5-F | 3-Cl-1H-pyrazol-1-yl | | 461 | |
| 78 | A-1a | G-1, 5-F | 4-Cl-1H-pyrazol-1-yl | | 461 | |
| 79 | A-1a | G-1, 5-F | 3-Br-1H-pyrazol-1-yl | | | 505 |
| 80 | A-1a | G-1, 5-F | 3-Ph-1H-pyrazol-1-yl | | 504 | |
| 81 | A-1d | G-1, 5-F | 3-CH$_3$-1H-indol-1-yl | | 441 | |
| 82 | A-1d | G-1 | 5-OH-3-CF$_3$-1H-pyrazol-1-yl | | 494 | |
| 85 | A-1d | G-1, 5-F | 4-CN-1H-pyrazol-1-yl | | 453 | 451 |
| 86 | A-1d | G-1, 5-F | 3-CN-1H-pyrazol-1-yl | | 453 | 451 |
| 87 | A-2b | G-1 | 3-(3-F—Ph)-1H-pyrazol-1-yl | | 489 | |
| 88 | A-2b | G-1 | 3-(4-OMe—Ph)-1H-pyrazol-1-yl | | 501 | |
| 89 | A-2b | G-1 | 3-(3,5-di-F—Ph)-1H-pyrazol-1-yl | | 507 | |
| 90 | A-2b | G-1 | 3-(2-F—Ph)-1H-pyrazol-1-yl | | 489 | |
| 91 | A-2b | G-1 | 3-(3,5-di-OMe—Ph)-1H-pyrazol-1-yl | | 531 | |
| 92 | A-3c | G-1 | 3-CF$_3$-1H-pyrazol-1-yl | | | 496 |
| 93 | A-4a | G-1 | 3-CF$_3$-1H-pyrazol-1-yl | | | 427 |
| 94 | A-2a | G-1 | 3-CF$_3$-1H-pyrazol-1-yl | | | 479 |
| 95 | A-4a | G-1, 5-Cl | 3-CF$_3$-1H-pyrazol-1-yl | | 463 | |
| 96 | A-1f | G-1, 5-Cl | 3-CF$_3$-1H-pyrazol-1-yl | | 480 | |
| 97 | A-2a | G-1, 5-Cl | 3-CF$_3$-1H-pyrazol-1-yl | | 515 | |
| 98 | A-2b | G-1 | 3-(2-OMe—Ph)-1H-pyrazol-1-yl | | 501 | |
| 99 | A-2b | G-1 | 3-(4-F—Ph)-1H-pyrazol-1-yl | | 489 | |
| 100 | A-2b | G-1 | 3-(2,4-di-OMe—Ph)-1H-pyrazol-1-yl | | 531 | |
| 101 | A-2b | G-1 | 3-(2,4-di-F—Ph)-1H-pyrazol-1-yl | | 507 | |
| 102 | A-2b | G-1 | 5-(3-OMe—Ph)-isoxazolidin-3-yl | | 504 | |
| 103 | A-8d | G-1, 5-Cl | 3-CF$_3$-1H-pyrazol-1-yl | | | 575 |
| 104 | A-1j | G-1, 5-Cl | 3-CF$_3$-1H-pyrazol-1-yl | | 479 | 477 |
| 105 | A-1d | G-1, 5-CN | 3-CF$_3$-1H-pyrazol-1-yl | | 503 | |
| 106 | A-2b | G-1, 5-CN | 3-CF$_3$-1H-pyrazol-1-yl | | 488 | |
| 107 | A-3c | G-1, 5-CN | 3-CF$_3$-1H-pyrazol-1-yl | | 523 | |
| 108 | A-1f | G-1, 5-CN | 3-CF$_3$-1H-pyrazol-1-yl | | 470 | |
| 109 | A-2b | G-1 | 5-Me-5-COOEt-isoxazolidin-3-yl | | 484 | |
| 110 | A-2b | G-1 | 5-COOEt-isoxazolidin-3-yl | | 470 | |
| 111 | A-4e | G-1, 5-Cl | 3-CF$_3$-1H-pyrazol-1-yl | | 450 | 448 |
| 112 | A-7b | G-1, 5-Cl | 3-CF$_3$-1H-pyrazol-1-yl | | 450 | 448 |
| 113 | A-6a | G-1, 5-F | 3-CF$_3$-1H-pyrazol-1-yl | 130-133 | | |
| 114 | A-6b | G-1, 5-F | 3-CF$_3$-1H-pyrazol-1-yl | 177-181 | | |
| 115 | A-1h | G-1, 5-F | 3-CF$_3$-1H-pyrazol-1-yl | 164-168 | | |
| 116 | A-4f | G-1, 5-Cl | 3-CF$_3$-1H-pyrazol-1-yl | | 478 | 476 |
| 117 | A-9a | G-1, 5-Cl | 3-CF$_3$-1H-pyrazol-1-yl | | 514 | 512 |
| 118 | A-5a | G-1, 5-Cl | 3-CF$_3$-1H-pyrazol-1-yl | | 448 | 446 |
| 119 | A-8e | G-5 | 3-CF$_3$-1H-pyrazol-1-yl | 227-231 | | |
| 120 | A-7c | G-1, 5-Cl | 3-CF$_3$-1H-pyrazol-1-yl | | 484 | 482 |
| 121 | A-1k | G-1, 5-Cl | 3-CF$_3$-1H-pyrazol-1-yl | | 525 | 523 |
| 122 | A-1g | G-1, 5-Cl | 3-CF$_3$-1H-pyrazol-1-yl | | 526 | 524 |
| 123 | A-1u | G-1, 5-Cl | 3-CF$_3$-1H-pyrazol-1-yl | | 572 | 570 |
| 124 | A-1v | G-1, 5-Cl | 3-CF$_3$-1H-pyrazol-1-yl | | 570 | 568 |
| 125 | A-1c | G-1, 5-Cl | 3-CF$_3$-1H-pyrazol-1-yl | | 524 | 522 |
| 126 | A-8a | G-1, 5-F | 3-CF$_3$-1H-pyrazol-1-yl | 139-143 | | |
| 127 | A-2a | G-1, 5-CN | 3-CF$_3$-1H-pyrazol-1-yl | | 506 | |
| 128 | A-10a | G-1, 5-Cl | 3-CF$_3$-1H-pyrazol-1-yl | | 449 | 447 |
| 129 | A-11a | G-1, 5-Cl | 3-CF$_3$-1H-pyrazol-1-yl | | 449 | 447 |
| 130 | A-1d | G-1 | 4,5-dihydro-1-Me-5-(3-OMe—Ph)-1H-pyrazol-3-yl | | 532 | |
| 131 | A-3c | G-1, 5-Cl | 3-CF$_3$-1H-pyrazol-1-yl | | 532 | |
| 132 | A-1w | G-1, 5-Cl | 3-CF$_3$-1H-pyrazol-1-yl | | 493 | |
| 133 | A-2a | G-1, 5-CH$_3$ | 3-CF$_3$-1H-pyrazol-1-yl | | 495 | |
| 134 | A-4a | G-1, 5-CH$_3$ | 3-CF$_3$-1H-pyrazol-1-yl | | 443 | |
| 135 | A-1f | G-1, 5-CH$_3$ | 3-CF$_3$-1H-pyrazol-1-yl | | 459 | |

INDEX TABLE A-continued

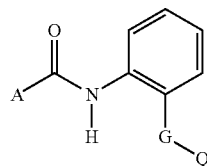

| Cmpd. No. | A | G, (R²)ₙ | Q | M.P. | M + 1 | M − 1 |
|---|---|---|---|---|---|---|
| 136 | A-3c | G-1, 5-CH₃ | 3-CF₃-1H-pyrazol-1-yl | | 512 | |
| 137 | A-7a | G-1, 5-CH₃ | 3-CF₃-1H-pyrazol-1-yl | | 443 | |
| 138 | A-7a | G-1, 5-Cl | 3-CF₃-1H-pyrazol-1-yl | | 463 | |
| 139 | A-7d | G-1, 5-Cl | 3-CF₃-1H-pyrazol-1-yl | | 530 | 528 |
| 140 | A-7e | G-1, 5-Cl | 3-CF₃-1H-pyrazol-1-yl | | 576 | 574 |
| 141 | A-4g | G-1, 5-Cl | 3-CF₃-1H-pyrazol-1-yl | | 496 | 494 |
| 142 | A-7f | G-1, 5-Cl | 3-CF₃-1H-pyrazol-1-yl | | 496 | 494 |
| 143 | A-4h | G-1, 5-CN | 3-CF₃-1H-pyrazol-1-yl | | 566 | |
| 144 | A-1d | G-1 | 5-Me-5-COOEt-isoxazolidin-3-yl | | 499 | |
| 145 | A-1d | G-1 | 5-COOEt-isoxazolidin-3-yl | | 485 | |
| 146 | A-1d | G-1 | 5-Me-5-COOH-isoxazolidin-3-yl | | 471 | |
| 147 | A-2f | G-1, 5-F | 3-CF₃-1H-pyrazol-1-yl | | 499 | |
| 148 | A-2f | G-1, 5-Cl | 3-CF₃-1H-pyrazol-1-yl | | 515 | |
| 149 | A-1f | G-1, 5-F | 3-CF₃-1H-pyrazol-1-yl | 165-168 | | |
| 150 | A-2a | G-1, 5-F | 3-CF₃-1H-pyrazol-1-yl | 154-157 | | |
| 151 | A-3c | G-1, 5-F | 3-CF₃-1H-pyrazol-1-yl | 176-179 | | |
| 152 | A-4a | G-1, 5-F | 3-CF₃-1H-pyrazol-1-yl | 151-154 | | |
| 153 | A-2b | G-1, 5-F | 4-CF₃-1H-imidazol-1-yl | | 481 | |
| 154 | A-4a | G-1, 5-CN | 3-CF₃-1H-pyrazol-1-yl | | 454 | |
| 155 | A-8f | G-1, 5-Cl | 3-CF₃-1H-pyrazol-1-yl | | 544 | 542 |
| 156 | A-8g | G-1, 5-Cl | 3-CF₃-1H-pyrazol-1-yl | | 591 | |
| 157 | A-1p | G-1, 5-Cl | 3-CF₃-1H-pyrazol-1-yl | | 524 | 522 |
| 158 | A-1n | G-1, 5-Cl | 3-CF₃-1H-pyrazol-1-yl | | 570 | 568 |
| 159 | A-4h | G-1, 5-F | 3-CF₃-1H-pyrazol-1-yl | | 560 | 558 |
| 160 | A-8e | G-1, 5-F | 3-CF₃-1H-pyrazol-1-yl | | 514 | 512 |
| 161 | A-1d | G-1, 5-F | 3-CHF₂-1H-pyrazol-1-yl | | 478 | |
| 162 | A-2b | G-1, 5-F | 3-CHF₂-1H-pyrazol-1-yl | | 463 | |
| 163 | A-7a | G-1, 5-F | 3-CF₃-1H-pyrazol-1-yl | 110-114 | | |
| 164 | A-3d | G-1, 5-Cl | 3-CF₃-1H-pyrazol-1-yl | | 464 | 462 |
| 165 | A-3b | G-1, 5-Cl | 3-CF₃-1H-pyrazol-1-yl | | 518 | 516 |
| 166 | A-8a | G-1, 5-Cl | 3-CF₃-1H-pyrazol-1-yl | | 518 | |
| 167 | A-4b | G-1, 5-Cl | 3-CF₃-1H-pyrazol-1-yl | | 517 | 515 |
| 168 | A-4c | G-1, 5-Cl | 3-CF₃-1H-pyrazol-1-yl | | 484 | |
| 169 | A-4h | G-1, 5-Cl | 3-CF₃-1H-pyrazol-1-yl | | 576 | 574 |
| 170 | A-8h | G-1, 5-Cl | 3-CF₃-1H-pyrazol-1-yl | | 465 | 463 |
| 171 | A-8e | G-1, 5-Cl | 3-CF₃-1H-pyrazol-1-yl | | 529 | |
| 172 | A-2b | G-5 | 3-CF₃-1H-pyrazol-1-yl | 221-225 | | |
| 173 | A-1d | G-5 | 3-CF₃-1H-pyrazol-1-yl | 215-218 | | |
| 174 | A-2b | G-5 | 3-Br-1H-pyrazol-1-yl | 155-159 | | |
| 175 | A-4d | G-1, 5-Cl | 3-CF₃-1H-pyrazol-1-yl | | 529 | 527 |
| 176 | A-4i | G-1, 5-Cl | 3-CF₃-1H-pyrazol-1-yl | | 468 | 466 |
| 185 | A-1x | G-1, 5-Cl | 3-CF₃-1H-pyrazol-1-yl | | 479 | 477 |
| 186 | A-1d | G-1, 5-Cl | 1H-pyrazol-1-yl | | 444 | |
| 187 | A-1d | G-1, 5-Br | 3-CF₃-1H-pyrazol-1-yl | | 558 | |

*See synthesis example for ¹H NMR data.

INDEX TABLE B

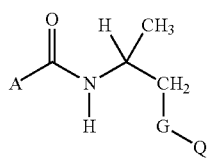

| Cmpd. No. | A | G, (R²)ₙ | Q | M + 1 |
|---|---|---|---|---|
| 83 | A-2b | G-1 | 3-CF₃-1H-pyrazol-1-yl | 429 |
| 84 (Ex. 1) | A-1d | G-1 | 3-CF₃-1H-pyrazol-1-yl | 444 |

* See synthesis example for ¹H NMR data.

INDEX TABLE C

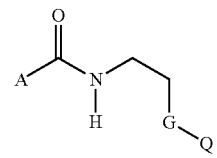

| Cmpd. No. | A | G, (R²)ₙ | Q | M.P. |
|---|---|---|---|---|
| 177 | A-1a | G-5 | 3-CF₃-1H-pyrazol-1-yl | 159-162 |
| 178 | A-1d | G-5 | 3-Me-1H-pyrazol-1-yl | 141-143 |
| 179 | A-1d | G-5 | 3-Br-1H-pyrazol-1-yl | 139-145 |
| 180 | A-1d | G-5 | 4-Br-1H-pyrazol-1-yl | 140-142 |
| 181 | A-1d | G-5 | 3-Cl-1H-pyrazol-1-yl | 157-160 |
| 182 | A-1d | G-5 | 4-Me-1H-pyrazol-1-yl | 121-124 |

INDEX TABLE C-continued

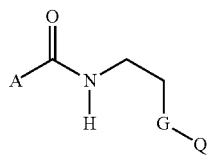

| Cmpd. No. | A | G, (R²)ₙ | Q | M.P. |
|---|---|---|---|---|
| 183 | A-1d | G-5 | 4-Cl-1H-pyrazol-1-yl | 154-157 |
| 184 | A-1d | G-5 | 3-CF₃-1H-pyrazol-1-yl | 137-140 |

Biological Examples of the Invention

General protocol for preparing test suspensions for Tests A-E: the test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-E. Compounds were sprayed with either a 40 ppm or 10 ppm (*) test suspension to the point of run-off on the test plants which is the equivalent of a rate of 160 g ai/ha or 40 g ai/ha, respectively.

Test A

The test suspension was sprayed to the point of run-off on tomato seedlings. The following day the seedlings were inoculated with a spore suspension of *Botrytis cinerea* (the causal agent of gray mold on many crops) and incubated in a saturated atmosphere at 20° C. for 48 h, and moved to a growth chamber at 27° C. for 2 days, after which time visual disease ratings were made.

Test B

The test suspension was sprayed to the point of run-off on wheat seedlings. The following day the seedlings were inoculated with a spore suspension of *Stagonospora nodorum* (also known as *Septoria nodorum*; the causal agent of wheat glume blotch) and incubated in a saturated atmosphere at 20° C. for 48 h, and then moved to a growth chamber at 20° C. for 6 days, after which time visual disease ratings were made.

Test C

The test suspension was sprayed to the point of run-off on wheat seedlings. The following day the seedlings were inoculated with a spore suspension of *Septoria tritici* (the causal agent of wheat leaf blotch) and incubated in a saturated atmosphere at 24° C. for 48 h, and then moved to a growth chamber at 20° C. for 21 days, after which time visual disease ratings were made.

Test D

The test suspension was sprayed to the point of run-off on wheat seedlings. The following day the seedlings were inoculated with a spore suspension of *Puccinia recondite* f. sp. *tritici*; (the causal agent of wheat leaf rust) and incubated in a saturated atmosphere at 20° C. for 24 h, and then moved to a growth chamber at 20° C. for 6 days, after which time visual disease ratings were made.

Test E

The test suspension was sprayed to the point of run-off on wheat seedlings. The following day the seedlings were inoculated with a spore dust of *Erysiphe graminis* f. sp. *tritici*, (the causal agent of wheat powdery mildew) and incubated in a growth chamber at 20° C. for 8 days, after which time visual disease ratings were made.

Results for Tests A-E are given in Table A. In the Table, a rating of 100 indicates 100% disease control and a rating of 0 indicates no disease control (relative to the controls). A dash (-) indicates no test results.

TABLE A

| Cmpd. No | Test A | Test B | Test C | Test D | Test E |
|---|---|---|---|---|---|
| 1 | 27 | 0 | 83 | 88 | 0 |
| 2 | 15 | 0 | 100 | 100 | 89 |
| 3 | 0 | 0 | 0 | 9 | 0 |
| 4 | 100 | 100 | 100 | 100 | 99 |
| 5 | 100 | 100 | 100 | 100 | 99 |
| 6 | 99 | 100 | 99 | 100 | 0 |
| 7 | 100 | 100 | 100 | 100 | 97 |
| 8 | 99 | 99 | 99 | 100 | 99 |
| 9 | 100 | 100 | 100 | 100 | 100 |
| 10 | 100 | 100 | 100 | 100 | 97 |
| 11 | 100 | 100 | 100 | 100 | 99 |
| 12 | — | 100 | 100 | 99 | 98 |
| 13 | 98 | 98 | 100 | 100 | 99 |
| 14 | — | 100 | 100 | 99 | 98 |
| 15 | — | 99 | 100 | 100 | 97 |
| 16 | — | 100 | 100 | 99 | 69 |
| 17 | 98 | 100 | 100 | 99 | 0 |
| 18 | 96 | 100 | 100 | 99 | 0 |
| 19 | 98 | 100 | 100 | 100 | 87 |
| 20 | 89 | 100 | 96 | 99 | 0 |
| 21 | 99 | 97 | 81 | 100 | 43 |
| 22 | 94 | 0 | 33 | 100 | 21 |
| 23 | 20 | 0 | 100 | 96 | 99 |
| 24 | 99 | 100 | 100 | 100 | 100 |
| 25 | 99 | 82 | 100 | 98 | 90 |
| 26 | 88 | 90 | 100 | 99 | 100 |
| 27 | 89 | 99 | 100 | 98 | 96 |
| 28 | 99 | 99 | 100 | 99 | 96 |
| 29 | 77 | 99 | 100 | 89 | 82 |
| 30 | 33 | 82 | 91 | 89 | 69 |
| 31 | 100 | 100 | 100 | 100 | 99 |
| 32 | 99 | 100 | 100 | 100 | 99 |
| 33 | 15 | 60 | 100 | 100 | 99 |
| 34 | 96 | 100 | 100 | 100 | 100 |
| 35 | 97 | 100 | 100 | 100 | 100 |
| 36 | 28 | 98 | 100 | 100 | 99 |
| 37 | 95 | 100 | 100 | 100 | 100 |
| 38 | 90 | 100 | 100 | 100 | 100 |
| 39 | 45 | 0 | 92 | 92 | 89 |
| 40 | — | — | — | — | — |
| 41 | 99 | 40 | 100 | 100 | 84 |
| 42 | 40 | 0 | 87 | 68 | 21 |
| 43 | 94 | 99 | 98 | 74 | 92 |
| 44 | 40 | 0 | 62 | 99 | 0 |
| 45 | 99 | 98 | 100 | 100 | 99 |
| 46 | 21 | 0 | 8 | 97 | 0 |
| 47 | 91 | 0 | 82 | 100 | 0 |
| 48 | 0 | 0 | 73 | 0 | 56 |
| 49 | 0 | 0 | 100 | 100 | 99 |
| 50 | 99 | 100 | 100 | 100 | 100 |
| 51 | 97 | 100 | 100 | 100 | 100 |
| 52 | 36 | 0 | 99 | 96 | 50 |
| 53 | 0 | 0 | 0 | 55 | 0 |
| 54 | 0 | 0 | 0 | 86 | 0 |
| 55 | 0 | 0 | 100 | 91 | 0 |

TABLE A-continued
| Cmpd. No | Test A | Test B | Test C | Test D | Test E |
|---|---|---|---|---|---|
| 56 | 16 | 0 | 100 | 99 | 99 |
| 57 | 0 | 0 | 32 | 100 | 0 |
| 58 | 0 | 0 | 100 | 100 | 99 |
| 59 | 0 | 0 | 33 | 9 | 98 |
| 60 | 34 | 0 | 100 | 100 | 99 |
| 61 | 41 | 99 | 100 | 100 | 99 |
| 62 | 84 | 0 | 100 | 100 | 98 |
| 63 | 27 | 0 | 92 | 99 | 72 |
| 64 | 98 | 60 | 100 | 100 | 96 |
| 65 | 99 | 97 | 100 | 100 | 94 |
| 66 | 32 | 0 | 18 | 89 | 0 |
| 67 | 7 | 0 | 62 | 90 | 0 |
| 68 | 94 | 100 | 100 | 100 | 100 |
| 69 | 99 | 100 | 100 | 100 | 100 |
| 70 | 99 | 99 | 100 | 100 | 100 |
| 71 | 94 | 100 | 100 | 100 | 100 |
| 72 | 92 | 0 | 100 | 97 | 91 |
| 73 | 96 | 100 | 100 | 100 | 100 |
| 74 | 96 | 0 | 100 | 100 | 100 |
| 75 | 99 | 98 | 100 | 100 | 100 |
| 76 | 99 | 0 | 100 | 100 | 99 |
| 77 | 74 | 0 | 100 | 100 | 98 |
| 78 | 28 | 0 | 100 | 100 | 97 |
| 79 | 25 | 0 | 100 | 100 | 99 |
| 80 | 0 | 0 | 100 | 88 | 0 |
| 81 | 60 | 73 | 13 | 92 | 0 |
| 82 | 31* | 97* | 48* | 97* | 0* |
| 83 | 99 | 99 | 100 | 0 | 93 |
| 84 | 66 | 99 | 100 | 0 | 90 |
| 85 | 70 | 0 | 45 | 99 | 0 |
| 86 | 89 | 0 | 98 | 100 | 79 |
| 87 | 99 | 0 | 97 | 100 | 64 |
| 88 | 100 | 0 | 51 | 100 | 93 |
| 89 | 75 | 0 | — | 100 | 79 |
| 90 | 93 | 46 | — | 100 | 72 |
| 91 | 87 | 33 | — | 100 | 56 |
| 92 | 0 | 60 | — | 100 | 98 |
| 93 | 0 | 97 | — | 100 | 99 |
| 94 | 0 | 98 | — | 100 | 99 |
| 95 | 0 | 100 | — | 100 | 98 |
| 96 | 0 | 60 | — | 99 | 96 |
| 97 | 0 | 87 | — | 100 | 99 |
| 98 | 67 | 0 | 75 | 100 | 48 |
| 99 | 89 | 0 | 90 | 100 | 91 |
| 100 | 58 | 60 | 87 | 100 | 69 |
| 101 | 71 | 60 | 94 | 100 | 92 |
| 102 | — | 99 | 97 | 100 | 73 |
| 103 | — | — | — | — | — |
| 104 | — | — | — | — | — |
| 105 | — | — | — | 100 | 81 |
| 106 | — | — | — | 100 | 98 |
| 107 | — | — | — | 99 | 43 |
| 108 | — | — | — | 96 | 87 |
| 109 | — | — | 66 | 74 | 0 |
| 110 | — | — | 22 | 68 | 0 |
| 111 | — | — | 63* | 84* | 0* |
| 112 | — | — | 77* | 0* | 0* |
| 113 | — | 0 | 77 | 97 | 0 |
| 114 | — | 0 | 84 | 100 | 64 |
| 115 | — | 100 | 98 | 100 | 100 |
| 116 | — | — | 99* | 99* | 64* |
| 117 | — | — | 99* | 99* | 64* |
| 118 | — | — | 42* | 68* | 0* |
| 119 | — | — | — | — | — |
| 120 | — | — | 98* | 100* | 0* |
| 121 | — | — | — | — | — |
| 122 | — | — | — | — | — |
| 123 | — | — | — | — | — |
| 124 | — | — | — | — | — |
| 125 | — | — | — | — | — |
| 126 | — | 99 | 99 | 100 | 99 |
| 127 | — | 0 | 62* | 100* | 40* |
| 128 | — | — | 42* | 67* | 13* |
| 129 | — | — | 88* | 17* | 0* |
| 130 | — | 11 | 89 | 97 | 69 |
| 131 | — | — | — | — | — |
| 132 | — | 0 | 99 | 99 | 98 |
| 133 | — | — | — | — | — |
| 134 | — | — | — | — | — |
| 135 | — | — | — | — | — |
| 136 | — | — | — | — | — |
| 137 | — | — | — | — | — |
| 138 | — | — | 99* | 100* | 64* |
| 139 | — | — | 98* | 100* | 40* |
| 140 | — | — | — | — | — |
| 141 | — | — | 76* | 97* | 0* |
| 142 | — | — | 88* | 97* | 0* |
| 143 | — | — | 100* | 100* | 64* |
| 144 | — | 0 | 81 | 68 | 0 |
| 145 | — | 0 | 26 | 0 | 0 |
| 146 | — | 0 | 1 | 0 | 0 |
| 147 | — | — | 100* | 100* | 92* |
| 148 | — | — | 100* | 100* | 91* |
| 149 | — | 95 | 97 | 99 | 98 |
| 150 | — | 92 | 98 | 100 | 99 |
| 151 | — | 0 | 98 | 100 | 98 |
| 152 | — | 99 | 99 | 100 | 99 |
| 153 | — | — | 99* | 99* | 40* |
| 154 | — | 59* | 94* | 100* | 0* |
| 155 | — | — | — | — | — |
| 156 | — | — | — | — | — |
| 157 | — | — | — | — | — |
| 158 | — | — | — | — | — |
| 159 | — | — | — | — | — |
| 160 | — | — | — | — | — |
| 161 | — | 100 | 95 | 100 | 99 |
| 162 | — | 68 | 98 | 100 | 99 |
| 163 | — | 79 | 97 | 100 | 96 |
| 164 | — | — | 96* | 91* | 69* |
| 165 | — | 0 | 99* | 98* | 87* |
| 166 | — | 0 | 99* | 98* | 64* |
| 167 | — | 98* | 100* | 100* | 94* |
| 168 | — | 0* | 95* | 99* | 64* |
| 169 | — | 99* | 100* | 100* | 87* |
| 170 | — | 50* | 74* | 0* | 0* |
| 171 | — | 0* | 96* | 99* | 40* |
| 172 | — | — | — | — | — |
| 173 | — | — | — | — | — |
| 174 | — | — | — | — | — |
| 175 | — | 92* | 100* | 100* | 64* |
| 176 | — | 0* | 93* | 0* | 0* |
| 177 | — | — | 91 | 0 | 79 |
| 178 | — | 3* | 0* | 0* | 0* |
| 179 | — | 0 | 5* | 0* | 0* |
| 180 | — | 0 | 2* | 0* | 0* |
| 181 | — | 64* | 20* | 9* | 0* |
| 182 | — | 0 | 9* | 0* | 0* |
| 183 | — | — | — | — | — |
| 184 | — | — | — | — | — |
| 185 | — | — | — | — | — |
| 186 | — | — | — | — | — |
| 187 | — | — | — | — | — |
What is claimed is:
1. A compound selected from Formula 1, N-oxides and salts thereof,
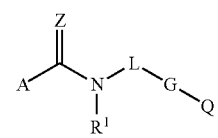

wherein

A is a radical selected from the group consisting of

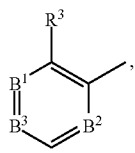 A-1

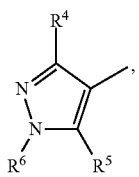 A-2

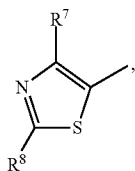 A-3

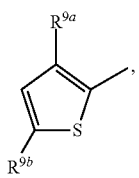 A-4

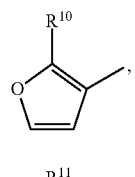 A-5

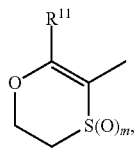 A-6

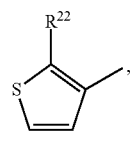 A-7

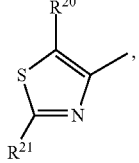 A-8

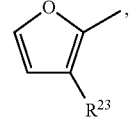 A-9

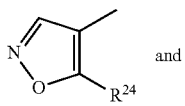 A-10 and

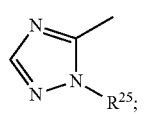 A-11

A-11

Z is O or S;

$R^1$ is H, cyclopropyl or $C_1$-$C_2$ alkoxy;

L is —C($R^{12a}$)$R^{12b}$—C($R^{13a}$)$R^{13b}$—, wherein the carbon atom bonded to $R^{12a}$ and $R^{12b}$ is also bonded to the carboxamide nitrogen atom in Formula 1; or 1,2-phenylene optionally substituted with up to 4 substituents independently selected from halogen and $C_1$-$C_2$ alkyl;

G is a radical selected from the group consisting of

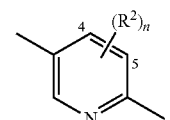 G-1

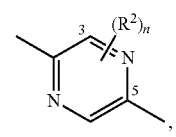 G-2

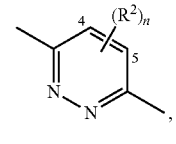 G-3

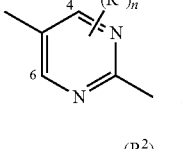 G-4 and

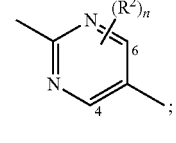 G-5 each $R^2$ is independently halogen, nitro, cyano, $C_1$-$C_5$ alkyl, $C_1$-$C_5$ haloalkyl, $C_1$-$C_5$ alkoxy, $C_1$-$C_5$ haloalkoxy or $C_3$-$C_5$ cycloalkyl;

$B^1$ is CH or N;
$B^2$ is CH or N;
$B^3$ is CH or N;
provided when $B^1$ and $B^2$ are both N, then $B^3$ is CH;
$R^3$ is halogen, $C_1$-$C_3$ alkyl or $C_1$-$C_3$ haloalkyl;
$R^4$ is halogen, $C_1$-$C_3$ alkyl or $C_1$-$C_3$ haloalkyl;
$R^5$ is H, halogen, $C_1$-$C_3$ alkyl or $C_1$-$C_3$ haloalkyl;
$R^6$ is $C_1$-$C_2$ alkyl;
$R^7$ is halogen, $C_1$-$C_3$ alkyl or $C_1$-$C_3$ haloalkyl;
$R^8$ is H, $C_1$-$C_2$ alkyl or $C_1$-$C_2$ haloalkyl;

$R^{9a}$ is H, halogen, $C_1$-$C_3$ alkyl, $C_1$-$C_3$ haloalkyl or $C_1$-$C_3$ alkylthio;
$R^{9b}$ is H, halogen, $C_1$-$C_3$ alkyl or $C_1$-$C_3$ haloalkyl;
$R^{10}$ is halogen, $C_1$-$C_3$ alkyl or $C_1$-$C_3$ haloalkyl;
$R^{11}$ is halogen, $C_1$-$C_3$ alkyl or $C_1$-$C_3$ haloalkyl;
$R^{20}$ is halogen, $C_1$-$C_3$ alkyl or $C_1$-$C_3$ haloalkyl;
$R^{21}$ is H, $C_1$-$C_2$ alkyl or $C_1$-$C_2$ haloalkyl;
$R^{22}$ is H, halogen, $C_1$-$C_3$ alkyl, $C_1$-$C_3$ haloalkyl or $C_1$-$C_3$ alkylthio;
$R^{23}$ is H, halogen, $C_1$-$C_3$ alkyl or $C_1$-$C_3$ haloalkyl;
$R^{24}$ is H, halogen, $C_1$-$C_3$ alkyl or $C_1$-$C_3$ haloalkyl;
$R^{25}$ is H, $C_1$-$C_3$ alkyl or $C_1$-$C_3$ haloalkyl;
m is 0, 1 or 2;
n is 0, 1, 2 or 3;
$R^{12a}$ and $R^{12b}$ are each independently H, $C_1$-$C_2$ alkyl or $C_1$-$C_2$ haloalkyl; or $R^{12a}$ and $R^{12b}$ are taken together as $C_2$-$C_5$ alkanediyl;
$R^{13a}$ is H, halogen, $C_1$-$C_2$ alkyl, $C_1$-$C_2$ haloalkyl, $C_1$-$C_2$ alkoxy, $C_1$-$C_2$ haloalkoxy, $C_1$-$C_2$ alkylthio or $C_1$-$C_2$ alkoxyamino;
$R^{13b}$ is H, halogen, $C_1$-$C_2$ alkyl or $C_1$-$C_2$ haloalkyl; or $R^{13a}$ and $R^{13b}$ are taken together as $C_2$-$C_5$ alkanediyl;
Q is a 5-membered unsaturated or partially unsaturated heterocyclic ring containing ring members selected from carbon atoms and up to 4 heteroatoms independently selected from up to 1 O, up to 1 S and up to 4 N atoms, wherein up to 2 carbon atom ring members are independently selected from C(=O), the heterocyclic ring optionally substituted with one substituent on a ring member distal relative to the ring member connecting the heteroaromatic ring to the remainder of Formula 1, said optional substituent selected from $R^{14c}$ on carbon atom ring members and from $R^{14n}$ on nitrogen atom ring members, the heterocyclic ring further optionally substituted with substituents selected from $R^{15c}$ on carbon atom ring members and $R^{15n}$ on nitrogen atom ring members;
each $R^{14c}$ is independently halogen, cyano, $C_1$-$C_3$ alkyl, $C_1$-$C_3$ haloalkyl, $C_1$-$C_3$ alkoxy, $C_1$-$C_3$ haloalkoxy, $C_2$-$C_3$ alkoxycarbonyl or $C_2$-$C_3$ alkylcarbonyl; or a phenyl ring optionally substituted with up to 5 substituents independently selected from $R^{16}$; or a heteroaromatic ring optionally substituted with up to 4 substituents independently selected from $R^{17c}$ on carbon atom ring members and from $R^{17n}$ on nitrogen atom ring members; or
two $R^{14c}$ bonded to adjacent carbon atoms are taken together with carbon atom ring members to form a 5- or 6-membered carbocyclic or partially aromatic ring, the ring optionally substituted with halogen or $C_1$-$C_4$ alkyl;
each $R^{14n}$ is independently $C_1$-$C_3$ alkyl, $C_1$-$C_3$ haloalkyl or $C_1$-$C_3$ alkoxy; or a phenyl ring optionally substituted with up to 5 substituents independently selected from $R^{18}$; or a heteroaromatic ring optionally substituted with up to 4 substituents independently selected from $R^{19c}$ on carbon atom ring members and from $R^{19n}$ on nitrogen atom ring members;
each $R^{15c}$ is independently halogen, $C_1$-$C_3$ alkyl, $C_1$-$C_3$ haloalkyl or $C_1$-$C_3$ alkoxy;
each $R^{15n}$ is independently $C_1$-$C_3$ alkyl, $C_1$-$C_3$ haloalkyl or $C_1$-$C_3$ alkoxy;
each $R^{16}$, $R^{17c}$, $R^{18}$ and $R^{19c}$ is independently halogen, cyano, $C_1$-$C_2$ alkyl, $C_1$-$C_2$ haloalkyl, $C_1$-$C_2$ alkoxy or $C_1$-$C_2$ haloalkoxy; and
each $R^{17n}$ and $R^{19n}$ is independently $C_1$-$C_2$ alkyl, $C_1$-$C_2$ haloalkyl or $C_1$-$C_2$ alkoxy.

2. A compound of claim 1 wherein
Z is O;
L is —C($R^{12a}$)$R^{12b}$—C($R^{13a}$)$R^{13b}$—; or 1,2-phenylene optionally substituted with up to 2 substituents independently selected from F, Cl, Br and $CH_3$;
G is selected from the group consisting of G-1, G-2, G-3 and G-4;
each $R^2$ is independently halogen or $C_1$-$C_5$ alkyl;
n is 0, 1 or 2;
$R^3$ is halogen, $C_1$-$C_2$ alkyl or $C_1$-$C_2$ haloalkyl;
$R^4$ is halogen, $C_1$-$C_2$ alkyl or $C_1$-$C_2$ haloalkyl;
$R^5$ is H, halogen, $C_1$-$C_2$ alkyl or $C_1$-$C_2$ haloalkyl;
$R^6$ is $CH_3$;
$R^7$ is halogen, $C_1$-$C_2$ alkyl or $C_1$-$C_2$ haloalkyl;
$R^8$ is H or $CH_3$;
$R^{9a}$ is halogen, $C_1$-$C_2$ alkyl, $C_1$-$C_2$ haloalkyl or $C_1$-$C_2$ alkylthio;
$R^{9b}$ is H, halogen, $C_1$-$C_2$ alkyl;
$R^{10}$ is halogen, $C_1$-$C_2$ alkyl or $C_1$-$C_2$ haloalkyl;
$R^{11}$ is halogen, $C_1$-$C_2$ alkyl or $C_1$-$C_2$ haloalkyl;
$R^{22}$ is F, Cl, $CH_3$ or $CF_3$;
$R^{12a}$ is H or $CH_3$;
$R^{12b}$ is H or $CH_3$; or
$R^{12a}$ and $R^{12b}$ are taken as $C_2$ or $C_3$ alkanediyl;
$R^{13a}$ is H, $CH_3$, or $OCH_3$;
$R^{13b}$ is H or $CH_3$; or
$R^{13a}$ and $R^{13b}$ are taken together as $C_2$ or $C_3$ alkanediyl;
Q is selected from

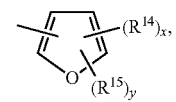

Q-1

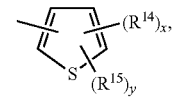

Q-2

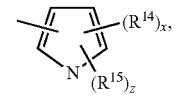

Q-3

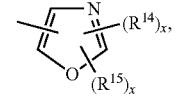

Q-4

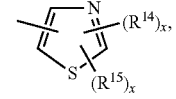

Q-5

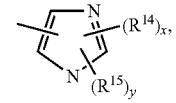

Q-6

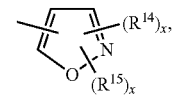

Q-7

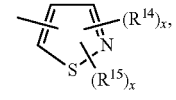

Q-8

-continued

Q-9 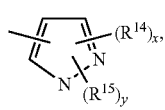

Q-10 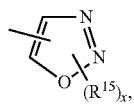

Q-11 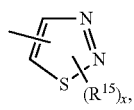

Q-12 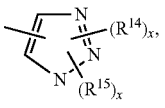

Q-13 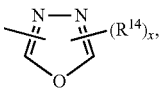

Q-14 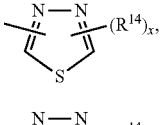

Q-15 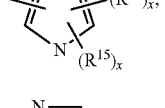

Q-16 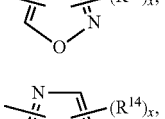

Q-17 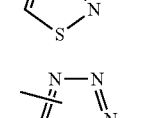

Q-18 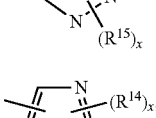

Q-19 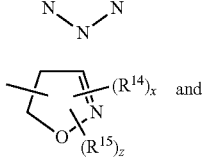

Q-20 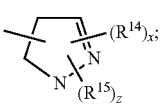

Q-21 wherein
$R^{14}$ is bonded to a ring member distal relative to the ring member connecting the Q ring to the remainder of Formula 1, and independently selected from $R^{14c}$ on carbon atom ring members and $R^{14n}$ on nitrogen atom ring members;

each $R^{15}$ is independently selected from $R^{15c}$ on carbon atom ring members and $R^{15n}$ on nitrogen atom ring members;
each x is independently 0 or 1;
each y is independently 0, 1 or 2;
each z is independently 0, 1, 2 or 3;
each $R^{16}$, $R^{17c}$, $R^{18}$ and $R^{19c}$ is independently F, Cl, Br, $CH_3$, $CHF_2$ or $CF_3$; and
each $R^{17n}$ and $R^{19n}$ is $CH_3$.

3. The compound of claim 2 wherein
A is selected from the group consisting of A-1, A-2, A-4 and A-8;
L is —C($R^{12a}$)$R^{12b}$—C($R^{13a}$)$R^{13b}$—;
G is selected from the group consisting of G-1 and G-4;
$B^1$ is CH;
each $R^2$ is independently F, Cl, Br or $CH_3$;
n is 0 or 1;
$R^3$ is F, Cl, Br, $CH_3$, $CHF_2$ or $CF_3$;
$R^4$ is F, Cl, Br, $CH_3$, $CHF_2$ or $CF_3$;
$R^5$ is H, halogen, $CH_3$ or $C_1$ haloalkyl;
$R^6$ is $CH_3$;
$R^{9a}$ is F, Cl, Br, $CHF_2$ or $CF_3$;
$R^{9b}$ is H, halogen or $C_1$-$C_2$ alkyl;
$R^{20}$ is Cl, $CH_3$ or $CF_3$;
$R^{21}$ is H or $CH_3$;
$R^{14c}$ is independently F, Cl, Br, $CH_3$, $CHF_2$ or $CF_3$;
Q is selected from Q-9A 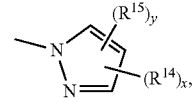

Q-9B 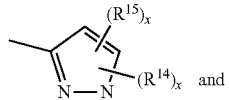

Q-9C 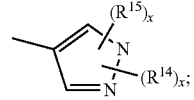

each $R^{14n}$ is $CH_3$;
each $R^{15c}$ is independently F, Cl, Br, $CH_3$, $CHF_2$ or $CF_3$; and
each $R^{15n}$ is $CH_3$.

4. The compound of claim 3 wherein
A is selected from the group consisting of A-1, A-2 and A-8;
$B^2$ is N;
$B^3$ is CH;
$R^1$ is H;
G is G-1 substituted with at least one $R^2$ ortho to the bond to Q;
each $R^2$ is independently F or Cl;
Q is selected from Q-9A and Q-9B;
$R^3$ is $CF_3$;
$R^4$ is $CHF_2$;
$R^5$ is H, F, Cl, Br, $CH_3$, $CHF_2$ or $CF_3$;
$R^{20}$ is $CH_3$ or $CF_3$;
$R^{21}$ is H;
$R^{12a}$ is H;
$R^{12b}$ is H;
$R^{13a}$ is H or $CH_3$; and
$R^{13b}$ is H.

5. The compound of claim 2 wherein
A is selected from the group consisting of A-1, A-2 and A-4;
L is 1,2-phenylene optionally substituted with up to 2 substituents independently selected from F, Cl, Br and $CH_3$;
G is selected from G-1, G-2 and G-3;
each $R^2$ is independently F, Cl, Br or $CH_3$;
n is 0 or 1;
$R^3$ is F, Cl, Br, $CH_3$, $CHF_2$ or $CF_3$;
$R^4$ is F, Cl, Br, $CH_3$, $CHF_2$ or $CF_3$;
$R^5$ is H, halogen, $CH_3$ or $C_1$ haloalkyl;
$R^6$ is $CH_3$;
$R^{9a}$ is F, Cl, Br, $CHF_2$ or $CF_3$;
$R^{9b}$ is H or methyl;
Q is selected from

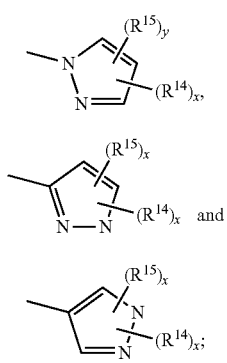

$R^{14c}$ is independently F, Cl, Br, $CH_3$, $CHF_2$ or $CF_3$;
each $R^{14n}$ is $CH_3$;
each $R^{15c}$ is independently F, Cl, Br, $CH_3$, $CHF_2$ or $CF_3$; and
each $R^{15n}$ is $CH_3$.

6. The compound of claim 5 wherein
A is selected from the group consisting of A-1 and A-2;
L is 1,2-phenylene optionally substituted with up to 2 substituents independently selected from F and $CH_3$;
$B^1$ is CH;
$B^3$ is CH;
G is G-1;
each $R^2$ is independently F or Cl;
$R^3$ is $CF_3$;
$R^4$ is $CHF_2$;
$R^5$ is H, F, Cl, Br, $CH_3$, $CHF_2$ or $CF_3$; and
Q is selected from Q-9A and Q-9B.

7. The compound of claim 6 wherein
A is A-1;
L is 1,2-phenylene;
$B^2$ is N;
G-1 is substituted with at least one $R^2$ ortho to the bond in Formula 1 bonded to the bond with Q;
each $R^2$ is independently F or Cl; and
Q is Q-9A.

8. A compound of claim 1 selected from the group consisting of:
3-(difluoromethyl)-N-[2-[5-fluoro-6-[3-(trifluoromethyl)-1H-pyrazol-1-yl]-3-pyridinyl]phenyl]-1-methyl-1H-pyrazole-4-carboxamide;
3-(difluoromethyl)-1-methyl-N-[2-[2-[3-(trifluoromethyl)-1H-pyrazol-1-yl]-5-pyrimidinyl]phenyl]-1H-pyrazole-4-carboxamide;
3-(difluoromethyl)-1-methyl-N-[2-[6-[3-(trifluoromethyl)-1H-pyrazol-1-yl]-3-pyridazinyl]phenyl]-1H-pyrazole-4-carboxamide;
3-(difluoromethyl)-1-methyl-N-[2-[5-[3-(trifluoromethyl)-1H-pyrazol-1-yl]-2-pyrazinyl]phenyl]-1H-pyrazole-4-carboxamide;
3-(difluoromethyl)-1-methyl-N-[1-methyl-2-[6-[3-(trifluoromethyl)-1H-pyrazol-1-yl]-3-pyridinyl]ethyl]-1H-pyrazole-4-carboxamide; and
N-[1-methyl-2-[6-[3-(trifluoromethyl)-1H-pyrazol-1-yl]-3-pyridinyl]ethyl]-3-(trifluoromethyl)-2-pyridinecarboxamide.

9. A compound of claim 1 also selected from the group consisting of:
3-(difluoromethyl)-N-[2-[6-[3-(trifluoromethyl)-1H-pyrazol-1-yl]-3-pyridinyl]phenyl]-1-methyl-1H-pyrazole-4-carboxamide;
N-[2-[5-chloro-6-[3-(trifluoromethyl)-1H-pyrazol-1-yl]-3-pyridinyl]phenyl]-3-(trifluoromethyl)-2-pyridinecarboxamide;
N-[2-[5-fluoro-6-[3-(trifluoromethyl)-1H-pyrazol-1-yl]-3-pyridinyl]phenyl]-3-(trifluoromethyl)-2-pyridinecarboxamide;
N-[2-[5-chloro-6-[3-(trifluoromethyl)-1H-pyrazol-1-yl]-3-pyridinyl]phenyl]-3-iodo-2-thiophenecarboxamide;
N-[2-[5-fluoro-6-[3-(trifluoromethyl)-1H-pyrazol-1-yl]-3-pyridinyl]phenyl]-3-iodo-2-thiophenecarboxamide;
5-bromo-N-[2-[5-chloro-6-[3-(trifluoromethyl)-1H-pyrazol-1-yl]-3-pyridinyl]phenyl]-4-thiazolecarboxamide;
N-[2-[5-chloro-6-[3-(trifluoromethyl)-1H-pyrazol-1-yl]-3-pyridinyl]phenyl]-5-iodo-4-thiazolecarboxamide;
3-bromo-N-[2-[5-chloro-6-[3-(trifluoromethyl)-1H-pyrazol-1-yl]-3-pyridinyl]phenyl]-2-thiophenecarboxamide;
N-[2-[5-chloro-6-[3-(trifluoromethyl)-1H-pyrazol-1-yl]-3-pyridinyl]phenyl]-3-iodo-2-pyridinecarboxamide;
3-bromo-N-[2-[5-chloro-6-[3-(trifluoromethyl)-1H-pyrazol-1-yl]-3-pyridinyl]phenyl]-2-pyridinecarboxamide;
N-[2-[5-chloro-6-[4-chloro-1H-pyrazol-1-yl]-3-pyridinyl]phenyl]-3-(trifluoromethyl)-2-pyridinecarboxamide;
2-(trifluoromethyl)-N-[2-[5-[3-(trifluoromethyl)-1H-pyrazol-1-yl]-2-pyrazinyl]phenyl]benzamide;
3-(trifluoromethyl)-N-[2-[2-[3-(trifluoromethyl)-1H-pyrazol-1-yl]-5-pyrimidinyl]phenyl]-2-pyridinecarboxamide;
N-[2-[5-chloro-6-(1H-pyrazol-1-yl)-3-pyridinyl]phenyl]-3-(trifluoromethyl)-2-pyridinecarboxamide; and
N-[2-[5-bromo-6-[3-(trifluoromethyl)-1H-pyrazol-1-yl]-3-pyridinyl]phenyl]-3-(trifluoromethyl)-2-pyridinecarboxamide.

10. A fungicidal composition comprising (a) a compound of claim 1; and (b) at least one other fungicide.

11. A fungicidal composition comprising (a) a compound of claim 1; and (b) at least one additional component selected from the group consisting of surfactants, solid diluents and liquid diluents.

12. A method for controlling plant diseases caused by fungal plant pathogens comprising applying to the plant or portion thereof, or to the plant seed, a fungicidally effective amount of a compound of claim 1.

13. The method of claim 12 wherein the fungal plant pathogens are resistant to succinate dehydrogenase inhibitors.

14. The method of claim 13 wherein the fungal plant pathogens resistant to succinate dehydrogenase inhibitors are selected from the group consisting of *Alternaria alter-* nata, *Aspergillus oryzae, Botrytis cinearea, Botrytis elliptica, Corynespora cassiicola, Didymella bryoniae, Mycosphaerella graminicola, Podosphaera xanthii, Sclerotinia sclerotiorum, Stemphylium botryose* and *Ustilago maydis*.

* * * * *